(12) United States Patent
Toyoda et al.

(10) Patent No.: US 8,778,970 B2
(45) Date of Patent: Jul. 15, 2014

(54) BENZYL PIPERIDINE COMPOUND

(75) Inventors: Tomohiro Toyoda, Suita (JP); Tomoaki Nishida, Osaka (JP); Hidefumi Yoshinaga, Osaka (JP)

(73) Assignee: Dainippon Sumitomo Pharma Co., Ltd, Osaka (JP)

( * ) Notice: Subject to any disclaimer, the term of this patent is extended or adjusted under 35 U.S.C. 154(b) by 36 days.

(21) Appl. No.: 13/388,623

(22) PCT Filed: Aug. 4, 2010

(86) PCT No.: PCT/JP2010/063148
§ 371 (c)(1),
(2), (4) Date: Feb. 2, 2012

(87) PCT Pub. No.: WO2011/016468
PCT Pub. Date: Feb. 10, 2011

(65) Prior Publication Data
US 2012/0130077 A1    May 24, 2012

(30) Foreign Application Priority Data
Aug. 4, 2009    (JP) .................. 2009-181550

(51) Int. Cl.
*A61K 31/453*    (2006.01)
*C07D 405/10*    (2006.01)

(52) U.S. Cl.
USPC ........................... 514/320; 546/196

(58) Field of Classification Search
USPC ........................... 514/320; 546/196
See application file for complete search history.

(56) References Cited

U.S. PATENT DOCUMENTS

| | | | |
|---|---|---|---|
| 4,921,863 A | 5/1990 | Sugimoto et al. | |
| 5,698,553 A | 12/1997 | Prucher et al. | |
| 6,124,323 A | 9/2000 | Bigge et al. | |
| 6,284,774 B1 | 9/2001 | Wright et al. | |
| 6,787,560 B2 | 9/2004 | Kodo et al. | |
| 8,063,223 B2 * | 11/2011 | Toyoda et al. | 546/196 |
| 8,232,405 B2 * | 7/2012 | Toyoda et al. | 546/196 |
| 2003/0191126 A1 | 10/2003 | Kodo et al. | |
| 2005/0065140 A1 | 3/2005 | Kodo et al. | |
| 2007/0219179 A1 | 9/2007 | Suzuki et al. | |
| 2010/0113792 A1 | 5/2010 | Toyoda et al. | |
| 2011/0118312 A1 | 5/2011 | Toyoda et al. | |

FOREIGN PATENT DOCUMENTS

| | | |
|---|---|---|
| AU | 9671774 | 11/1996 |
| CA | 2188485 A1 | 5/1997 |
| EP | 0934932 A1 | 8/1999 |
| FR | 2672286 A1 | 8/1992 |
| FR | 2696741 A1 | 4/1994 |
| FR | 2697251 A1 | 4/1994 |
| JP | 2000-500773 A | 1/2000 |
| WO | 88/02365 A1 | 4/1988 |
| WO | WO 97/23216 A1 | 7/1997 |
| WO | 98/08816 A1 | 3/1998 |
| WO | 01/43740 A1 | 6/2001 |
| WO | WO 02/06231 A1 | 1/2002 |
| WO | WO 03/053928 A1 | 7/2003 |
| WO | 2004/046124 A1 | 6/2004 |
| WO | 2005/108389 A1 | 11/2005 |
| WO | WO 2009/099087 | 8/2009 |

OTHER PUBLICATIONS

Y. Sato et al., "Syntheses and Pharmacology of 1-[2-(2-Hydroxyethoxy)-ethyl]-4-p-chlorobenzylpiperidine Hydrochloride (Piclobetol) and the Related Compounds", Ann. Sankyo Res. Lab., vol. 23, 1971, pp. 104-116.

A.M. Ismaiel et al., "Ketanserin Analogues: The Effect of Structural Modification on 5-HT2 Serotonin Receptor Binding", J. Med. Chem., vol. 38, 1995, pp. 1196-1202.

Klaus Rehse et al., "Neuropsychotrope Aktivitat dopaminanaloger Piperidin- und Piperazinderivate", Arch. Pharm. (Weinheim), vol. 312, 1979, pp. 670-681.

* cited by examiner

*Primary Examiner* — Celia Chang
(74) *Attorney, Agent, or Firm* — Sughrue Mion, PLLC

(57) ABSTRACT

Provided is a new serotonin-reuptake inhibitor that exhibits affinity for serotonin-1A receptors. Said serotonin-reuptake inhibitor is a compound represented by formula (1) or a pharmacologically acceptable salt thereof. In the formula, $R^1$ represents a hydrogen atom, a 2-hydroxyethyl group, or a 2-methoxyethyl group. $R^2$ represents one of the following bonded to a methylene group which is bonded to a piperidine ring: a chlorine atom bonded in a p-position; a bromine atom bonded in a p-position; a methyl group bonded in a p-position; a chlorine atom bonded in an m-position; or a bromine atom bonded in an m-position. Either $Y^1$ represents a hydrogen atom and $Y^2$ represents a hydrogen atom or a hydroxyl group, or $Y^1$ and $Y^2$ together represent an oxo group. Z represents a group represented by one of the following formulas: formula (3-1-1), formula (3-1-2), formula (3-2-1), formula (3-2-2), formula (3-3-1), formula (3-3-2), formula (3-4-1), or formula (3-4-2). However, if $R^1$ represents a 2-hydroxyethyl group or a 2-methoxyethyl group and $Y^1$ and $Y^2$ both simultaneously represent hydrogen atoms, then Z represents a group represented by one of the following formulas: formula (3-1-2), formula (3-2-1), formula (3-2-2), formula (3-3-1), formula (3-3-2), formula (3-4-1), or formula (3-4-2).

(1)

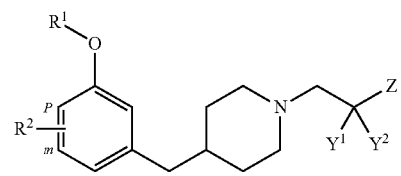

15 Claims, No Drawings

BENZYL PIPERIDINE COMPOUND

CROSS REFERENCE TO RELATED APPLICATIONS

This application is a National Stage of International Application No. PCT/JP2010/063148 filed Aug. 4, 2010, claiming priority based on Japanese Patent Application No. 2009-181550, filed Aug. 4, 2009, the contents of all of which are incorporated herein by reference in their entirety.

TECHNICAL FIELD

The present invention relates to a novel benzylpiperidine compound or a pharmaceutically acceptable salt thereof that is useful as a serotonin reuptake inhibitor. More specifically, the benzylpiperidine compound of the present invention is a compound comprising, as a common chemical structure, 4-benzylpiperidine having an oxygen atom at 3-position of the benzene ring moiety, and further has, at 1-position of piperidine, a 2-(chroman-6-yl)ethyl group or a 2-(4H-chromen-6-yl)ethyl group substituted by a hydroxy group and/or an oxo group. The benzylpiperidine compound of the present invention has a serotonin reuptake inhibitory effect and is thus useful as, for example, an antidepressant.

BACKGROUND ART

Depression is a chronic disease that affects people of every age. Of various antidepressants currently used, the most successful one is a selective serotonin reuptake inhibitor (hereinafter, also abbreviated to SSRI). SSRI has a serotonin reuptake inhibitory effect higher than dopamine and noradrenalin reuptake inhibitory effects. The first drug put on the market as SSRI was zimelidine. Examples of other SSRIs that have then be launched or are under development include fluoxetine, fluvoxamine, citalopram, sertraline and paroxetine.

Although such SSRIs are widely used as therapeutic drugs for depression, it has been pointed out that they still have some problems. Examples of typical problems include: even SSRI does not exert a sufficient therapeutic effect on refractory depression patients, who occupy approximately ⅓ of all depression patients; and a period as long as 3 to 8 weeks is required for SSRI to exhibit its sufficient antidepressant effect. Thus, SSRI is slow in exhibiting its antidepressant effect, whereas its adverse reaction can occur immediately. Specifically, there arises the problem of a vulnerable period during which patients experience only adverse reaction without obtaining the therapeutic effect of the drug. Therefore, treating physicians are often heavily burdened with persuasion to convince their patients to continue medication with the same drugs even during this period. Furthermore, patients who are at risk of committing suicide restore their initiatives before experiencing sufficient improvement in the depressive symptoms due to the slow onset of the antidepressant effect. Therefore, there occurs the risk of suicide, the need for frequent hospitalization, or the like. Thus, it has been desired to develop an antidepressant that quickly exhibits an antidepressant effect.

The reason why SSRI requires a period as long as several weeks for exhibiting its antidepressant effect has been considered as follows:

SSRI inhibits acute serotonin reuptake in serotonin turnover. This inhibitory effect occurs in the nerve endings of serotonergic neurons. As a result, serotonin-mediated neurotransmission is potentiated, resulting in the onset of an antidepressant effect. However, this inhibitory effect also occurs in serotonergic neuronal cells or dendrites present in the raphe nuclei. Thus, in the raphe nuclei, the inhibited spontaneous firing (negative feedback reaction) of the serotonergic neurons via serotonin 1A autoreceptors is unintentionally potentiated. As a result, at the initial stage after administration of SSRI, the whole neurotransmission in the serotonergic neurons is not potentiated as much as expected. On the other hand, serotonin 1A autoreceptors on the serotonergic neuronal cells or dendrites of the raphe nuclei are desensitized as medication with SSRI is continued for several weeks. Thus, the negative feedback reaction disappears. As a result, the enhanced activities of the serotonergic neurons and the inhibited serotonin uptake in the nerve endings function in collaboration to potentiate serotonin neurotransmission, resulting in the onset of a sufficient antidepressant effect.

Thus, combined use with a serotonin 1A receptor antagonist blocks serotonin 1A autoreceptors to terminate the negative feedback reaction of serotonin. Alternatively, combined use with a serotonin 1A receptor agonist aggressively stimulates serotonin 1A autoreceptors to shorten the period up to desensitization. As a result, the period up to the onset of the effect of SSRI can be shortened or its antidepressant effect can be enhanced. In fact, it has been reported that the combined use of SSRI with pindolol having high affinity for serotonin 1A receptors enhances the effect of the serotonin reuptake inhibitor in depression patients and shortens the period up to the onset of its effect (Non Patent Literature 1).

When patients take drugs, fewer numbers or types of the drugs are desirable. Thus, based on the findings described above, it is considered that a compound having both of a serotonin reuptake inhibitory effect and affinity for serotonin 1A receptors can serve, in itself without being used in combination with other drugs, as a novel antidepressant that has a strong antidepressant effect and requires a shortened period for exhibiting its effect. It has been desired to develop such a compound as a drug.

A benzylpiperidine derivative having a substituted benzyl group at 4-position and a substituted phenylethyl group at 1-position has previously been reported (see e.g., Patent Literature 1) as the compound having both of a serotonin reuptake inhibitory effect and affinity for serotonin 1A receptors. Specifically, the literature discloses a serotonin reuptake inhibitor comprising cyclic amine represented by a formula (A), etc., as an active ingredient:

[Formula 1]

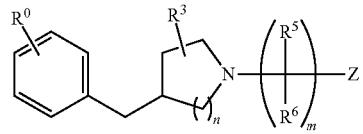

(A)

wherein $R^0$ represents a hydrogen atom, a halogen atom, an alkyl group, a substituted alkoxy group, or the like, and a plurality of $R^0$ moieties exist independently; $R^3$ represents a hydrogen atom or the like; n represents an integer of 2 or the like; m represents an integer of 2 or the like; $R^5$ and $R^6$ each independently represent a hydrogen atom or the like; and Z represents a substituted aryl group or the like. The literature further discloses that these serotonin reuptake inhibitors have a serotonin 1A antagonistic effect.

Meanwhile, a compound having a substituted benzyl group at 4-position of piperidine has been reported in a plurality of literatures. Examples thereof include a literature that discloses a cyclic amine derivative acting as a therapeutic drug for cerebral vascular disorder (see Patent Literature 2) and a literature that discloses 4-substituted piperidine acting as an NMDA receptor antagonist (see Patent Literature 3).

Furthermore, a compound having a substituted phenylethyl group at 1-position of piperidine has also been reported in several literatures. An indole derivative having a piperidine ring having a cyclic ketone structure as a substituent on a phenylethyl group has been reported as a 5-HT1A antagonist (see e.g., Patent Literature 4). These indole derivatives differ in skeleton from benzylpiperidine compounds having a substituted benzyl group at 4-position of piperidine. Moreover, these indole derivatives have not been reported to also have a serotonin reuptake inhibitory effect.

Any of these patent literatures neither specifically disclose nor suggest a benzylpiperidine compound that has, at 4-position of piperidine, a benzyl group having an oxygen atom at 3-position of the benzene ring moiety and further has, at 1-position of piperidine, a 2-(chroman-6-yl)ethyl group or a 2-(4H-chromen-6-yl)ethyl group substituted by a hydroxy group and/or an oxo group.

Moreover, most of antidepressants such as tricyclic antidepressants (TCAs) or SSRIs are known to have a strong inhibitory effect on CYP2D6, which is an enzyme involved in drug metabolism and is a human cytochrome P450 molecular species. On the other hand, it is also known that most of therapeutic agents for psychiatric disease that can be used in combination with TCA or SSRI in the treatment of depression or anxiety symptoms are metabolized by CYP2D6. Thus, in the combined use of these drugs, the metabolism of the drug is inhibited on the basis of the CYP2D6 inhibitory effect of the other drug to thereby increase the serum concentration of the former drug. As a result, severe adverse reaction may occur. Thus, an antidepressant having a weaker CYP2D6 inhibitory effect has a smaller drug interaction with the combined therapeutic drug for psychiatric disease, which is metabolized by CYP2D6. Thus, such an antidepressant can be expected to serve as a highly safe drug, and it has been desired to develop it.

Furthermore, CYP2D6 is known to greatly vary in its enzyme activity between individuals due to genetic polymorphisms. Drugs that are metabolized at high rates by CYP2D6 greatly differ in in-vivo drug concentration between individuals and are at high risk of having a much higher serum drug concentration in a poor metabolizer (PM) than in an extensive metabolizer (EM). Moreover, such drugs are also in danger of exhibiting a stronger drug interaction with drugs inhibiting CYP2D6 or drugs undergoing metabolism by CYP2D6. Thus, the lower contribution ratio of CYP2D6 in drug metabolism results in the smaller pharmacokinetic influence of CYP2D6 attributed to genetic polymorphisms. Thus, such a drug can be expected to serve as a highly safe drug, and it has also been desired to develop it.

CITATION LIST

Patent Literature

Patent Literature 1: U.S. Pat. No. 6,787,560
Patent Literature 2: Pamphlet of International Publication No. WO 88/02365
Patent Literature 3: Pamphlet of International Publication No. WO 97/23216
Patent Literature 4: Pamphlet of International Publication No. WO 2005/108389

Non Patent Literature

Non Patent Literature 1: Arch, Gen. Psychiatry, (1994), 51, 248-251

SUMMARY OF INVENTION

Technical Problem

An object of the present invention is to provide a novel serotonin reuptake inhibitor also having affinity for serotonin 1A receptors. Such a serotonin reuptake inhibitor is expected to serve as a therapeutic drug for, for example, depression or anxiety (anxiety disorder). Thus, an object of the present invention is to provide a drug that is excellent in therapeutic effect and further has high safety. A specific object of the present invention is to provide a drug that has an improved inhibitory activity against human serotonin reuptake, has affinity for serotonin 1A receptors, and has a weaker inhibitory effect on CYP2D6, a human cytochrome P450 molecular species, or undergoes drug metabolism in humans to which CYP2D6 makes a small contribution.

Solution to Problem

The present inventors have conducted diligent studies to attain the object and consequently found that a benzylpiperidine compound that is characterized in terms of its chemical structure by having a substituted benzyl group in which 3-position of the benzene ring moiety is substituted by a hydroxy group, a 2-methoxyethoxy group or a 2-hydroxyethoxy group, and having, at 1-position of piperidine, a 2-(chroman-6-yl)ethyl group or a 2-(4H-chromen-6-yl)ethyl group substituted by a hydroxy group and/or an oxo group, or a pharmaceutically acceptable salt thereof has both of a high inhibitory effect on human serotonin reuptake and binding affinity for human 5-HT1A receptors; and, in addition, the compound or the salt has weaker CYP2D6 inhibition and undergoes metabolism to which CYP2D6 makes a small contribution. Based on these findings, the present invention has been completed.

The present invention relates to a benzylpiperidine compound or a pharmaceutically acceptable salt thereof that is useful as a serotonin reuptake inhibitor according to the following [1] to [11]. Specifically, the present invention is as follows:

[1]

A compound represented by a formula (1) or a pharmaceutically acceptable salt thereof:

[Formula 2]

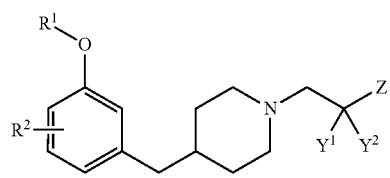

(1)

wherein R¹ represents a hydrogen atom or a group represented by a formula (2):

[Formula 3]

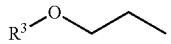

(2)

wherein R³ represents a hydrogen atom or a methyl group;

R² represents a chlorine atom bonded at the p-position, a bromine atom bonded at the p-position, a methyl group bonded at the p-position, a chlorine atom bonded at the m-position or a bromine atom bonded at the m-position, with respect to a methylene group bonded to a piperidine ring;

Y¹ represents a hydrogen atom, and Y² represents a hydrogen atom or a hydroxy group or Y¹ and Y² together represent an oxo group; and Z represents a group represented by a formula (3-1-1), (3-1-2), (3-2-1), (3-2-2), (3-3-1), (3-3-2), (3-4-1) or (3-4-2):

[Formula 4]

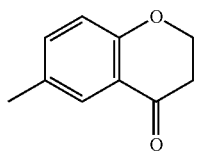 (3-1-1)

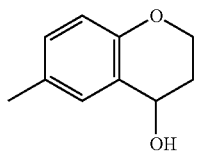 (3-2-1)

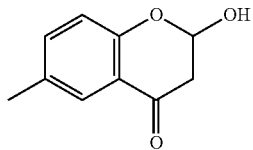 (3-3-1)

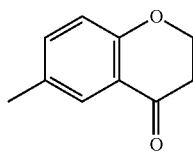 (3-4-1)

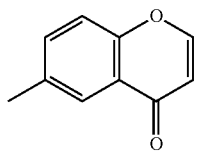 (3-1-2)

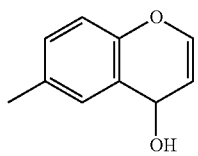 (3-2-2)

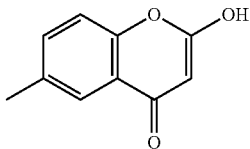 (3-3-2)

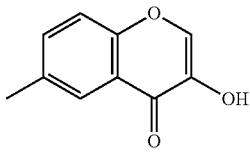 (3-4-2)

wherein when R¹ represents a group represented by the formula (2) and each of Y¹ and Y² represents a hydrogen atom, Z represents a group selected from the group consisting of the formulas (3-1-2), (3-2-1), (3-2-2), (3-3-1), (3-3-2), (3-4-1) and (3-4-2).

[2] The compound according to [1] or a pharmaceutically acceptable salt thereof, wherein R² is a bromine atom bonded at the p-position.

[3] The compound according to [1] or [2] or a pharmaceutically acceptable salt thereof, wherein Z is a group represented by the formula (3-1-1), (3-2-1), (3-3-1) or (3-4-1).

[4] The compound according to [1] or [2] or a pharmaceutically acceptable salt thereof, wherein Z is a group represented by the formula (3-1-1), (3-2-1), (3-4-1) or (3-4-2).

[5] The compound according to any of [1] to [4] or a pharmaceutically acceptable salt thereof, wherein each of Y¹ and Y² is a hydrogen atom.

[6] The compound according to any of [1] to [4] or a pharmaceutically acceptable salt thereof, wherein Y¹ is a hydrogen atom, and Y² is a hydroxy group.

[7] The compound according to [1] or a pharmaceutically acceptable salt thereof, wherein the compound represented by the formula (1) is a compound selected from the group consisting of the following compounds (01) to (11):

(01) 6-(2-{4-[4-Bromo-3-(2-methoxyethoxy)benzyl]piperidin-1-yl}ethyl)-3-hydroxy-2,3-dihydro-4H-chromen-4-one,

(02) 6-(2-{4-[4-Bromo-3-(2-hydroxyethoxy)benzyl]piperidin-1-yl}ethyl)-3-hydroxy-2,3-dihydro-4H-chromen-4-one,

(03) 6-{2-[4-(4-Bromo-3-hydroxybenzyl)piperidin-1-yl]ethyl}-3-hydroxy-2,3-dihydro-4H-chromen-4-one,

(04) 6-(2-{4-[4-Bromo-3-(2-methoxyethoxy)benzyl]piperidin-1-yl}ethyl)-4H-chromen-4-one,

(05) 6-(2-{4-[4-Bromo-3-(2-hydroxyethoxy)benzyl]piperidin-1-yl}ethyl)-4H-chromen-4-one,

(06) 6-{2-[4-(4-Bromo-3-hydroxybenzyl)piperidin-1-yl]ethyl}-4H-chromen-4-one,

(07) 6-(2-{4-[4-Bromo-3-(2-methoxyethoxy)benzyl]piperidin-1-yl}-1-hydroxyethyl)-2,3-dihydro-4H-chromen-4-one,

(08) 6-(2-{4-[4-Bromo-3-(2-methoxyethoxy)benzyl]piperidin-1-yl}ethyl)-3,4-dihydro-2H-chromen-4-ol,

(09) 6-(2-{4-[4-Bromo-3-(2-methoxyethoxy)benzyl]piperidin-1-yl}ethyl)-3-hydroxy-4H-chromen-4-one,

(10) 6-(2-{4-[4-Bromo-3-(2-hydroxyethoxy)benzyl]piperidin-1-yl}ethyl)-3-hydroxy-4H-chromen-4-one, and

(11) (−)-6-(2-{4-[4-Bromo-3-(2-methoxyethoxy)benzyl]piperidin-1-yl}ethyl)-3,4-dihydro-2H-chromen-4-ol.

[8]
The compound according to [1] or a pharmaceutically acceptable salt thereof, wherein $R^2$ is a bromine atom bonded at the p-position, Z is a group represented by the formula (3-2-1), (3-3-1) or (3-4-1), and each of $Y^1$ and $Y^2$ is a hydrogen atom.

[9]
The compound according to [1] or a pharmaceutically acceptable salt thereof, wherein $R^2$ represents a bromine atom bonded at the p-position, Z represents a group represented by the formula (3-2-1), (3-3-1) or (3-4-1), each of $Y^1$ and $Y^2$ represents a hydrogen atom, and $R^1$ represents a group represented by the formula (2).

[10]
The compound according to [1] or a pharmaceutically acceptable salt thereof, wherein $R^2$ is a bromine atom bonded at the p-position, Z is a group represented by the formula (3-2-1), (3-4-1) or (3-4-2), and each of $Y^1$ and $Y^2$ is a hydrogen atom.

[11]
The compound according to [1] or a pharmaceutically acceptable salt thereof, wherein $R^2$ represents a bromine atom bonded at the p-position, Z represents a group represented by the formula (3-2-1), (3-4-1) or (3-4-2), each of $Y^1$ and $Y^2$ represents a hydrogen atom, and $R^1$ represents a group represented by the formula (2).

[12]
A pharmaceutical composition comprising a compound according to any of [1] to [11] or a pharmaceutically acceptable salt thereof as an active ingredient.

[13]
A serotonin reuptake inhibitor comprising a compound according to any of [1] to [11] or a pharmaceutically acceptable salt thereof as an active ingredient.

[14]
An antidepressant or an anxiolytic drug comprising a compound according to any of [1] to [11] or a pharmaceutically acceptable salt thereof as an active ingredient.

Advantageous Effects of Invention

The present invention can provide a benzylpiperidine compound or a pharmaceutically acceptable salt thereof useful as a serotonin reuptake inhibitor that can serve as a therapeutic drug for depression or the like. Specifically, the present invention can provide a benzylpiperidine compound or a pharmaceutically acceptable salt thereof that has a high inhibitory activity against human serotonin reuptake and binding affinity for human 5-HT1A receptors and has weaker CYP2D6 inhibition or undergoes metabolism to which CYP2D6 makes a small contribution.

DESCRIPTION OF EMBODIMENTS

Hereinafter, the present invention will be described more specifically.

A benzylpiperidine compound of the present invention represented by the formula (1) (hereinafter, also referred to as a "compound of the present invention") is characterized in terms of its chemical structure by having a substituted benzyl group in which 3-position of the benzene ring moiety is substituted by a hydroxy group, a 2-methoxyethoxy group or a 2-hydroxyethoxy group, and having, at 1-position of piperidine, a 2-(chroman-6-yl)ethyl group or a 2-(4H-chromen-6-yl)ethyl group substituted by a hydroxy group and/or an oxo group.

When the compound of the present invention has asymmetric carbon (e.g., when $Y^1$ is a hydrogen atom and $Y^2$ is a hydroxy group or when Z is a group represented by the formula (3-2-1), (3-2-2), (3-3-1) or (3-4-1)), the compound of the present invention encompasses all compounds as R or S forms based on each asymmetric carbon and racemates.

In the present invention, the term "substituted sulfonyloxy group" means a sulfonyloxy group substituted by an alkyl group or an optionally substituted phenyl group. In this context, examples of the alkyl group include linear or branched alkyl groups having 1 to 6 carbon atoms and specifically include a methyl group, an ethyl group, a propyl group, an isopropyl group, a butyl group, an isobutyl group, a sec-butyl group, a tert-butyl group, a pentyl group, a hexyl group and a trifluoromethyl group. Examples of the substituent in the optionally substituted phenyl group include halogen atoms (in this context, examples of the halogen atoms include a fluorine atom, a chlorine atom, a bromine atom and an iodine atom), alkyl groups (in this context, the alkyl groups refer to linear or branched alkyl groups having 1 to 6 carbon atoms, and specific examples thereof include a methyl group, an ethyl group, a propyl group, an isopropyl group, a butyl group, an isobutyl group, a sec-butyl group, a tert-butyl group, a pentyl group and a hexyl group), a trifluoromethyl group, a cyano group, a nitro group or alkoxy groups (in this context, the alkoxy groups refer to linear or branched alkoxy groups having 1 to 6 carbon atoms, and specific examples thereof include a methoxy group, an ethoxy group, a propoxy group, an isopropoxy group, a butoxy group, an isobutoxy group, a sec-butoxy group, a tert-butoxy group, a pentyloxy group and a hexyloxy group). Preferable examples of the substituted sulfonyloxy group include a methanesulfonyloxy group, a benzenesulfonyloxy group and a p-toluenesulfonyloxy group. More preferable examples of the substituted sulfonyloxy group include a benzenesulfonyloxy group and a p-toluenesulfonyloxy group.

In the formula (1), preferable examples of $R^1$ include a 2-methoxyethyl group and a 2-hydroxyethyl group. More preferable examples thereof include a 2-methoxyethyl group.

In the formula (1), preferable examples of $R^2$ include a chlorine atom bonded at the p-position, a bromine atom bonded at the p-position and a methyl group bonded at the p-position, with respect to the methylene group. More preferable examples thereof include a bromine atom bonded at the p-position with respect to the methylene group. Specific examples of the compound of the formula (1) wherein $R^2$ is a "bromine atom bonded at the p-position" include compounds of a formula (5-1) described later in Example 1.

In the formula (1), preferable examples of $Y^1$ and $Y^2$ include a combination in which each of $Y^1$ and $Y^2$ is a hydrogen atom and a combination in which $Y^1$ is a hydrogen atom and $Y^2$ is a hydroxy group. More preferable examples thereof include a combination in which each of $Y^1$ and $Y^2$ is a hydrogen atom.

In the formula (1), preferable examples of Z include groups represented by the formulas (3-1-1), (3-2-1) and (3-4-1). More preferable examples of Z include a group represented by the formula (3-4-1). Moreover, other preferable examples of Z include groups represented by the formulas (3-2-1), (3-3-1) and (3-4-1). Furthermore, other preferable examples of Z include groups represented by the formulas (3-2-1), (3-4-1) and (3-4-2).

The compound of the present invention can be produced from compounds known in the art by appropriately combining methods shown below in Production Methods 1 to 5, methods similar to the production methods described below, or synthetic methods well known by those skilled in the art. Starting compounds (11), (12), (13), (20), (22) and (25) can also be produced by appropriately combining methods described later in Examples, methods similar to the methods of Examples, and synthetic methods well known by those skilled in the art.

Moreover, in the present specification, the following abbreviations may be used for simplifying the description:
Ac: Acetyl group
Boc: tert-Butoxycarbonyl group
Me: Methyl group
t-Bu: tert-Butyl group
Ph: Phenyl group
Ms: Methanesulfonyl group
Ts: p-Toluenesulfonyl group
p: para (e.g., "p-Br" means a bromine atom bonded at the para-position.)
m: meta (e.g., "m-Br" means a bromine atom bonded at the meta-position.)

[Production Method 1: Method for Producing Compound (1)]

The compound represented by the formula (1) or a salt thereof can also be produced by, for example, the following method:

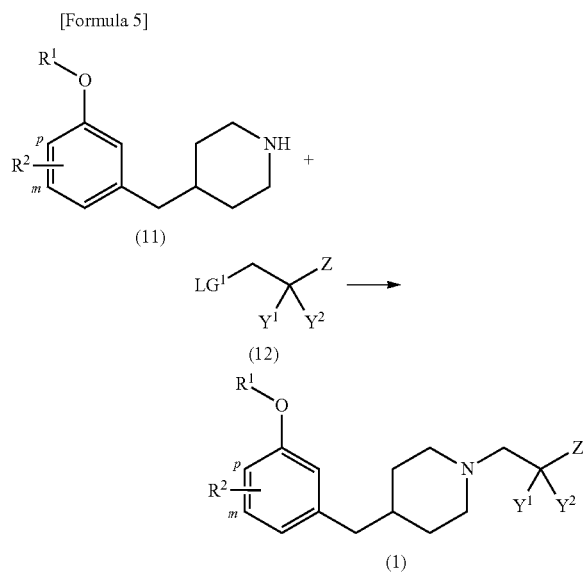

wherein $R^1$, $R^2$, Z, $Y^1$ and $Y^2$ are as defined above (provided that when $R^1$ represents a hydrogen atom or a 2-hydroxyethyl group, the hydroxy group may be protected with a protective group such as a methoxymethyl group or a benzyl group, if necessary); and $LG^1$ represents an iodine atom, a bromine atom, a chlorine atom, a substituted sulfonyloxy group, or the like.

The compound (1) of interest or a salt thereof can be obtained by reacting a compound (11) or a salt thereof with a compound (12). The reaction can be performed by reacting these compounds in an appropriate inert solvent at a temperature ranging from approximately −20° C. to the boiling point of the solvent used for 10 minutes to 48 hours, if necessary in the presence of a base and if necessary in the presence of a phase-transfer catalyst.

Examples of the base include: organic bases such as triethylamine, diisopropylethylamine and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide and sodium hydride; or metal alkoxides such as sodium methoxide and potassium tert-butoxide.

Examples of the phase-transfer catalyst include tetrabutylammonium hydrogen sulfate.

Examples of the inert solvent include: halogenated hydrocarbon solvents such as chloroform and dichloromethane; aromatic hydrocarbon solvents such as benzene and toluene; ether solvents such as diethyl ether, tetrahydrofuran (THF) and 1,4-dioxane; lower alcoholic solvents such as methanol, ethanol and isopropanol; or aprotic polar solvents such as acetonitrile, dimethylformamide, N-methyl-2-pyrrolidinone and dimethyl sulfoxide (DMSO); or mixed solvents thereof. More preferable examples of the solvent include acetonitrile.

The leaving group $LG^1$ is preferably a halogen group (e.g., a bromine group) or a substituted sulfonyloxy group, more preferably a p-toluenesulfonyloxy group or a benzenesulfonyloxy group.

When the hydroxy group is protected, this protected hydroxy group can be converted to a hydroxy group by a usual deprotection reaction. For example, when the protective group is a methoxymethyl group, the deprotection can be performed by treatment with an inorganic acid (e.g., hydrochloric acid or sulfuric acid) or an organic acid (e.g., p-toluenesulfonic acid or trifluoroacetic acid) in an appropriate inert solvent at a temperature ranging from approximately −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, tetrahydrofuran (THF) and 1,4-dioxane; lower alcoholic solvents such as methanol, ethanol and isopropanol; or aprotic polar solvents such as acetonitrile, dimethylformamide, N-methyl-2-pyrrolidinone and dimethyl sulfoxide (DMSO); or mixed solvents thereof.

[Production Method 2: Method for Producing Compound (1-1)]

A compound (1-1), which is a compound represented by the formula (1) wherein $Y^1$ represents a hydrogen atom and $Y^2$ represents a hydroxy group, can also be produced by the following method:

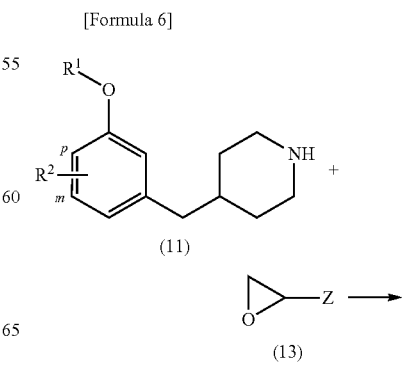

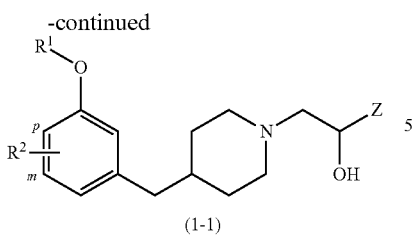

(1-1)

wherein $R^1$, $R^2$ and Z are as defined above.

The compound (1-1) of interest or a salt thereof can be obtained by reacting the compound (11) or a salt thereof with a compound (13) in an appropriate inert solvent at a temperature ranging from approximately −20° C. to the boiling point of the solvent used for 10 minutes to 48 hours, if necessary in the presence of an acid or a base. Examples of the inert solvent include: halogenated hydrocarbon solvents such as chloroform and dichloromethane; aromatic hydrocarbon solvents such as benzene and toluene; ether solvents such as diethyl ether, THF and 1,4-dioxane; lower alcoholic solvents such as methanol, ethanol and isopropanol; or aprotic polar solvents such as acetonitrile, dimethylformamide, N-methyl-2-pyrrolidinone and DMSO; or mixed solvents thereof. Examples of the base include: organic bases such as triethylamine, diisopropylethylamine and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide and sodium hydride; or metal alkoxides such as sodium methoxide and potassium tert-butoxide. Examples of the acid include: inorganic acids such as hydrochloric acid and sulfuric acid; or organic acids such as p-toluenesulfonic acid and trifluoroacetic acid.

[Production Method 3: Method for Producing Compound (1-2)]

A compound (1-2), which is a compound represented by the formula (1) wherein each of $Y^1$ and $Y^2$ represents a hydrogen atom, and Z represents a group represented by a formula (3-4-1):

[Formula 7]

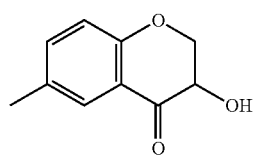

(3-4-1)

can also be produced by the following method:

[Formula 8]

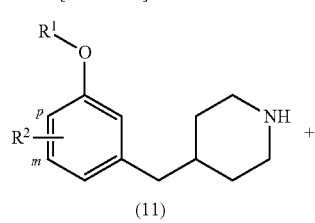

(11)

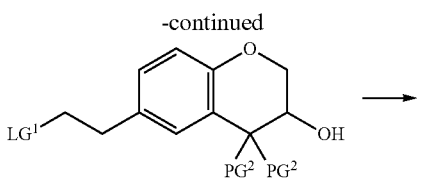

(14)

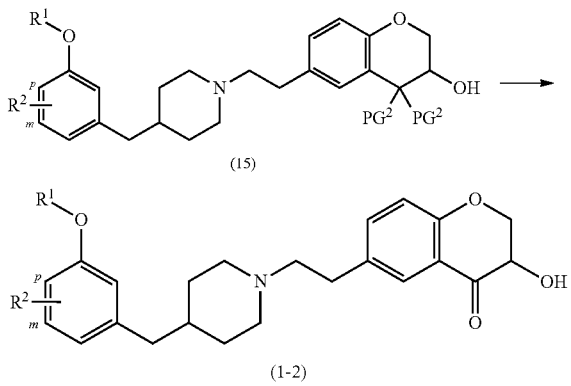

(15)

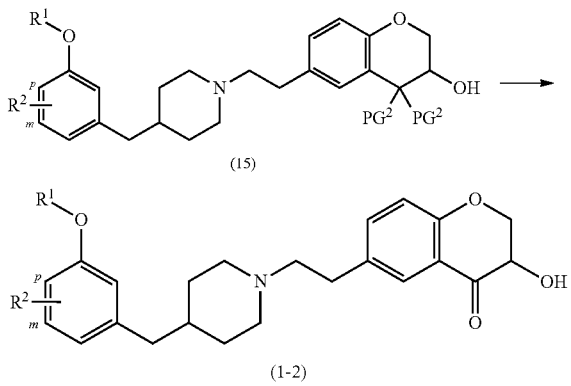

(1-2)

wherein $R^1$, $R^2$ and $LG^1$ are as defined above; and $PG^2$ represents a lower alkoxy group, for example, a methoxy group or an ethoxy group.

The compound (1-2) of interest or a salt thereof can be obtained by reacting the compound (11) or a salt thereof with a compound (14) in the same way as Production Method 1, and deprotecting the thus-obtained compound (15) by an appropriate method. The deprotection can be performed by treating the compound (15) with an inorganic acid (e.g., hydrochloric acid or sulfuric acid) or an organic acid (e.g., p-toluenesulfonic acid, acetic acid or trifluoroacetic acid) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; lower alcoholic solvents such as methanol, ethanol and isopropanol; aprotic polar solvents such as acetonitrile, dimethylformamide, N-methyl-2-pyrrolidinone and DMSO; or water; or mixed solvents thereof.

[Production Method 4: Method for Producing Compound (1-3)]

A compound (1-3), which is a compound represented by the formula (1) wherein each of $Y^1$ and $Y^2$ represents a hydrogen atom, and Z represents a group represented by a formula (3-3-1):

[Formula 9]

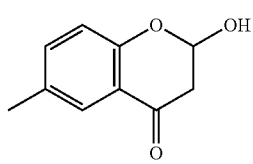

(3-3-1)

can also be produced by the following method:

[Formula 10]

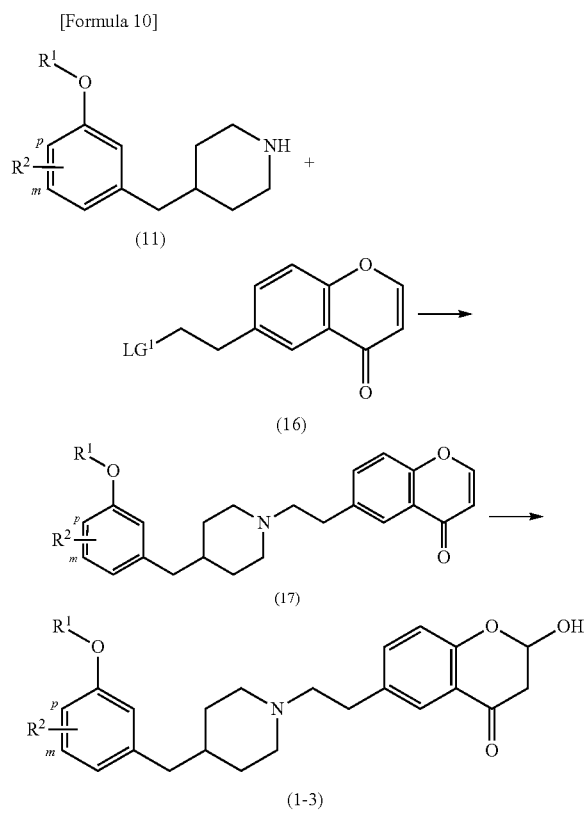

wherein $R^1$, $R^2$ and $LG^1$ are as defined above.

A compound (17) can be obtained by reacting the compound (11) or a salt thereof with a compound (16) in the same way as Production Method 1. The compound (1-3) can be obtained by reacting the compound (17) with sodium hydroxide, potassium hydroxide, or the like in an appropriate inert solvent at a temperature ranging from approximately −20° C. to the boiling point of the solvent used for 10 minutes to 48 hours. Examples of the appropriate inert solvent include: ether solvents such as THE, 1,4-dioxane and 1,2-dimethoxyethane; lower alcoholic solvents such as methanol, ethanol and isopropanol; aprotic polar solvents such as acetonitrile, dimethylformamide, N-methyl-2-pyrrolidinone and DMSO; or water; or mixed solvents thereof.

[Production Method 5: Method for Producing Compound (1-4)]

A compound (1-4), which is a compound represented by the formula (1) wherein each of $Y^1$ and $Y^2$ represents a hydrogen atom, and Z represents a group represented by a formula (3-2-1):

[Formula 11]

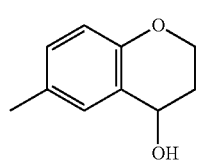

(3-2-1)

can also be produced by the following method:

[Formula 12]

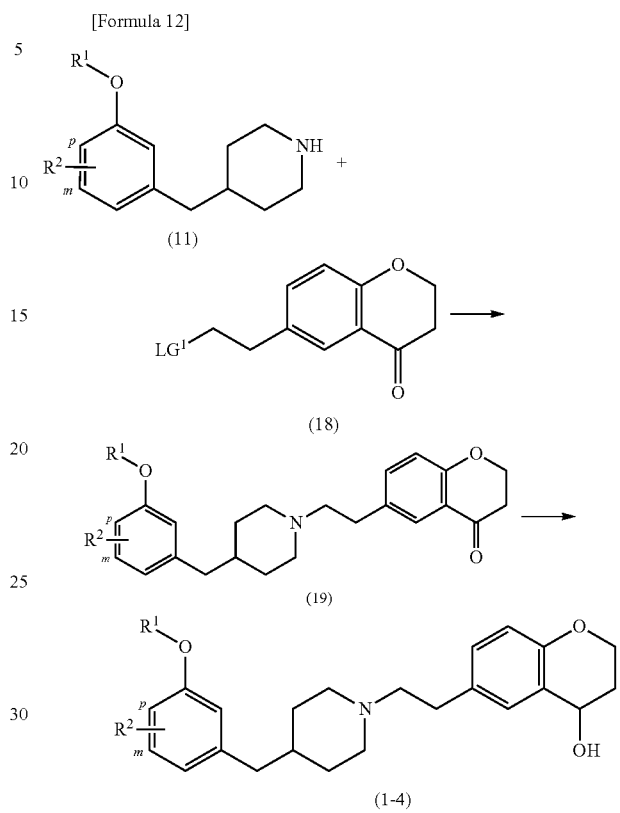

wherein $R^1$, $R^2$ and $LG^1$ are as defined above.

A compound (19) can be obtained by reacting the compound (11) or a salt thereof with a compound (18) in the same way as Production Method 1. The compound (1-4) of interest can be produced by reacting the compound (19) with an appropriate reducing agent in an appropriate inert solvent at a temperature ranging from approximately −20° C. to the boiling point of the solvent used. Examples of the appropriate inert solvent include: ether solvents such as THF, 1,4-dioxane and 1,2-dimethoxyethane; lower alcoholic solvents such as methanol, ethanol and isopropanol; or water; or mixed solvents thereof. Examples of the appropriate reducing agent include sodium borohydride, lithium borohydride, sodium cyanoborohydride and sodium triacetoxyborohydride.

[Production Method 6: Method for Producing Compound (1-5)]

A compound (1-5), which is a compound represented by the formula (1) wherein each of $Y^1$ and $Y^2$ represents a hydrogen atom, and Z represents a group represented by a formula (3-2-2):

[Formula 13]

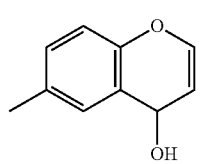

(3-2-2)

can also be produced by the following method:

[Formula 14]

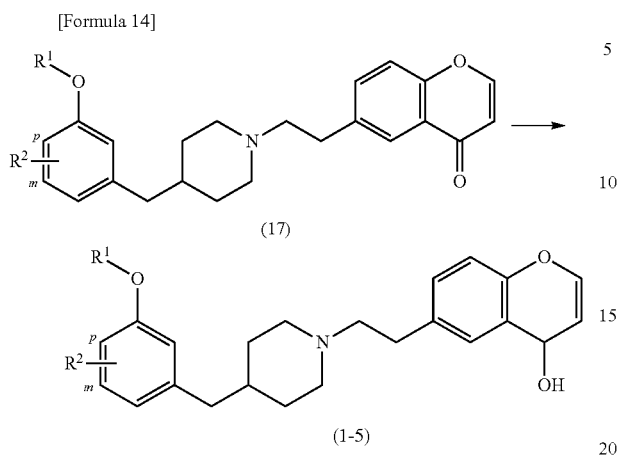

wherein $R^1$ and $R^2$ are as defined above.

The compound (1-5) can be obtained by subjecting the compound (17) obtained in Production Method 4 to a reduction reaction in the same way as Production Method 5.

[Production Method 7: Method for Producing Compound (11)]

The compound (11) or the salt thereof used as a starting material in Production Method 1, etc., can also be produced by the following method, for example, with reference to a literature such as U.S. Pat. No. 6,787,560:

[Formula 15]

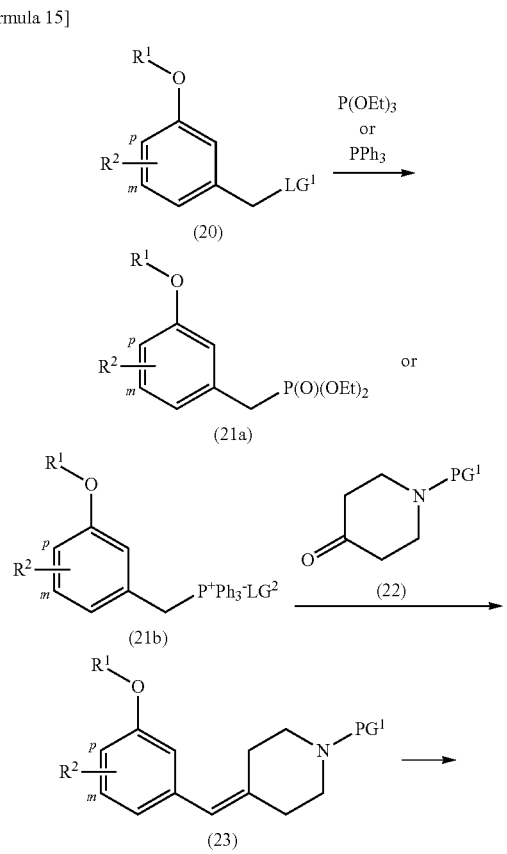

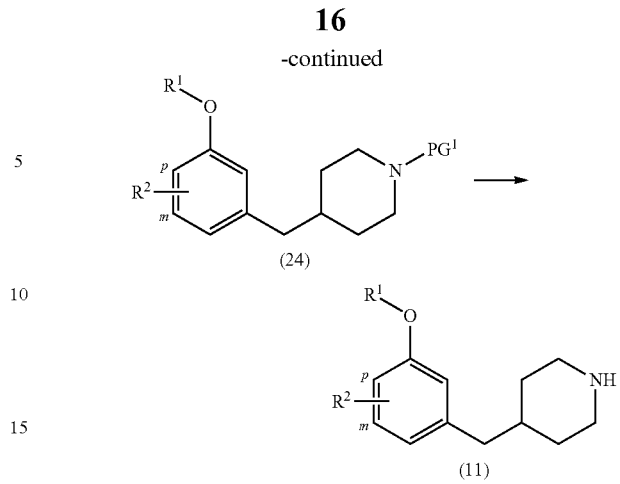

wherein $R^1$ and $R^2$ are as defined above (provided that when $R^1$ represents a hydrogen atom or a 2-hydroxyethyl group, the hydroxy group may be protected with a protective group such as a methoxymethyl group or a benzyl group, if necessary); $PG^1$ represents a protective group for the nitrogen atom; and $LG^2$ represents a leaving group. Examples of the protective group $PG^1$ for the nitrogen atom include alkyloxycarbonyl groups such as a t-butyloxycarbonyl group and a 9-fluorenylmethyloxycarbonyl group. Examples of the leaving group $LG^2$ include: halogen atoms such as a chlorine atom, a bromine atom and an iodine atom; or substituted sulfonyloxy groups such as a p-toluenesulfonyloxy group and a methanesulfonyloxy group.

A compound (20) is converted to a phosphonic acid ester (21a) or a phosphonium salt (21b). This conversion to the phosphonic acid ester (21a) can be performed by reacting the compound (20) with triethyl phosphite without a solvent or in an inert solvent at a temperature from ice cooling to the boiling point of the solvent used or triethyl phosphite for 1 hour to 3 days. The conversion to the phosphonium salt (21b) can be performed by reacting the compound (20) with triphenylphosphine in an inert solvent at a temperature from ice cooling to the boiling point of the solvent used for 1 hour to 3 days.

This phosphonic acid ester (21a) or phosphonium salt (21b) can be converted to a compound (23) by reaction with a ketone (22) in an appropriate inert solvent at a temperature from approximately −20° C. to the boiling point of the solvent used for 10 minutes to 48 hours in the presence of a base.

Examples of the base include: organic bases such as triethylamine and pyridine; inorganic bases such as potassium carbonate, potassium hydroxide and sodium hydride; or metal alkoxides such as sodium methoxide and potassium tert-butoxide.

Examples of the inert solvents in the step of converting a compound (20) to a phosphonic acid ester (21a) or a phosphonium salt (21b) and in the step of further converting the compound to a compound (23) include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; lower alcoholic solvents such as methanol, ethanol and isopropanol; or aprotic polar solvents such as acetonitrile, dimethylformamide, N-methyl-2-pyrrolidinone and DMSO; or mixed solvents thereof.

The compound (23) can be converted to a compound (24) by catalytic hydrogenation. When $R^2$ represents a bromine atom bonded at the p-position or a bromine atom bonded at the m-position, this reduction reaction can be performed by reaction at 0° C. to 50° C. in an appropriate inert solvent at ambient pressure or in a pressurized hydrogen atmosphere using a rhodium catalyst (e.g., rhodium carbon), a platinum catalyst (e.g., platinum carbon), a ruthenium catalyst (e.g., ruthenium carbon) or palladium chloride, or the like as a catalyst. Examples of the appropriate inert solvent include: aromatic hydrocarbon solvents such as benzene and toluene; ether solvents such as diethyl ether, THF, 1,4-dioxane and 1,2-dimethoxyethane; lower alcoholic solvents such as methanol, ethanol and isopropanol; aprotic polar solvents such as dimethylformamide, N-methyl-2-pyrrolidinone and DMSO; or ethyl acetate; or mixed solvents thereof More preferable examples of the catalyst include rhodium carbon and platinum carbon. Moreover, in this case, more preferable examples of the solvent include ethyl acetate. When $R^2$ is a chlorine atom or a methyl group bonded at the p-position or a chlorine atom bonded at the m-position, the compound (23) can be converted to the compound (24) by a usual catalytic reduction reaction using palladium carbon, palladium hydroxide, or the like, in addition to the conditions described above.

The compound (11) of interest can be obtained by deprotecting the compound (24) by a routine method. When the protective group is a t-butyloxycarbonyl group, the deprotection can be performed by treatment with an inorganic acid (e.g., hydrochloric acid or sulfuric acid) or an organic acid (e.g., trifluoroacetic acid) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; lower alcoholic solvents such as methanol, ethanol and isopropanol; or aprotic polar solvents such as acetonitrile, dimethylformamide, N-methyl-2-pyrrolidinone and DMSO; or mixed solvents thereof When the protective group is a 9-fluorenylmethyloxycarbonyl group, the deprotection can be performed by treatment with an organic base (e.g., pyrrolidine, piperidine, morpholine, triethylamine, or diisopropylethylamine) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; lower alcoholic solvents such as methanol, ethanol and isopropanol; or aprotic polar solvents such as acetonitrile, dimethylformamide, N-methyl-2-pyrrolidinone and DMSO; or mixed solvents thereof. When the hydroxy group is protected with a protective group, this protected group can be converted to a hydroxy group by a usual deprotection reaction.

[Production Method 8: Method for Producing Compound (18)]

The compound (18), which is a compound (12) used as a starting material in Production Method 1 wherein each of $Y^1$ and $Y^2$ represents a hydrogen atom and Z represents a group represented by a formula (3-1-1):

[Formula 16]

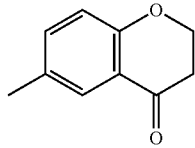

(3-1-1)

can also be produced by the following production method:

[Formula 17]

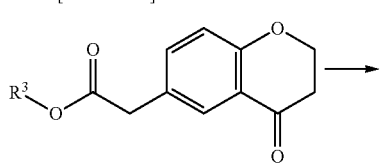

(25)

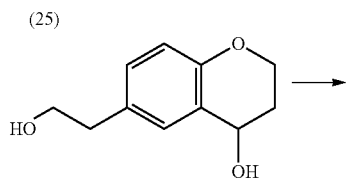

(26)

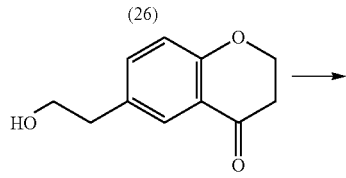

(27)

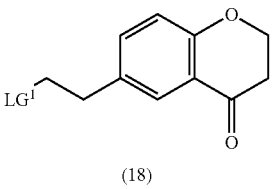

(18)

wherein $LG^1$ is as defined above; and $R^3$ represents a hydrogen atom or an alkyl group. Examples of the alkyl group include linear or branched alkyl groups having 1 to 6 carbon atoms and can specifically include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group and a hexyl group.

A compound (26) can be obtained by reacting a compound (25) with an appropriate reducing agent (e.g., lithium aluminum hydride, lithium borohydride, sodium borohydride or diborane) in an appropriate inert solvent (e.g. an ether solvent such as diethyl ether, THF or 1,4-dioxane) at a temperature from −20° C. to the boiling point of the solvent used for 10 minutes to 48 hours.

A compound (27) can be obtained by oxidizing the compound (26) with an oxidizing agent (e.g., manganese dioxide) in an appropriate inert solvent. Examples of the appropriate inert solvent include: halogenated hydrocarbon solvents such as chloroform and dichloromethane; ether solvents such as diethyl ether, THF, 1,4-dioxane and 1,2-dimethoxyethane; or aprotic polar solvents such as acetonitrile, dimethylformamide, N-methyl-2-pyrrolidinone and DMSO; or mixed solvents thereof.

The compound (18) can be obtained by converting the hydroxy group of the compound (27) to a halogen atom (e.g., a chlorine atom, a bromine atom or an iodine atom) or a substituted sulfonyloxy group (e.g., p-toluenesulfonyloxy group or a methanesulfonyloxy group) by a routine method. Specifically, the compound (18) can be obtained by reacting the compound (27) with, for example, methanesulfonyl chloride or p-toluenesulfonyl chloride in an inert solvent at a temperature from −20° C. to the boiling point of the solvent used for 10 minutes to 48 hours in the presence of a base. Examples of the appropriate inert solvent include: halogenated hydrocarbon solvents such as chloroform and dichloromethane; ether solvents such as diethyl ether, THF, 1,4-dioxane and 1,2-dimethoxyethane; or aprotic polar solvents such as acetonitrile, dimethylformamide, N-methyl-2-pyrrolidinone and DMSO; or mixed solvents thereof. Examples of the appropriate base include: organic bases such as triethylamine and pyridine; or inorganic bases such as potassium carbonate and sodium hydroxide. Moreover, when $LG^1$ is halogen such as a chlorine atom or a bromine atom, the compound (18) can be obtained by reacting a compound (18) wherein $LG^1$ is a substituted sulfonyloxy group such as a p-toluenesulfonyloxy group or a methanesulfonyloxy group, with, for example, lithium bromide, in an inert solvent at a temperature from −20° C. to the boiling point of the solvent used for 10 minutes to 48 hours. Examples of the appropriate inert solvent include: halogenated hydrocarbon solvents such as chloroform and dichloromethane; ether solvents such as diethyl ether, THF, 1,4-dioxane and 1,2-dimethoxyethane; or aprotic polar solvents such as acetonitrile, dimethylformamide, N-methyl-2-pyrrolidinone and DMSO; or mixed solvents thereof. Moreover, in an alternative method, the compound (18) can be obtained, for example, by reacting the compound (27) with carbon tetrachloride or carbon tetrabromide in an appropriate inert solvent in the presence of triphenylphosphine. Examples of the inert solvent include: halogenated hydrocarbon solvents such as chloroform and dichloromethane; aromatic hydrocarbon solvents such as benzene and toluene; ether solvents such as diethyl ether, tetrahydrofuran (THF) and 1,4-dioxane; or mixed solvents thereof.

[Production Method 9: Method for Producing Compound (18)]

The starting compound (18) can also be produced by, for example the following method:

[Formula 18]

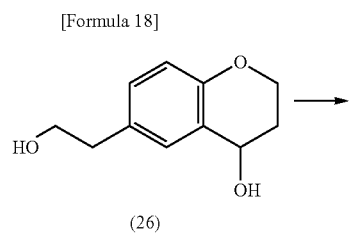
(26)

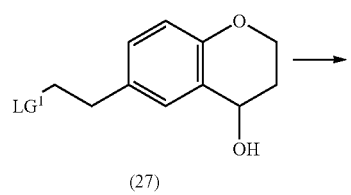
(27)

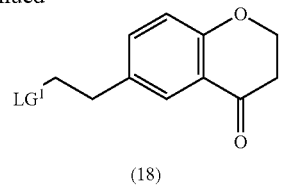
(18)

wherein $LG^1$ is as defined above.

A compound (28) can be obtained by converting the primary hydroxy group of the compound (26) to a substituted sulfonyloxy group such as a p-toluenesulfonyloxy group or a methanesulfonyloxy group by a routine method. The compound (18) can be obtained by oxidizing the hydroxy group of the compound (28) in an appropriate inert solvent by a routine method, for example, manganese dioxide oxidation or dimethyl sulfoxide (DMSO) oxidation. Examples of the appropriate inert solvent in the manganese dioxide oxidation can include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; and aprotic polar solvents such as acetonitrile, dimethylformamide and N-methyl-2-pyrrolidinone. Examples of the appropriate inert solvent in the dimethyl sulfoxide (DMSO) oxidation include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or DMSO; or mixed solvents thereof.

[Production Method 10: Method for Producing Compound (27)]

The intermediate compound (27) in Production Method 8 can also be produced by, for example, the following method:

[Formula 19]

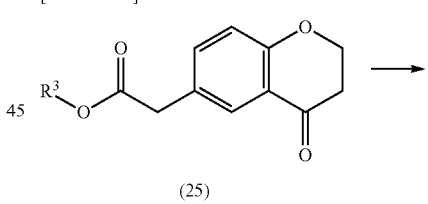
(25)

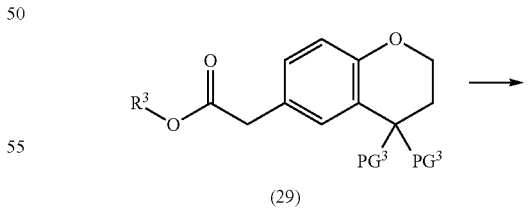
(29)

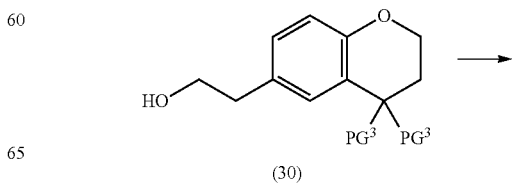
(30)

-continued

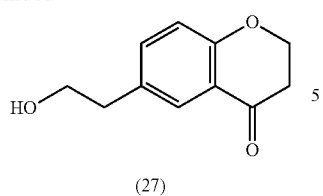

(27)

wherein $R^3$ is as defined above; and $PG^3$ represents a methoxy group, a methylthio group, or the like, or two $PG^3$ moieties may form a ring to represent a cyclic acetal group such as a 1,3-dioxolane group or a 1,3-dioxane group.

The ketone as the compound (25) is converted to dialkylacetal or dialkylthioacetal as a compound (29) by a routine method. This compound is reduced with an appropriate reducing agent (e.g., lithium aluminum hydride, lithium borohydride, sodium borohydride or diborane) in an appropriate inert solvent to form a compound (30). The compound (27) can be obtained by deprotecting the compound (30) by an appropriate method. Examples of the inert solvent in the reduction reaction of the compound (29) include: halogenated hydrocarbon solvents such as chloroform and dichloromethane; aromatic hydrocarbon solvents such as benzene and toluene; ether solvents such as diethyl ether, THE, 1,4-dioxane and 1,2-dimethoxyethane; and lower alcoholic solvents such as methanol, ethanol and isopropanol; or mixed solvents thereof. When $PG^3$ in the compound (30) is a methoxy group, its deprotection can be performed in the same way as in the deprotection method of the compound (15) described in Production Method 3.

The compound (25) can be synthesized by, for example, a method described in FR Patent No. 2672601.

[Production Method 11: Method for Producing Compound (13-1)]

A compound (13-1), which is a compound (13) used in Production Method 2 wherein Z represents a group represented by a formula (3-1-1):

[Formula 20]

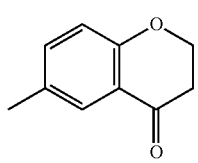

(3-1-1)

can also be produced by the following method:

[Formula 21]

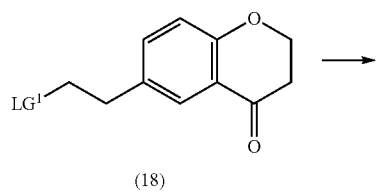

(18)

-continued

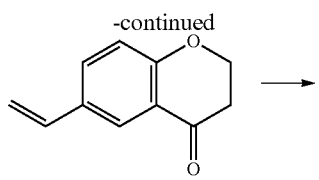

(31)

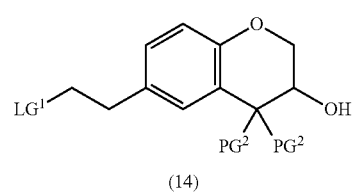

(13-1)

wherein $LG^1$ is as defined above.

A compound (31) can be obtained by treating the compound (18) with an organic base (e.g., 1,8-diazabicyclo[5.4.0]undec-7-ene (DBU) or 1,4-diazabicyclo[2.2.2]octane (DABCO)) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or aprotic polar solvents such as acetonitrile, dimethylformamide and N-methyl-2-pyrrolidinone; or mixed solvents thereof. The compound (13-1) can be obtained by reacting this compound (31) with an organic peracid (e.g., m-chloroperbenzoic acid or peracetic acid) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; and ether solvents such as diethyl ether, THF, 1,4-dioxane and 1,2-dimethoxyethane.

[Production Method 12: Method for Producing Compound (14)]

The compound (14) used in Production Method 3 can also be produced by the following method with reference to a method described in a literature (e.g., Tetrahedron Lett., 2005, 46 (3), 447; and Heterocycles, 2007, 74 (1), 803):

[Formula 22]

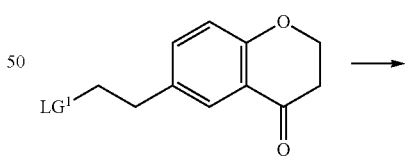

(18)

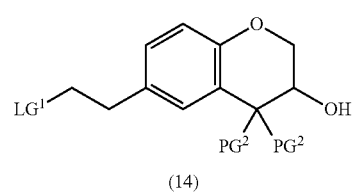

(14)

wherein $LG^1$ and $PG^2$ are as defined above.

The compound (14) can be obtained by reacting the compound (18) with, for example, iodine or diacetoxyiodobenzene, in an appropriate solvent at a temperature from −20° C.

[Production Method 13: Method for Producing Compound (16)]

The compound (16) used in Production Method 4 can also be produced by the following method described in a literature (e.g., Synth. Commun., 24 (18), 2637; and J. Org. Chem., 1990, 55, 6161):

[Formula 23]

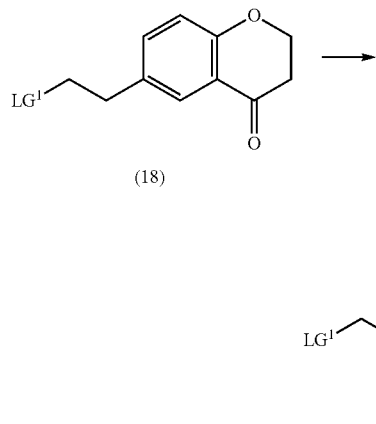

wherein $LG^1$ is as defined above.

The compound (16) can be obtained by reacting the compound (18) with, for example, [hydroxy(tosyloxy)iodo]benzene or pyrrolidone hydrotribromide in an appropriate inert solvent at a temperature from −20° C. to the boiling point of the solvent used in the presence of an appropriate acid or base.

In the production method using [hydroxy(tosyloxy)iodo]benzene, examples of the appropriate acid include organic acids such as p-toluenesulfonic acid. Moreover, examples of the appropriate inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; aprotic polar solvents such as acetonitrile and N-methyl-2-pyrrolidinone; or mixed solvents thereof.

[Production Method 14: Method for Producing Compound (1-6)]

A compound (1-6), which is a compound represented by the formula (1) wherein each of $Y^1$ and $Y^2$ represents a hydrogen atom, and Z represents a group represented by a formula (3-3-2):

[Formula 24]

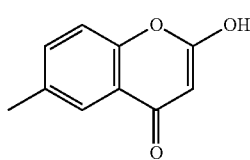

can also be produced by the following method:

[Formula 25]

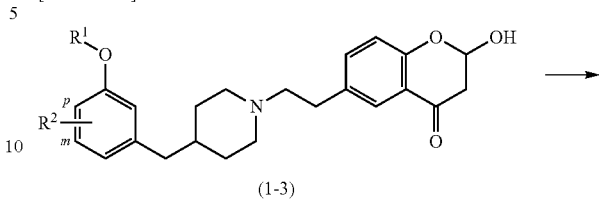

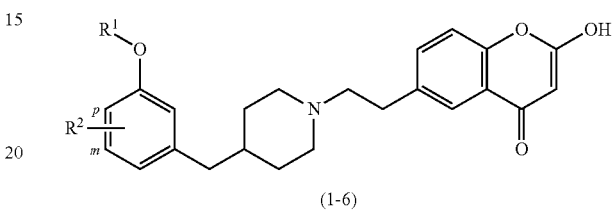

wherein $R^1$ and $R^2$ are as defined above.

The compound (1-6) can be obtained by oxidizing the hydroxy group of the compound (1-3) in an appropriate inert solvent at a temperature from −20° C. to the boiling point of the solvent used using a general method, for example, Swern oxidation, Pfitzner-Moffatt oxidation, DMSO oxidation using a sulfur trioxide/pyridine complex, or an oxidation reaction using a Dess-Martin reagent or a hypervalent iodine compound such as o-iodoxybenzoic acid (IBX). Examples of the appropriate inert solvent in the DMSO oxidation include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or DMSO; and mixed solvents thereof. Examples of the appropriate inert solvent in the oxidation reaction using a hypervalent iodine compound include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or aprotic polar solvents such as acetonitrile, dimethylformamide and N-methyl-2-pyrrolidinone; or mixed solvents thereof.

[Production Method 15: Method for Producing Compound (1-7)]

A compound (1-7), which is a compound represented by the formula (1) wherein each of $Y^1$ and $Y^2$ represents a hydrogen atom, and Z represents a group represented by a formula (3-4-2):

[Formula 26]

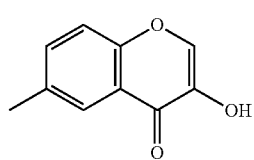

can also be produced by the following method:

[Formula 27]

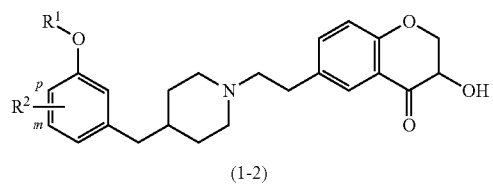

(1-2)

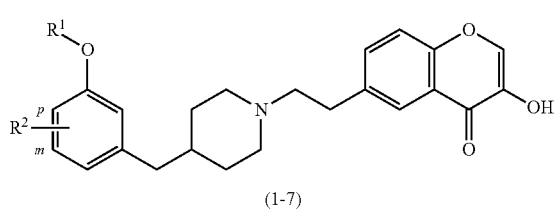

(1-7)

wherein R¹ and R² are as defined above.

The compound (1-7) can be obtained by oxidizing the hydroxy group of the compound (1-2) in an appropriate inert solvent at a temperature from −20° C. to the boiling point of the solvent used using a general oxidation method, for example, Swern oxidation, Pfitzner-Moffatt oxidation, DMSO oxidation using a sulfur trioxide/pyridine complex, or an oxidation reaction using a Dess-Martin reagent or a hypervalent iodine compound such as o-iodoxybenzoic acid (IBX). Examples of the appropriate inert solvent in the DMSO oxidation include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or DMSO; and mixed solvents thereof. Examples of the appropriate inert solvent in the oxidation reaction using a hypervalent iodine compound include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; or aprotic polar solvents such as acetonitrile, dimethylformamide and N-methyl-2-pyrrolidinone; or mixed solvents thereof.

[Production Method 16: Method for Producing Compound (33)]

A compound (33), which is a compound (12) used in Production Method 1 wherein each of Y1 and Y2 represents a hydrogen atom, and Z represents a group represented by a formula (3-4-2):

[Formula 28]

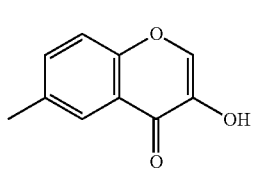

(3-4-2)

can also be produced by the following production method:

[Formula 29]

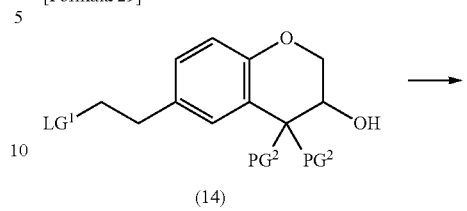

(14)

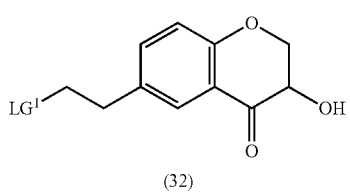

(32)

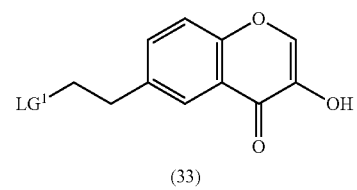

(33)

wherein LG1 and PG2 are as defined above.

A compound (32) is obtained by treating the compound (14) with an inorganic acid (e.g., hydrochloric acid, phosphoric acid or sulfuric acid), an organic acid (e.g., trifluoroacetic acid, p-toluenesulfonic acid or acetic acid) or a weakly acidic salt (e.g., pyridinium p-toluenesulfonate) in an appropriate inert solvent at a temperature from −20° C. to the boiling point of the solvent used. Examples of the inert solvent include: halogenated hydrocarbon solvents such as chloroform and dichloromethane; aromatic hydrocarbon solvents such as benzene and toluene; ether solvents such as diethyl ether, THF, 1,4-dioxane and 1,2-dimethoxyethane; lower alcoholic solvents such as methanol, ethanol and 2-propanol; aprotic polar solvents such as acetonitrile, dimethylformamide and N-methyl-2-pyrrolidone; or water; or mixed solvents thereof. The compound (33) can be obtained by oxidizing the hydroxy group of the compound (32) in the same way as the method described in Production Method 15.

[Production Method 17: Method for Producing Compound (34); 6-(2-{4-[4-bromo-3-(2-hydroxyethoxy)benzyl]piperidin-1-yl}ethyl)-3-hydroxy-4H-chromen-4-one]

[Formula 30]

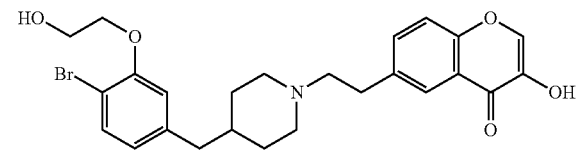

(34)

The compound (34) can be synthesized by the following production method:
A compound (RE2) can be converted to a compound (35), for example, by reaction with acetic anhydride under Schot-
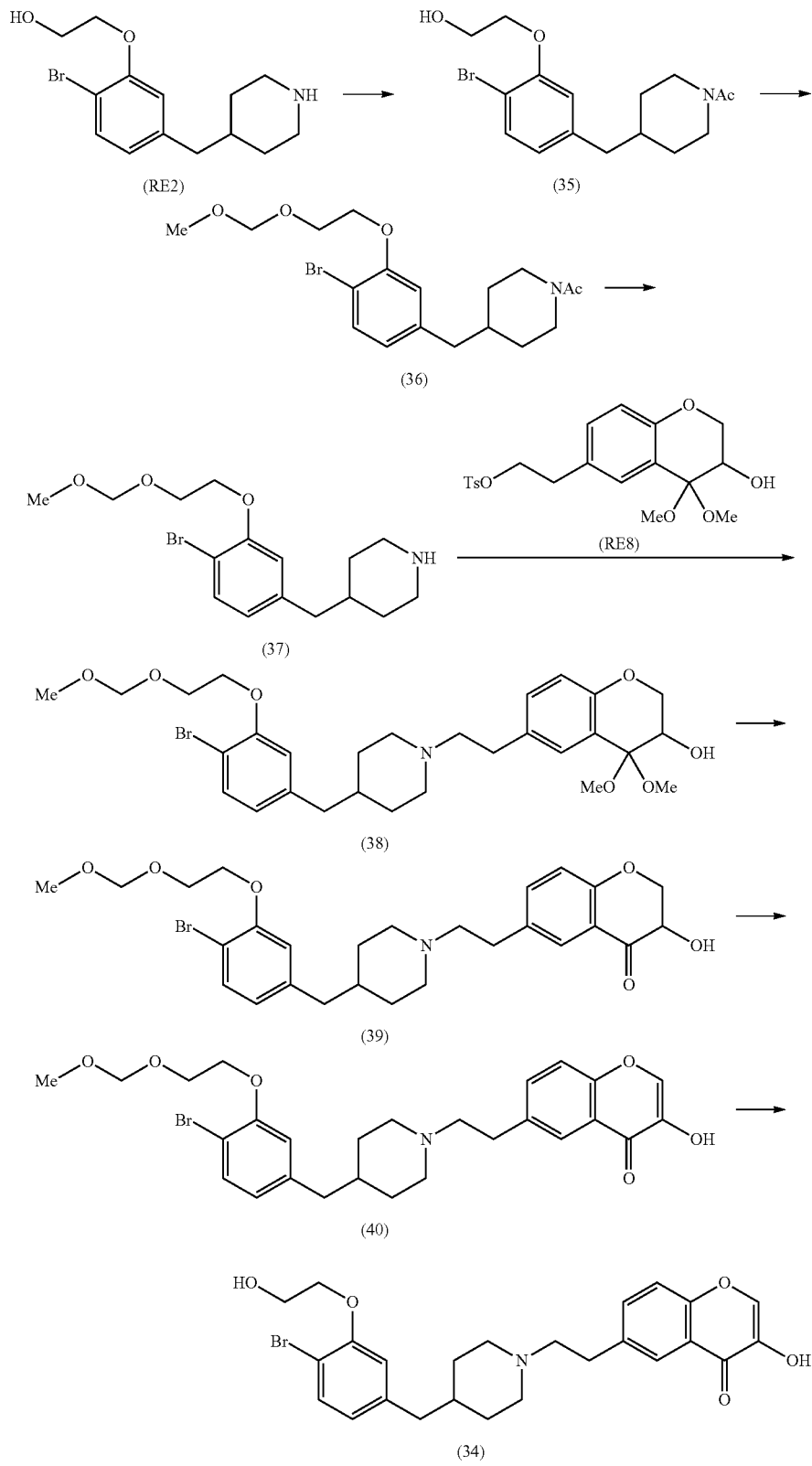

ten-Baumann conditions. The compound (35) can be converted to a compound (36), for example, by reaction with methoxymethyl chloride in the presence of sodium hydride as a base in N,N-dimethylformamide. This compound can be converted to a compound (37), for example, by reaction with sodium hydroxide, potassium hydroxide, or the like, in an ether solvent (e.g., 1,4-dioxane or tetrahydrofuran), an alcoholic solvent (e.g., methanol or ethanol) or water, or a mixed solvent thereof. A compound (39) can be obtained by reacting the compound (37) with a compound (RE8) in the same way as Production Method 1 to form a compound (38), which is then reacted, for example, with pyridinium p-toluenesulfonate or silica gel in an ether solvent (e.g., 1,4-dioxane or tetrahydrofuran) or an alcoholic solvent (e.g., methanol or ethanol). The compound (34) can be obtained by subjecting The introduction of such a protective group and deprotection can be performed by a method routinely used in organic synthetic chemistry (see e.g., Protective Groups in Organic Synthesis described above) or a method equivalent thereto.

The intermediates and the compounds of interest in the production methods can be isolated and purified by purification methods routinely used in organic synthetic chemistry, for example, neutralization, filtration, extraction, washing, drying, concentration, recrystallization and various chromatography techniques. Moreover, the intermediates may be subjected to the next reaction without being particularly purified.

Among the compounds of the present invention, some compounds can have tautomers. Examples of tautomerism include events represented by formulas (I) to (III):

[Formula 32]

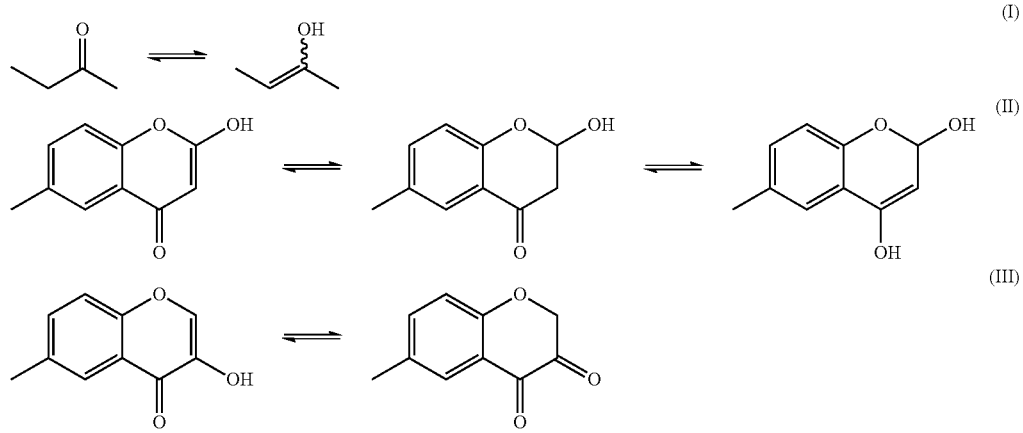

the compound (39) to DMSO oxidation in the same way as Production Method 15 to form a compound (40) and reacting the compound (40) with an inorganic acid (e.g., hydrochloric acid or sulfuric acid) or an organic acid (e.g., p-toluenesulfonic acid or trifluoroacetic acid).

The starting materials, reagents, etc., used in these production methods are commercially available compounds or can be produced from compounds known in the art using methods known in the art, unless otherwise specified. Moreover, functional groups in the compound of the formula (1) may be converted appropriately to form another compound of the formula (1). The conversion of functional groups can be performed by a general method usually performed [see e.g., R. C. Larock, Comprehensive Organic Transformations (1989)].

When any functional group other than a reactive site in the production methods is altered under the described reaction conditions or is inappropriate for carrying out the described method, the compound of interest can be obtained by protecting this functional group in advance with an appropriate protective group and then carrying out the reaction, followed by deprotection. Usual protective groups as described in, for example, T. W. Greene, Protective Groups in Organic Synthesis, John Wiley & Sons Inc. (1981) can be used as the protective group. Specific examples thereof can include: protective groups for amine such as ethoxycarbonyl, tert-butoxycarbonyl, acetyl and benzyl; and protective groups for the hydroxy group such as trialkylsilyl, acetyl, methoxymethyl and benzyl. Examples of protective groups for ketone can include dimethylacetal, 1,3-dioxane, 1,3-dioxolane, S,S'-dimethyl dithioacetal, 1,3-dithiane and oxime.

The present invention encompasses all possible isomers such as optical isomers, stereoisomers, positional isomers and rotational isomers, including the tautomers, and mixtures thereof. For example, when the compound represented by the formula (1) has optical isomers, each optical isomer is also encompassed by the compound of the formula (1). These isomers can be separated and purified by a separation approach known in the art such as chromatography or recrystallization.

The compound (1) can be resolved into each optical isomer using any optical resolution method known by those skilled in the art. For example, it is performed by forming diastereomeric salts according to a routine method using an optically active acid, then separating these salts into two kinds of diastereomeric salts, and subsequently converting these salts into free bases. Examples of the optically active acid include: monocarboxylic acids such as mandelic acid, N-benzyloxyalanine and lactic acid; dicarboxylic acids such as tartaric acid, o-diisopropylidene tartaric acid and malic acid; and sulfonic acids such as camphor sulfonic acid and bromocamphor sulfonic acid. Examples of the temperature at which the salt is formed include the range from room temperature to the boiling point of the solvent.

The compound represented by the formula (1) also encompasses compounds labeled with an isotope such as $^{3}H$, $^{14}C$, $^{35}S$ or $^{125}I$ and heavy hydrogen-substituted forms containing $^{2}H(D)$ converted from $^{1}H$.

The pharmaceutically acceptable salt of the compound represented by the formula (1) is a nontoxic salt routinely used. Examples thereof include: acid-addition salts such as organic acid salts (e.g., acetate, propionate, trifluoroacetate, maleate, fumarate, citrate, succinate, tartrate, methanesulfonate, benzenesulfonate, formate and toluenesulfonate) or inorganic acid salts (e.g., hydrochloride, hydrobromide, hydroiodide, sulfate, nitrate and phosphate); salts with amino acids (e.g., alginic acid, aspartic acid and glutamic acid); metal salts such as alkali metal salts (e.g., sodium salt and potassium salt) or alkaline earth metal salts (e.g., calcium salt and magnesium salt); ammonium salts; or organic base salts (e.g., trimethylamine salt, triethylamine salt, pyridine salt, picoline salt, dicyclohexylamine salt and N,N'-dibenzylethylenediamine salt).

To obtain the pharmaceutically acceptable salt of the compound represented by the formula (1), a compound (1) obtained in the form of a pharmaceutically acceptable salt can be purified directly. On the other hand, a compound (1) in a free form is dissolved or suspended in an appropriate organic solvent. To this solution, an acid or a base is added, and a salt can be formed therefrom by a usual method. For example, the solution can be mixed with a pharmaceutically acceptable acid or alkali in a solvent such as water, methanol, ethanol or acetone to form a salt.

Moreover, the compound represented by the formula (1) and the pharmaceutically acceptable salt thereof may exist as hydrates with water or solvates with various solvents such as ethanol. Such hydrates or solvates are also encompassed by the present invention.

The compound represented by the formula (1) and the pharmaceutically acceptable salt thereof obtained as crystals may have crystal polymorph. These crystal polymorphs are also encompassed by the present invention.

The compound of the present invention and the pharmaceutically acceptable salt thereof have an inhibitory effect on human serotonin reuptake. Therefore, the compound and the salt are useful as therapeutic drugs for disease mediated by the serotonergic nervous system. Examples of the disease mediated by the serotonergic nervous system include depression and anxiety. Depression is included in mood disorder in psychiatric disease classification. This mood disorder mainly includes depressive disorder and bipolar disorder. More specific examples of general depression include (i) depressive disorder including major depressive disorder, dysthymic disorder or depressive disorder not otherwise specified, (ii) depression or (iii) seasonal affective disorder. The compound and the salt are useful as therapeutic drugs for these diseases or preventive drugs for relapse thereof.

Furthermore, the compound and the salt are also useful as therapeutic drugs for (iv) major depressive episodes in bipolar disorder or preventive drugs for relapse thereof. On the other hand, anxiety (anxiety disorder) mainly includes anxiety disorder and phobia. Examples of anxiety (anxiety disorder) for which the compound and the salt are useful as therapeutic drugs or preventive drugs for relapse include (v) panic disorder, obsessive compulsive disorder, posttraumatic stress disorder, acute stress disorder, generalized anxiety disorder or anxiety disorder caused by general physical disease, (vi) anxiety disorder including substance-induced anxiety disorder, (vii) agoraphobia, (viii) social phobia, (ix) avoidant personality disorder and (x) psychosomatic disease. Moreover, the compound and the salt are also useful for depressive symptoms or anxiety symptoms accompanying other diseases (schizophrenia, dementia, etc.). Furthermore, the compound and the salt are also useful for the treatment or prevention of memory disorder including dementia, amnesia and aging memory disorder; eating behavior disorder including anorexia nervosa and neurogenic starvation; obesity; somnipathy; schizophrenia; alcoholism, smoking addiction, nicotine dependence, drugs dependence such as narcotics, stimulant drugs and psychotropic drugs; cluster headache; migraine; pain; Alzheimer's disease; chronic paroxysmal migrain; headache related to angiopathy; Parkinson's disease including Parkinson's disease with dementia, depression, anxiety, neuroleptic-induced Parkinsonism and tardive dyskinesia; endocrine abnormality such as hyperprolactinemia; vasospasm (particularly, in the cerebrovascular system); hypertension; gastrointestinal disorder involving change in motility and secretion; sexual dysfunction including premature ejaculation; etc.

The dose of the compound of the present invention or the pharmaceutically acceptable salt thereof is determined according to the age and conditions of a patient. One dose of approximately 0.1 mg, 1 mg, 10 mg, 50 mg, 100 mg, 250 mg, 500 mg or 1000 mg on average of the compound (1) is effective for, for example, the disease described above such as depression or anxiety. In general, the compound or the salt can be administered at a daily dose of 0.1 mg/individual to approximately 1,000 mg/individual, preferably 1 mg/individual to approximately 100 mg/individual when administered to a human. The number of doses in one day is one or several doses per day, for example, 1, 2 or 3 doses are given each time.

The compound of the present invention or the pharmaceutically acceptable salt thereof can be administered orally or parenterally (e.g., intravenously, subcutaneously, intramuscularly, intrathecally, locally, transrectally, percutaneously, transnasally or transpulmonarily) as a pharmaceutical composition when used in treatment. Examples of dosage forms for oral administration include dosage forms such as tablets, capsules, pills, granules, fine granules, powders, liquids, syrups and suspensions. Examples of dosage forms for parenteral administration include preparations in forms such as aqueous injections, nonaqueous injections, suppositories, transnasal preparations and transdermal preparations [lotions, emulsions, ointments, creams, jellies, gels, patches (tapes, percutaneous patch preparations, poultices, etc.), powders for cutaneous application, etc.]. These preparations are prepared using a technique conventionally known in the art and can contain nontoxic and inert carriers or excipients usually used in the pharmaceutical field.

Substances that are routinely used in the pharmaceutical field and do not react with the compound represented by the formula (1) or the pharmaceutically acceptable salt thereof are used as pharmaceutical carriers. Specifically, a pharmaceutical composition containing the compound represented by the formula (1) or the pharmaceutically acceptable salt thereof can contain pharmaceutical carriers such as excipients, binders, lubricants, stabilizing agents, disintegrants, buffers, solubilizers, tonicity agents, pH adjusters, surfactants, emulsifying agents, suspending agents, dispersing agents, suspension stabilizers, thickening agents, viscosity adjusters, gelling agents, soothing agents, preservatives, plasticizers, penetration enhancers, antiaging agents, humectants, antiseptics and flavors. Two or more of these pharmaceutical carrier additives may be selected appropriately for use.

Specific examples of the pharmaceutical carrier additives include lactose, inositol, glucose, sucrose, fructose, mannitol (mannite), dextran, sorbitol (sorbit), cyclodextrin, starch (potato starch, corn starch, amylopectin, etc.), partially pregelatinized starch, saccharose, magnesium aluminometasilicate, synthetic aluminum silicate, crystalline cellulose, sodium carboxymethylcellulose, hydroxypropyl starch, calcium carboxymethylcellulose, ion-exchange resins, methylcellulose, gelatin, gum arabic, pullulan, hydroxypropylcellulose, low-substituted hydroxypropylcellulose, hydroxypropylmethylcellulose, carboxymethylcellulose, hydroxyethylcellulose, polyvinylpyrrolidone, polyvinyl alcohol, alginic acid, sodium alginate, light anhydrous silicic acid, magnesium stearate, calcium stearate, aluminum stearate, cetostearyl alcohol, wax, talc, tragacanth, bentonite, veegum, carboxyvinyl polymers, titanium dioxide, fatty acid esters, sodium lauryl sulfate, glycerin, fatty acid glycerin ester, purified lanolin, glycerogelatin, squalane, silicone oil, vegetable oil (sesame oil, olive oil, soybean oil, cottonseed oil, castor oil, etc.), liquid paraffin (liquid petrolatum), soft paraffin, white petroleum, yellow petroleum, paraffin, wax (beeswax, carnauba wax, white beeswax, etc.), water, propylene glycol, polyethylene glycol, lauryl alcohol, myristyl alcohol, oleyl alcohol, cetyl alcohol, ethanol, sodium chloride, sodium hydroxide, hydrochloric acid, citric acid, lauric acid, myristic acid, stearic acid, oleic acid, benzyl alcohol, glutamic acid, glycine, methyl p-hydroxybenzoate, propyl p-hydroxybenzoate, p-hydroxybenzoic acid esters, cholesterol esters, ethylene glycol monoalkyl esters, propylene glycol monoalkyl esters, glycerin monostearate, isopropyl myristate, isopropyl palmitate, carboxy polymethylene, saccharine, strawberry flavor, peppermint flavor, cocoa butter, polyisobutylene, vinyl acetate copolymers, acrylic copolymers, triethyl citrate, acetyl triethyl citrate, diethyl phthalate, diethyl sebacate, dibutyl sebacate, acetylated monoglyceride, diethylene glycol, dodecylpyrrolidone, urea, ethyl laurate, azone, kaolin, zinc oxide, agarose, carrageenan, gum acacia, xanthan gum, potassium laurate, potassium palmitate, potassium myristate, sodium cetyl sulfate, castor oil sulfate (turkey-red oil), Span (sorbitan stearate, sorbitan monooleate, sorbitan sesquioleate, sorbitan trioleate, etc.), Tween (polysorbate 20, polysorbate 40, polysorbate 60, polysorbate 65, polysorbate 80, polysorbate 85, polyoxyethylene sorbitan fatty acid ester, etc.), polyoxyethylene hydrogenated castor oil (so-called HCO), polyoxyethylene lauryl ether, polyoxyethylene cetyl ether, polyoxyethylene oleyl ether, polyethylene glycol monolaurate, polyethylene glycol monostearate, poloxamers (so-called Pluronic), lecithin (including even purified phospholipids isolated from lecithin, such as phosphatidylcholine and phosphatidylserine) and hydrogenated lecithin.

The compound of the present invention or the pharmaceutically acceptable salt thereof is usually administered in the form of a preparation prepared by mixing the compound or the salt with the pharmaceutical carriers, when used in the pharmaceutical use as described above. This preparation is prepared according to a usual method. For example, a pharmaceutical composition containing 0.051 to 99% by weight, preferably 0.05 to 80% by weight, more preferably 0.1 to 70% by weight, further preferably 0.1 to 50% by weight of the benzylpiperidine compound of the present invention or the pharmaceutically acceptable salt thereof as an active ingredient can be prepared. Such a preparation may also contain other ingredients of therapeutic value.

The compound of the present invention or the pharmaceutically acceptable salt thereof can be used in combination with a drug (combined drug) such as an antidepressant, an anxiolytic drug, a therapeutic drug for schizophrenia, a dopamine receptor agonist, a therapeutic drug for Parkinson's disease, an antiepileptic, an anticonvulsant, an analgesic, a hormone preparation, a therapeutic drug for migraine, an adrenaline β receptor antagonist, a therapeutic drug for dementia or a therapeutic drug for mood disorder, for the purpose of enhancing its effect. Moreover, the compound or the salt can be used in combination with a drug (combined drug) such as an antiemetic, a sleep inducing drug or an anticonvulsant, for the purpose of reducing its adverse reaction. The timings at which the compound of the present invention and the combined drug are administered are not limited. They may be administered to a recipient simultaneously or at a time interval. Moreover, a combination of the compound of the present invention and the combined drug may be used. The dose of the combined drug can be selected appropriately with respect to a dose clinically used. Moreover, the mixing ratio between the compound of the present invention and the combined drug can be selected appropriately according to a recipient, an administration route, a target disease, conditions, a combination, etc. For example, when the recipient is a human, 0.01 to 1000 parts by weight of the combined drug can be used with respect to 1 part by weight of the compound of the present invention.

EXAMPLES

Hereinafter, the present invention will be described in more detail with reference to Reference Examples, Examples and Test Examples. However, the technical scope of the present invention is not intended to be limited to these Examples. The names of compounds shown in Reference Examples and Examples below do not necessarily follow the IUPAC nomenclature.

Compounds were identified using proton nuclear magnetic resonance absorption spectra ($^1$H-NMR spectra) or the like. Data on $^1$H-NMR spectra is shown for some compounds.

Reference Example 1

Compound (RE1):
4-[4-Bromo-3-(2-methoxyethoxy)benzyl]piperidine hydrochloride

The compound was synthesized according to the following production method:

Production Method

[Formula 33]

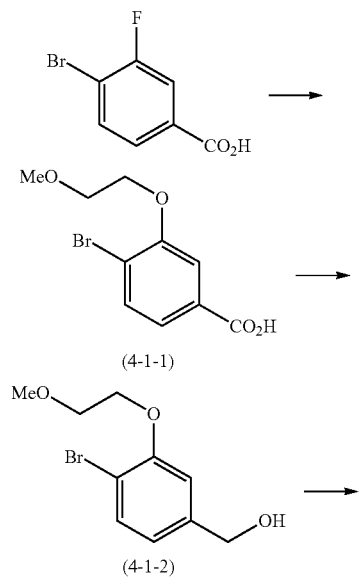

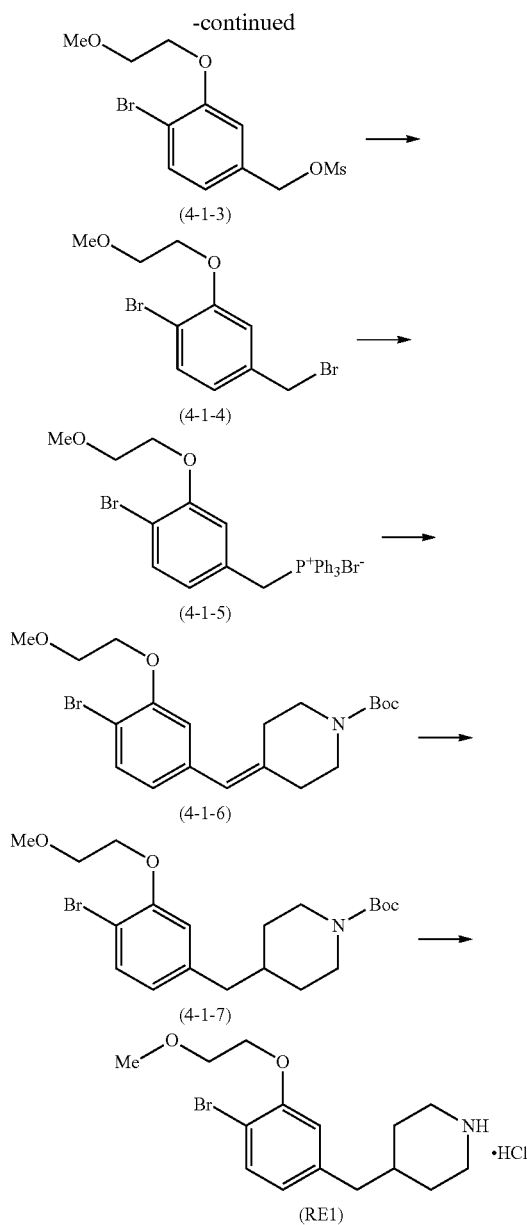

Compound (4-1-1): 4-Bromo-3-(2-methoxyethoxy)benzoic acid

Potassium t-butoxide (24.29 g, 217 mmol) was added to a solution of 2-methoxyethanol (16.48 g, 217 mmol) in anhydrous N-methyl-2-pyrrolidinone (175 mL) at room temperature under nitrogen atmosphere. After confirmation of dissolution by visual observation, 4-bromo-3-fluorobenzoic acid (19.00 g, 86.8 mmol) was added thereto in small portions. The reaction mixture was stirred at 90° C. for 6 hours. After cooling to room temperature, the reaction mixture was added dropwise to a solution of concentrated hydrochloric acid (36%, 25 mL) in water (500 mL) in 40 minutes with water cooling, and the mixture was stirred at an internal temperature of 20 to 25° C. for 1 hour. Then, the resulting precipitate was collected by filtration, and the residue was washed with water (20 mL×2) and acetonitrile (20 mL×2) and dried under reduced pressure to obtain a white solid (26.41 g). This solid was added to acetonitrile (380 mL), and the mixture was heated to around the reflux temperature. After confirmation of dissolution by visual observation, the solution was cooled. When the deposition of crystals started around 75° C., the solution was stirred for 1 hour with the temperature kept at 65 to 70° C., then cooled again to around 30° C. over 2.5 hours, and subsequently stirred for 1 hour with the internal temperature kept at 20° C. by water cooling. The resulting precipitate was collected by filtration, and the residue was washed with acetonitrile (20 mL×2) to obtain the title compound (4-1-1) (20.09 g, 85%) as light brown needle-like crystals.

Compound (4-1-2): [4-Bromo-3-(2-methoxyethoxy)phenyl]methanol

A boron trifluoride/diethyl ether complex (35 mL, 285 mmol) was added dropwise to a suspension of sodium borohydride (8.08 g, 213.5 mmol) in anhydrous THF (100 mL) with water cooling, and the mixture was stirred for 1 hour in this state. A solution of the compound (4-1-1) (19.50 g, 71.2 mmol) in anhydrous THF (300 mL) was added dropwise thereto for 30 minutes with the internal temperature kept at 25° C. or lower by water cooling. The reaction mixture was stirred for 3 hours, and then, water (200 mL) was added dropwise thereto in 20 minutes with the internal temperature kept at 20° C. or lower by ice cooling. The reaction mixture was separated into aqueous and organic layers by the addition of toluene (200 mL), and the aqueous layer was subjected to re-extraction with toluene (200 mL). Combined organic layers were washed with a 3% aqueous sodium bicarbonate solution (200 mL) and water (200 mL), and then, toluene was distilled off under reduced pressure. Toluene (200 mL) was added to the concentrated residue, and toluene was distilled off under reduced pressure to obtain the title compound (4-1-2) (18.18 g).

Compound (4-1-3): 4-Bromo-3-(2-methoxyethoxy)benzyl methanesulfonate

A solution of methanesulfonyl chloride (8.56 g, 74.7 mmol) in toluene (18 mL) was added dropwise to a solution of the compound (4-1-2) (18.00 g, corresponding to 71.17 mmol), trimethylamine hydrochloride (467 mg, 7.12 mmol) and triethylamine (19.8 mL, 142 mmol) in toluene (90 mL) in 30 minutes with the internal temperature kept at 5° C. or lower in a salt-ice bath, and the reaction mixture was stirred at an internal temperature of 5° C. or lower for 2 hours. The reaction solution was poured to a 5% aqueous potassium bisulfate solution (180 mL) with the temperature kept at 10° C. or lower by cooling in an ice bath, and the mixture was stirred for 30 minutes. The reaction mixture was warmed to room temperature and separated into aqueous and organic layers, and the aqueous layer was subjected to re-extraction with toluene (90 mL). Combined organic layers were washed with water (180 mL), and toluene was distilled off under reduced pressure to obtain the title compound (4-1-3) (22.43 g).

Compound (4-1-4): 1-Bromo-4-(bromomethyl)-2-(2-methoxyethoxy)benzene

Anhydrous lithium bromide (18.54 g, 214 mmol) was added to a solution of the compound (4-1-3) (22.43 g, corresponding to 71.17 mmol) in anhydrous THF (100 mL) at room temperature, and the reaction mixture was heated under reflux for 1 hour. After cooling to room temperature, the reaction mixture was separated into aqueous and organic layers by the addition of water (100 mL) and toluene (100 mL), and the aqueous layer was subjected to re-extraction with toluene (100 mL). Combined organic layers were washed with a 5% aqueous sodium bicarbonate solution (100 mL) and water (100 mL) in this order, and toluene was distilled off under reduced pressure to obtain the title compound (4-1-4) (19.54 g) as a white solid.

Moreover, this title compound (4-1-4) can also be synthesized directly from the compound (4-1-2) as follows by bypassing the compound (4-1-3):

A mixed solution of toluene (80 g) and an aqueous hydrogen bromide solution (47%, 53 g) containing the compound (4-1-2) (16.0 g, 61.3 mmol) was stirred at an internal temperature of 65-70° C. for 2 hours. After cooling to room temperature, the reaction mixture was separated into aqueous and organic layers by the addition of water (16 g), and the organic layer was washed with a 5% aqueous sodium bicarbonate solution (48 g) and water (48 g) in this order. The organic layer was concentrated under reduced pressure to obtain the title compound (4-1-4) (17.9 g, 90%).

Compound (4-1-5): [4-Bromo-3-(2-methoxyethoxy)benzyl](triphenyl)phosphonium bromide Triphenylphosphine (18.67 g, 71.17 mmol) was added to a solution of the compound (4-1-4) (19.54 g, corresponding to 71.17 mmol) in toluene (100 mL), and the reaction mixture was heated under reflux for 3.5 hours. After cooling to room temperature, the solution was stirred for 1 hour with the temperature kept at 20° C. with water cooling. Then, the resulting precipitate was collected by filtration, and the residue was washed with toluene (40 mL×3) and dried under reduced pressure to obtain the title compound (4-1-5) (32.44 g, 78%).

Compound (4-1-6): tert-Butyl 4-[4-bromo-3-(2-methoxyethoxy)benzylidene]piperidine-1-carboxylate A solution of the compound (4-1-5) (32.00 g, 54.6 mmol), 1-tert-butoxycarbonyl-4-piperidone (11.42 g, 57.3 mmol) and potassium carbonate (11.30 g, 81.9 mmol) in 2-propanol (160 mL) was heated under reflux for hours. After cooling to room temperature, the salt was collected by filtration, and the salt as the residue was washed with 2-propanol (30 mL×2). The filtrate was concentrated under reduced pressure to obtain a concentrated residue (41.08 g). Toluene was added thereto, and toluene was distilled off under reduced pressure (200 mL×2). Subsequently, toluene (96 mL) was added to the concentrated residue, and n-hexane (290 mL) was added dropwise thereto in 30 minutes with the temperature kept at 20-25° C. by water cooling. The mixture was stirred for 1 hour in this state and then stirred for 1 hour under ice cooling, and the resulting precipitate was collected by filtration. The residue was washed with toluene/n-hexane (toluene:n-hexane=1:3, 20 mL×2), and the filtrate was distilled off under reduced pressure to obtain the title compound (4-1-6) (27.93 g) as a pale yellow oil.

Compound (4-1-7): tert-Butyl 4-[4-bromo-3-(2-methoxyethoxy)benzyl]piperidine-1-carboxylate The compound (4-1-6) (27.93 g, corresponding to 54.6 mmol) was subjected to a hydrogenation reaction at ambient pressure at an internal temperature of 15 to 20° C. for 3 hours using 5% rhodium carbon (5.80 g) in ethyl acetate (232 mL). The catalyst was filtered off through celite, and then, ethyl acetate was distilled off under reduced pressure to obtain the title compound (4-1-7) (25.73 g) as a white solid.

Compound (RE1):
4-[4-Bromo-3-(2-methoxyethoxy)benzyl]piperidine hydrochloride

A solution of the compound (4-1-7) (25.73 g, corresponding to 54.6 mmol) in 2-propanol (115 mL) was heated to an internal temperature of 55 to 60° C. Concentrated hydrochloric acid (36%, 23.2 mL) was added dropwise thereto in 5 minutes, and the reaction mixture was stirred at an internal temperature of 55 to 60° C. for 4 hours. After cooling to room temperature, 2-propanol was distilled off under reduced pressure to obtain a concentrated residue (42.91 g). The reaction mixture was separated into aqueous and organic layers by the addition of water (115 mL) and toluene (115 mL) thereto, and the organic layer was subjected to re-extraction with water (50 mL). The combined aqueous layer was adjusted to approximately pH 10 with sodium hydroxide and subjected to extraction with toluene (200+100+100 mL). The organic layer was washed with water (50 mL), and toluene was distilled off under reduced pressure to obtain a concentrated residue (18.57 g). This concentrated residue was dissolved in 2-propanol. To this solution, concentrated hydrochloric acid (36%, 5.58 g, 54.6 mmol) was added at room temperature, and 2-propanol was distilled off under reduced pressure. 2-Propanol (200 mL×2) was added to the concentrated residue, and 2-propanol was distilled off under reduced pressure to obtain a concentrated residue (18.61 g) as a white powder. 2-Propanol (115 mL) was added thereto. After confirmation by visual observation that a uniform solution was obtained at an internal temperature around 65 to 70° C., the solution was slowly cooled. When the deposition of crystals was confirmed around 60° C., n-hexane (60 mL) was added dropwise thereto at an internal temperature of 55 to 60° C. in 20 minutes. The suspension was stirred at an internal temperature of 55 to 60° C. for 1 hour and then slowly cooled again. When the internal temperature reached 30° C. or lower, the reaction mixture was stirred for 1 hour with the internal temperature kept at 15 to 20° C. by water cooling, and further stirred for 1 hour at an internal temperature of 5° C. or lower under ice cooling. The precipitate was collected by filtration, and the residue was washed with a mixed solution of cold n-hexane (23 mL) and 2-propanol (12 mL) and then dried under reduced pressure to obtain the compound (RE1) of interest (17.30 g) as a white powder.

Melting point: 171-172° C.

$^1$H-NMR (300 MHz, CDCl$_3$) δ: 1.47-1.94 (5H, m), 2.55 (2H, d, J=5.5 Hz), 2.79 (2H, t like, J=12 Hz), 3.47 (2H, d like, J=13 Hz), 3.51 (3H, s), 3.81 (2H, t, J=4.8 Hz), 4.15 (2H, t, J=4.8 Hz), 6.62 (1H, dd, J=7.9, 1.8 Hz), 6.68 (1H, d, J=1.7 Hz), 7.43 (1H, d, J=8.1 Hz), 9.50 (2H, br s).

Reference Example 2

Compound (RE2):
2-[2-Bromo-5-(piperidin-4-ylmethyl)phenoxy]ethanol

[Formula 34]

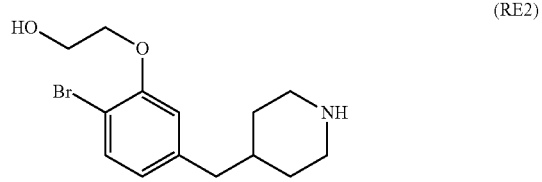

A solution of 4-[4-bromo-3-(2-methoxyethoxy)benzyl]piperidine hydrochloride (RE1) (3.00 g, 8.3 mmol) in dichloromethane (100 mL) was cooled in a salt-ice bath. A 1 M solution of boron tribromide in dichloromethane (7.8 mL, 7.8 mmol) was added dropwise thereto at 0° C. in 30 minutes, and the reaction mixture was stirred for 1.5 hours under ice cooling. Methanol (20 mL) was added thereto, and the solvent was distilled off under reduced pressure. A 5% aqueous potassium carbonate solution (50 mL) was added to the obtained concentrated residue, followed by extraction with chloroform. The organic layer was dried over anhydrous sodium sulfate. The solvent was distilled off under reduced pressure to obtain the title compound (RE2) (3.03 g, quantitative).

$^1$H-NMR (400 MHz,CDCl$_3$) δ: 1.15-1.30 (2H, m), 1.40-1.55 (1H, m), 1.55-1.70 (2H, m), 2.49 (2H, d, J=6.7 Hz), 2.58 (2H, dt, J=2.4, 12 Hz), 3.11 (2H, d like, J=12 Hz), 3.98 (2H, t, J=4.6 Hz), 4.14 (2H, t, J=4.6 Hz), 6.66 (1H, dd, J=8.0, 1.8 Hz), 6.70 (1H, d, J=1.8 Hz), 7.42 (1H, d, J=8.0 Hz).

Reference Example 3

Compound (RE3):
4-[4-Bromo-3-(methoxymethoxy)benzyl]piperidine

The compound was synthesized according to the following production method:
Production Method

[Formula 35]

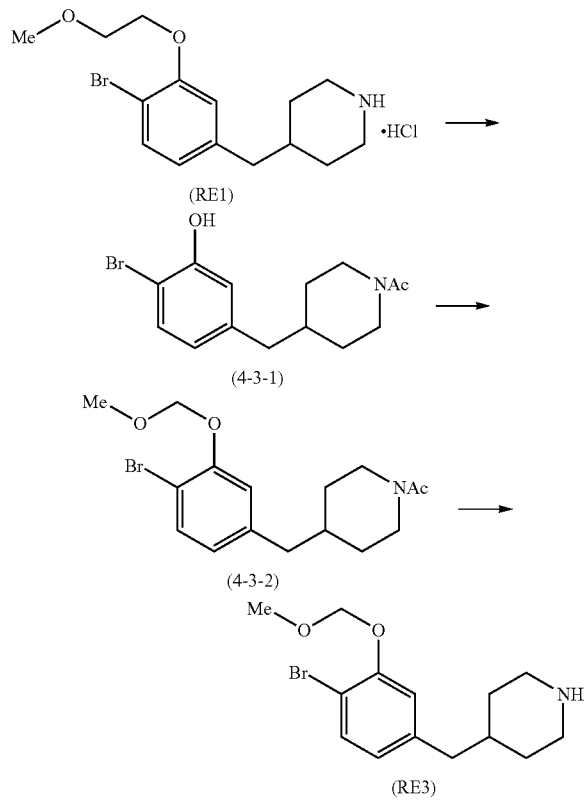

Compound (4-3-1): 1-[4-(4-Bromo-3-hydroxybenzyl)piperidin-1-yl]ethanone

A solution of 4-[4-bromo-3-(2-methoxyethoxy)benzyl]piperidine hydrochloride (RE1) (3.00 g (8.25 mmol) in dichloromethane (50 mL) was cooled in an ice bath. Boron tribromide (1.0 M solution in dichloromethane, 33 mL, 33 mmol) was added dropwise thereto in 1 hour, and the reaction solution was stirred overnight with gradual heating to room temperature. Methanol (10 mL) was added dropwise thereto in 30 minutes with cooling again in an ice bath, and the reaction mixture was warmed to room temperature. Then, the solvent was distilled off under reduced pressure. A 10% aqueous potassium carbonate solution (75 mL) and 1,4-dioxane (75 mL) were added to the concentrated residue without further purifying it. A solution of acetic anhydride (785 µL, 8.3 mmol) in 1,4-dioxane (15 mL) was added dropwise thereto at room temperature over 1 hour with vigorous stirring, and the reaction mixture was stirred for 1 hour in this state. Water (300 mL) was added thereto, followed by extraction with ethyl acetate. The organic layer was washed with a 0.5 N aqueous hydrochloric acid solution and brine. The organic layer was dried over anhydrous magnesium sulfate, and then the solvent was distilled off under reduced pressure. The obtained concentrated residue was suspended by the addition of n-hexane/ethyl acetate (2:1, 30 mL), and the resulting precipitate was collected by filtration, washed with n-hexane/ethyl acetate (2:1, 3 mL×2), and then dried under reduced pressure to obtain the title compound (4-3-1) (2.05 g, 80%) as a light brown powder.

Compound (4-3-2): 1-{4-[4-Bromo-3-(methoxymethoxy)benzyl]piperidin-1-yl}ethanone Chloromethyl methyl ether (735 µL, 9.7 mmol) was added to a solution of the compound (4-3-1) (2.00 g, 6.4 mmol) and potassium carbonate (1.80 g, 13 mmol) in dimethylformamide (20 mL) at room temperature, and the reaction mixture was stirred for 3 days. Then, potassium carbonate (900 mg, 6.5 mmol) and chloromethyl methyl ether (370 µL, 4.3 mmol) were added thereto at room temperature, and the reaction mixture was stirred at room temperature for 3 hours. Water (100 mL) was added thereto, followed by extraction with toluene/ethyl acetate (1:2, 300 mL). The organic layer was washed with water, and then, the solvent was distilled off under reduced pressure. The obtained concentrated residue was purified by silica gel column chromatography (n-hexane/ethyl acetate) to obtain the title compound (4-3-2) (2.23 g, quantitative) as a pale yellow solid.

Compound (RE3):
4-[4-Bromo-3-(methoxymethoxy)benzyl]piperidine

A solution of the compound (4-3-2) (2.20 g, 6.4 mmol) in a 4 N aqueous sodium hydroxide solution (30 mL), 1,4-dioxane (30 mL) and ethanol (15 mL) was heated under reflux for 2.5 days. 1,4-Dioxane and ethanol were distilled off under reduced pressure, and water (100 mL) was added to the concentrated residue, followed by extraction with toluene (150 mL×3). The organic layer was dried over anhydrous sodium sulfate, and then, the solvent was distilled off under reduced pressure to obtain the compound (RE3) of interest (1.97 g, 98%) as a colorless crystalline solid.

$^1$H-NMR (300 MHz,CDCl$_3$) δ: 1.07-1.19 (2H, m), 1.53-1.63 (3H, m), 2.47 (2H, d, J=6.8 Hz), 2.48-2.60 (2H, m), 2.99-3.09 (2H, m), 3.53 (3H, s), 5.24 (2H, s), 6.68 (1H, dd, J=8.1, 1.8 Hz), 6.93 (1H, d, J=1.8 Hz), 7.42 (1H, d, J=8.1 Hz).

Reference Example 4

Compound (RE4): 2-Bromo-5-(piperidin-4-ylmethyl)phenol

[Formula 36]

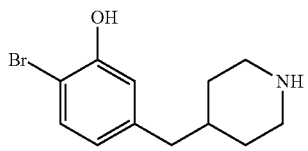
(RE4)

A solution of tert-butyl 4-(4-bromo-3-hydroxybenzyl)piperidine-1-carboxylate (4-5-1) (1.20 g, 3.2 mmol) in 10% hydrogen chloride and methanol (30 mL) was stirred at room temperature for 3.5 hours. The solvent was distilled off under reduced pressure. Then, the obtained concentrated residue was adjusted to pH 8 by the addition of a saturated aqueous solution of sodium bicarbonate, and then water was distilled off under reduced pressure. The obtained concentrated residue was suspended by the addition of water (30 mL), and the resulting precipitate was collected by filtration, washed with water (1 mL), and then dried under reduced pressure to obtain the title compound (RE4) (787 mg, 90%) as a white powder.

$^1$H-NMR (300 MHz, DMSO-d6) δ: 0.86-1.09 (2H, m), 1.36-1.57 (3H, m), 2.24-2.43 (4 H, m), 2.77-2.95 (2H, m), 6.48 (1H, dd, J=8.1, 1.8 Hz), 6.71 (1H, d, J=1.8 Hz), 7.30 (1H, d, J=8.1 Hz).

Reference Example 5

Compound (RE5): tert-Butyl [2-bromo-5-(piperidin-4-ylmethyl)phenoxy]acetate

The compound was synthesized according to the following production method:
Production Method

[Formula 37]

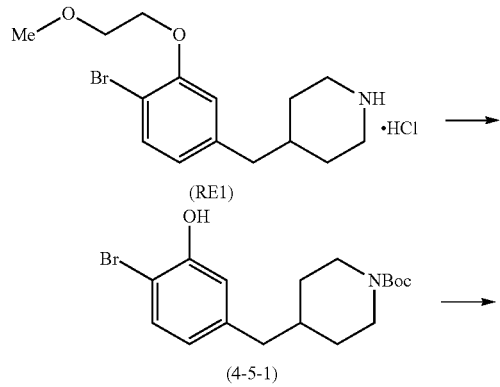

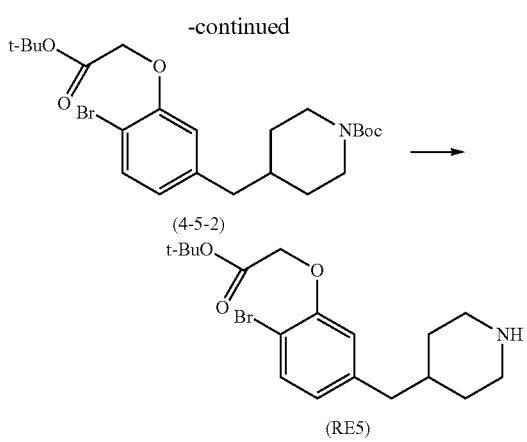

Compound (4-5-1): tert-Butyl 4-(4-bromo-3-hydroxybenzyl)piperidine-1-carboxylate A solution of 4-[4-bromo-3-(2-methoxyethoxy)benzyl]piperidine hydrochloride (RE1) (5.00 g (13.8 mmol) in dichloromethane (100 mL) was cooled in an ice bath. Boron tribromide (1.0 M solution in dichloromethane, 55 mL, 55 mmol) was added dropwise thereto in 35 minutes, and the reaction solution was stirred for 1 day with gradual heating to room temperature. Methanol (20 mL) was added dropwise thereto in 20 minutes with cooling again in an ice bath, and the reaction mixture was warmed to room temperature. Then, the solvent was distilled off under reduced pressure. A 10% aqueous potassium carbonate solution (100 mL) and 1,4-dioxane (100 mL) were added to the concentrated residue without further purifying it. A solution of Boc$_2$O (3.00 g, 13.8 mmol) in 1,4-dioxane (20 mL) was added dropwise thereto at room temperature over 30 minutes with vigorous stirring, and the reaction mixture was stirred overnight in this state. 1,4-Dioxane was distilled off under reduced pressure. Then, the concentrated residue was subjected to extraction with ethyl acetate, and the organic layer was washed with brine. The organic layer was dried over anhydrous magnesium sulfate, and then, the solvent was distilled off under reduced pressure. The obtained concentrated residue was suspended by the addition of n-hexane/ethyl acetate (2:1, 20 mL), and the resulting precipitate was collected by filtration, washed with n-hexane/ethyl acetate (2:1, 5 mL×2), and then dried under reduced pressure to obtain the title compound (4-5-1) (4.25 g, 83%) as a white powder.

Compound (4-5-2): tert-Butyl 4-[4-bromo-3-(2-tert-butoxy-2-oxoethoxy)benzyl]piperidine-1-carboxylate Bromoacetic acid t-butyl ester (1.35 mL, 10 mmol) was added to a suspension of the compound (4-5-1) (3.50 g, 9.5 mmol) and potassium carbonate (2.62 g, 19 mmol) in acetonitrile (70 mL) at room temperature, and the reaction mixture was stirred at room temperature for 3 nights. Water (200 mL) was added thereto, followed by extraction with ethyl acetate. The organic layer was washed with brine and then dried over anhydrous magnesium sulfate. The solvent was distilled off under reduced pressure, and then, the obtained concentrated residue was purified by silica gel column chromatography (n-hexane:ethyl acetate=2:1) to obtain the title compound (4-5-2) (4.24 g, 92%) as a white solid.

Compound (RE5): tert-Butyl [2-bromo-5-(piperidin-4-ylmethyl)phenoxy]acetate

A 4 N solution of hydrogen chloride in 1,4-dioxane (40 mL) was added to a solution of the compound (4-5-2) (4.20 g, 9.0 mmol) in 1,4-dioxane (5 mL) at room temperature, and the reaction mixture was stirred at room temperature for 20 minutes and then poured to a suspension of sodium bicarbonate (20 g) in water (200 mL), followed by extraction with chloroform. The organic layer was dried over anhydrous sodium sulfate, and then, the solvent was distilled off under reduced pressure to obtain the compound (RE5) of interest (2.34 g, 70%) as a white solid.

$^1$H-NMR (300 MHz, CDCl$_3$) δ: 1.09-1.17 (2H, m), 1.42-1.66 (3H, m), 1.48 (9H, s), 2.45 (2H, d, J=6.8 Hz), 2.46-2.60 (2H, m), 2.97-3.10 (2 H, m), 4.59 (2H, s), 6.56 (1H, d, J=1.7 Hz), 6.66 (1H, dd, J=8.1, 1.7 Hz), 7.43 (1H, d, J=8.1 Hz).

Reference Example 6

Compound (RE6): 2-(4-Oxo-3,4-dihydro-2H-chromen-6-yl)ethyl 4-methylbenzenesulfonate The compound was synthesized according to the following production method:
Production Method

[Formula 38]

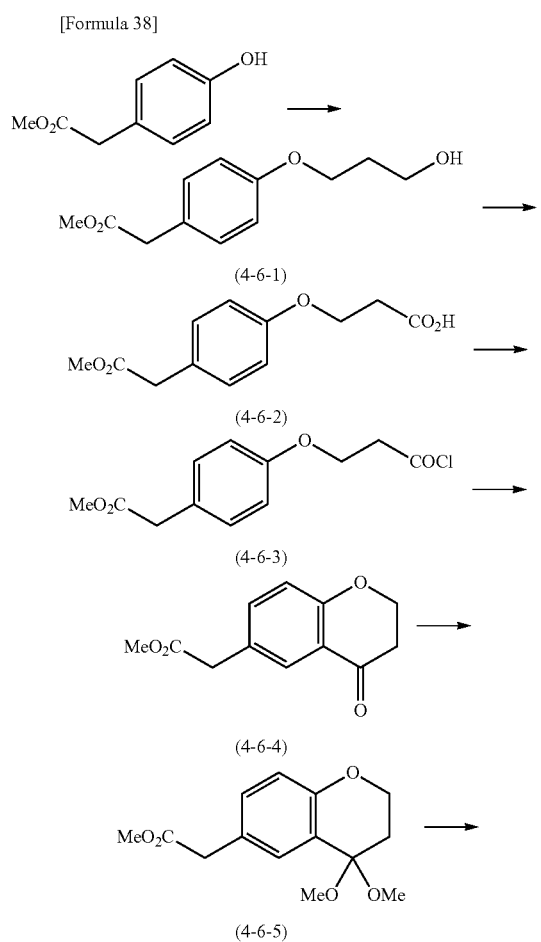

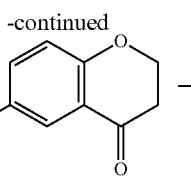

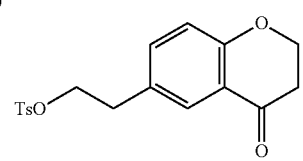

(RE6)

Compound (4-6-1): Methyl [4-(3-hydroxypropoxy)phenyl]acetate

Potassium carbonate (91.5 g, 662 mmol) and 3-bromo-1-propanol (35.3 mL, 391 mmol) were added in this order to a solution of 4-hydroxyphenylacetic acid methyl ester (50.0 g, 301 mmol) in acetonitrile (1000 mL) and water (10 mL) at room temperature, and the reaction mixture was heated under reflux for 3 hours. After cooling to room temperature, the salt was collected by filtration, and the residue was washed with acetonitrile (50 mL×2). The filtrate was concentrated under reduced pressure, and the obtained concentrated residue was separated into aqueous and organic layers by the addition of toluene (500 mL) and water (250 mL). The aqueous layer was subjected to re-extraction with toluene (125 mL×2), and combined organic layers were washed with a 0.5 N aqueous sodium hydroxide solution (100 mL) and a 1% aqueous potassium bisulfate solution (100 mL). The organic layer was dried over anhydrous magnesium sulfate, and then, the solvent was distilled off under reduced pressure to obtain the title compound (4-6-1) (70.2 g) as a yellow oil.

Compound (4-6-2): 3-[4-(2-Methoxy-2-oxoethyl) phenoxy]propanoic acid

A 0.25 M aqueous potassium dihydrogen phosphate solution (400 mL), a 0.25 M aqueous disodium hydrogen phosphate solution (400 mL), 80% sodium chlorite (54.5 g, 482 mmol), and a 5% aqueous sodium hypochlorite solution (6.52 mL, 4.82 mmol) were added in this order to a solution of 2,2,6,6-tetramethyl-1-piperidinyloxy radical (TEMPO) (4.71 g, 30.1 mmol) in acetonitrile (160 mL). Subsequently, a solution of the compound (4-6-1) (56.2 g, corresponding to 241 mmol) in acetonitrile (800 mL) was added dropwise thereto in approximately 1 hour with the internal temperature kept at 20 to 25° C. by water cooling. The reaction mixture was stirred for 2 hours in this state. Then, a 20% aqueous sodium bisulfite solution (400 mL) was added dropwise thereto in 30 minutes with the internal temperature kept at 15° C. or lower in an ice bath, and the solution was gradually warmed to room temperature. Acetonitrile was distilled off under reduced pressure. Water (400 mL) was added thereto, and the mixture was stirred at room temperature for 30 minutes. The resulting precipitate was collected by filtration and washed with water (100 mL×2). The residue was dissolved in ethyl acetate (400 mL). The solution was washed with brine (100 mL) and dried over anhydrous sodium sulfate, and then, the solvent was distilled off under reduced pressure to obtain the title compound (4-6-2) (47.87 g).

Compound (4-6-3): Methyl [4-(3-chloro-3-oxopropoxy)phenyl]acetate

Thionyl chloride (42.7 mL, 592 mmol) was added to a solution of the compound (4-6-2) (47.0 g, 197 mmol) in toluene (470 mL) at room temperature, and the reaction mixture was stirred at 60° C. for 3 hours. After cooling to room temperature, toluene was distilled off to obtain the title compound (4-6-3) (56.52 g) as a pale yellow oil.

Compound (4-6-4): Methyl (4-oxo-3,4-dihydro-2H-chromen-6-yl)acetate

A solution of the compound (4-6-3) (56.52 g, corresponding to 197 mmol) in dichloromethane (140 mL) was added dropwise to a solution of aluminum chloride (52.5 g, 394 mmol) in dichloromethane (330 mL) in 30 minutes with the internal temperature kept at 20 to 25° C. by water cooling, and the reaction mixture was stirred for 1.5 hours in this state. The reaction mixture was cooled, and a 2 N aqueous hydrochloric acid solution (470 mL) was added thereto with the internal temperature kept at 15° C. or lower by cooling in an ice bath. The reaction mixture was warmed to room temperature and then separated into aqueous and organic layers. The aqueous layer was subjected to re-extraction with chloroform (120 mL). Combined organic layers were washed with water (240 mL) and a saturated aqueous solution of sodium bicarbonate (240 mL) in this order and dried over anhydrous magnesium sulfate, and then, the solvent was distilled off under reduced pressure to obtain the title compound (4-6-4) (38.91 g) as a brown solid.

Compound (4-6-5): Methyl (4,4-dimethoxy-3,4-dihydro-2H-chromen-6-yl)acetate p-Toluenesulfonic acid monohydrate (3.02 g, 15.9 mmol) and methyl orthoformate (210 mL) were added to a solution of the compound (4-6-4) (35.0 g, 159 mmol) in methanol (105 mL), and the reaction mixture was stirred at room temperature (15 to 20° C.) for 20 hours. The reaction solution was added dropwise to a 5% aqueous sodium bicarbonate solution (175 mL) in 15 minutes with the internal temperature kept at 15° C. or lower by ice cooling, and the reaction mixture was separated into aqueous and organic layers by the addition of toluene (175 mL) and water (88 mL). The aqueous layer was subjected to re-extraction with toluene (88 mL), and combined organic layers were washed with water (44 mL) and then dried over anhydrous sodium sulfate. The solvent was distilled off to obtain the title compound (4-6-5) (46.49 g) as a yellow oil.

Compound (4-6-6): 6-(2-Hydroxyethyl)-2,3-dihydro-4H-chromen-4-one

A solution of the compound (4-6-5) (46.0 g, corresponding to 159 mmol) in THF (90 mL) was added dropwise to a suspension of lithium aluminum hydride (9.05 g, 239 mmol) in THF (600 mL) in 30 minutes with the internal temperature kept at 30° C. or lower by water cooling, and the reaction mixture was stirred for 1 hour in this states. THF-water (1:2, 12 mL) was added dropwise thereto with the internal temperature kept at 15° C. or lower by ice cooling (stirring was made difficult to perform due to deposited insoluble matter during the course of this operation). Subsequently, a 3 N aqueous hydrochloric acid solution (460 mL) was added dropwise thereto with the internal temperature kept at 15° C. or lower. The reaction mixture was stirred at 20 to 25° C. for 1.5 hours in this state and separated into aqueous and organic layers by the addition of toluene (460 mL). The aqueous layer was subjected to re-extraction with toluene (230 mL). Combined organic layers were washed with a 3 N aqueous hydrochloric acid solution (230 mL×2) and dried over anhydrous magnesium sulfate, and then, the solvent was distilled off under reduced pressure to obtain the title compound (4-6-6) (30.0 g) as a colorless oil.

Compound (RE6): 2-(4-Oxo-3,4-dihydro-2H-chromen-6-yl)ethyl 4-methylbenzenesulfonate Trimethylamine hydrochloride (497 mg, 5.20 mmol) and triethylamine (14.4 mL, 104 mmol) were added to a solution of the compound (4-6-6) (10.0 g, corresponding to 52 mmol) in acetonitrile (150 mL). p-Toluenesulfonyl chloride (11.9 g, 62.4 mmol) was added thereto in small portions at an internal temperature of 15° C. or lower under cooling in an ice bath, and the reaction mixture was stirred at an internal temperature of 5° C. or lower for 1.5 hours. A 5% aqueous sodium bicarbonate solution (75 mL) was added thereto at an internal temperature of 10° C. or lower, and the reaction mixture was warmed to room temperature and then separated into aqueous and organic layers by the addition of toluene (75 mL). The aqueous layer was subjected to re-extraction with toluene (75 mL). Combined organic layers were washed with a 1% aqueous potassium bisulfate solution (38 mL×2) and dried over anhydrous magnesium sulfate, and then, the solvent was distilled off under reduced pressure to obtain a concentrated residue (16.61 g). Toluene (50 mL) was added thereto, and the mixture was stirred at 50° C. for 1.5 hours and subsequently cooled to room temperature (20 to 25° C.) in 30 minutes. The reaction mixture was stirred at an internal temperature of 20 to 25° C. for 1 hour under water cooling, and then, the precipitate was collected by filtration, washed with toluene (10 mL×2), and dried under reduced pressure to obtain the compound (RE6) of interest (10.65 g) as a pale yellow powder.

Melting point: 121-122° C.

$^3$H-NMR (300 MHz,CDCl$_3$) δ: 2.44 (3H, s), 2.79 (2H, t, J=6.5 Hz), 2.91 (2H, t, J=6.9 Hz), 4.18 (2H, t, J=6.9 Hz), 4.51 (2H, t, J=6.4 Hz), 6.88 (1H, d, J=8.4 Hz), 7.26 (1H, dd, J=8.5, 2.5 Hz), 7.30 (2H, d, J=8.5 Hz), 7.60 (1H, d, J=2.2 Hz), 7.71 (2H, d, J=8.3 Hz).

Reference Example 7

Compound (RE7): 2-(4-Oxo-4H-chromen-6-yl)ethyl 4-methylbenzenesulfonate

[Formula 39]

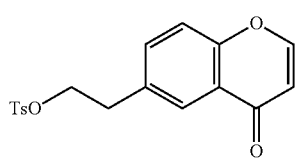

(RE7)

The compound was produced with reference to the method described in the literature (Synth. Commun., 1994, 24 (18), 2637). A solution of 2-(4-oxo-3,4-dihydro-2H-chromen-6-yl)ethyl 4-methylbenzenesulfonate (RE6) (15.0 g, 43 mmol), [hydroxy(tosyloxy)iodo]benzene (20.4 g, 52 mmol) and p-toluenesulfonic acid monohydrate (375 mg) in acetonitrile (750 mL) was stirred at 50° C. for 16 hours. The solvent was distilled off under reduced pressure. Ethyl acetate (500 mL) was added to the obtained concentrated residue, and the organic layer was washed with a saturated aqueous solution of sodium bicarbonate and brine in this order and dried over anhydrous magnesium sulfate. The solvent was distilled off under reduced pressure, and the obtained concentrated residue was purified by silica gel column chromatography (n-hexane:ethyl acetate=1:1→1:2) to obtain the title compound (RE7) (4.92 g, 33%) as a pale yellow solid.

¹H-NMR (300 MHz,CDCl₃) δ: 3.05 (2H, t, J=6.7 Hz), 4.25 (2H, t, J=6.7 Hz), 6.33 (1H, d, J=6.1 Hz), 7.25 (2H, d, =8.1 Hz), 7.37 (1H, d, J=8.6 Hz), 7.48 (1H, dd, J=8.6, 2.4 Hz), 7.66 (2H, d, J=8.3 Hz), 7.85 (2H, d, J=6.1 Hz), 7.88 (2H, d, J=1.8 Hz).

Reference Example 8

Compound (RE8): 2-(3-Hydroxy-4,4-dimethoxy-3,4-dihydro-2H-chromen-6-yl)ethyl 4-methylbenzenesulfonate

[Formula 40]

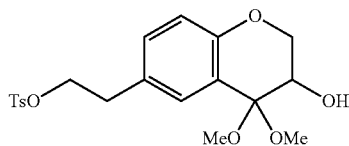

(RE8)

A suspension of 2-(4-oxo-3,4-dihydro-2H-chromen-6-yl) ethyl 4-methylbenzenesulfonate (RE6) (10.0 g, 29 mmol) in methanol (200 mL) was added to a solution of potassium hydroxide (4.86 g, 87 mmol) in methanol (100 mL) under ice cooling. To the reaction mixture, diacetoxyiodobenzene (10.2 g, 32 mmol) was added in small portions for 5 minutes with the temperature kept at 5° C. or lower, and the reaction mixture was gradually warmed to room temperature and stirred for 1 day. Bisacetoxyiodobenzene (2.00 g, 6.2 mmol) was further added thereto at room temperature, and the mixture was stirred for 3 hours. Then, methanol was distilled off under reduced pressure. Water (100 mL) was added to the obtained concentrated residue, followed by extraction with ethyl acetate. The organic layer was washed with brine and dried over anhydrous magnesium sulfate. The solvent was distilled off under reduced pressure. Then, the obtained concentrated residue was suspended by the addition of diethyl ether (50 mL), and the resulting precipitate was collected by filtration, washed with diethyl ether (5 mL×2), and then dried under reduced pressure to obtain the title compound (RE8) (8.99 g, 76%) as a white powder.

¹H-NMR (300 MHz,CDCl₃) δ: 2.00 (1H, dd, J=4.6, 0.9 Hz), 2.44 (3H, s), 2.91 (2H, t, J=7.1 Hz), 3.12 (3H, s), 3.42 (3H, s), 4.02-4.08 (1H, m), 4.10-4.24 (2H, m), 4.26-4.33 (1H, m), 4.36 (1H, dd, J=11.9, 2.8 Hz), 6.77 (1H, d, J=8.3 Hz), 6.99 (1H, dd, J=8.4, 2.4 Hz), 7.30 (2H, t, J=4.3 Hz), 7.35 (1H, d, J=2.0 Hz), 7.71 (2H, d, J=8.4 Hz).

Reference Example 9

Compound (RE9): 6-(Oxiran-2-yl)-2,3-dihydro-4H-chromen-4-one

The compound was synthesized according to the following production method:
Production Method

[Formula 41]

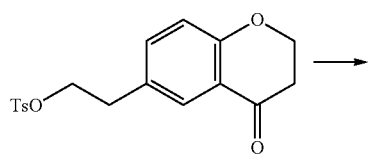

(RE6)

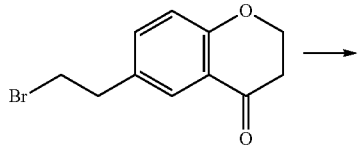

(4-9-1)

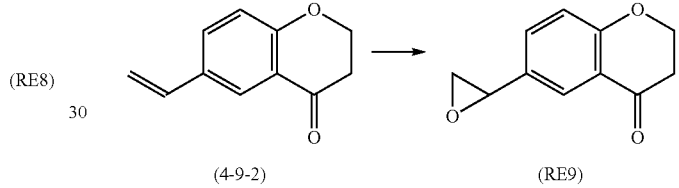

(4-9-2)                    (RE9)

Compound (4-9-1): 6-(2-Bromoethyl)-2,3-dihydro-4H-chromen-4-one

A solution of 2-(4-oxo-3,4-dihydro-2H-chromen-6-yl) ethyl 4-methylbenzenesulfonate (RE6) (700 mg, 2.0 mmol) and lithium bromide (877 mg, 10 mmol) in dimethylformamide (10 mL) was stirred at 50° C. for 1 hour. Water (50 mL) was added thereto, followed by extraction with ethyl acetate (40 mL). After addition of toluene (40 mL), the organic layer was washed with water (30 mL). The organic layer was dried over anhydrous magnesium sulfate, and then, the solvent was distilled off under reduced pressure to obtain the title compound (4-9-1) (551 mg, quantitative).

Compound (4-9-2): 6-Ethenyl-2,3-dihydro-4H-chromen-4-one

A solution of the compound (4-9-1) and DBU (2.3 mL, 15.6 mmol) in toluene (10 mL) was stirred at room temperature for 16 hours. To the reaction mixture, water (50 mL) was added, followed by extraction with ethyl acetate (50 mL×2). Combined organic layers were dried over anhydrous magnesium sulfate, and then, the solvent was distilled off under reduced pressure. The obtained concentrated residue was purified by silica gel column chromatography (n-hexane: ethyl acetate=3:1) to obtain the title compound (4-9-2) (334 mg, 80%) as a colorless oil.

Compound (RE9): 6-(Oxiran-2-yl)-2,3-dihydro-4H-chromen-4-one m-Chloroperbenzoic acid (65%, 393 mg, 1.5 mmol) was added to a solution of the compound (4-9-2) (258 mg, 1.5 mmol) in dichloromethane (7 mL) at room temperature, and the reaction mixture was stirred at room temperature for 1 hour. A saturated aqueous solution of sodium bicarbonate (30 mL) was added thereto, followed by extraction with chloroform (20 mL×2). The organic layer was dried over anhydrous sodium sulfate, and then, the solvent was distilled off under reduced pressure. The obtained concentrated residue was purified by silica gel column chromatography (n-hexane:ethyl acetate=3:1) to obtain the compound (RE9) of interest (230 mg) as a colorless oil.

$^1$H-NMR (300 MHz, CDCl$_3$): 7.86 (d, J=2.3 Hz, 1H, Ar), 7.35 (dd, J=2.3, 8.6 Hz, 1H, Ar), 6.97 (d, J=8.6 Hz, 1H, Ar), 4.54 (t, J=6.4 Hz, 2H, CH$_2$), 3.85 (dd, J=2.6, 4.0 Hz, 1H, CH), 3.14 (dd, J=4.0, 5.3 Hz, 1H, CH), 2.85-2.78 (m, 3H).

Example 1

Compound (5-1): 6-(2-{4-[4-Bromo-3-(2-methoxyethoxy)benzyl]piperidin-1-yl}ethyl)-3,4-dihydro-2H-chromen-4-ol benzenesulfonate (salt)

The compound was synthesized according to the following production method:
Production Method

[Formula 42]

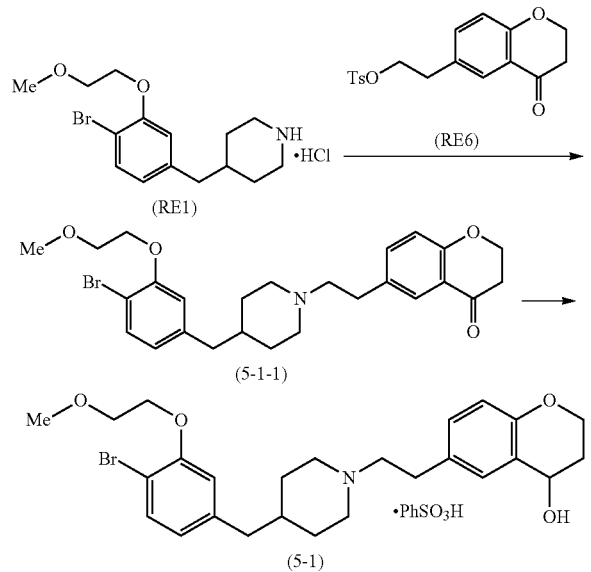

Compound (5-1-1): 6-(2-{4-[4-Bromo-3-(2-methoxyethoxy)benzyl]piperidin-1-yl}ethyl)-2,3-dihydro-4H-chromen-4-one 4-[4-Bromo-3-(2-methoxyethoxy)benzyl]piperidine hydrochloride (RE1) (52.0 g, 143 mmol) was added to a 5% aqueous potassium carbonate solution (350 mL), followed by extraction with toluene (700 mL×3). Combined organic layers were dried over anhydrous sodium sulfate, and the solvent was distilled off under reduced pressure to obtain 4-[4-bromo-3-(2-methoxyethoxy)benzyl]piperidine (48.1 g). Next, a solution of 4-[4-bromo-3-(2-methoxyethoxy)benzyl]piperidine (2.00 g, 6.1 mmol), 2-(4-oxo-3,4-dihydro-2H-chromen-6-yl)ethyl 4-methylbenzenesulfonate (RE6) (2.01 g, 5.8 mmol) and potassium carbonate (1.66 g, 12 mmol) in acetonitrile (20 mL) was stirred at 70 to 80° C. for 7 hours. After cooling to room temperature, water (100 mL) was added thereto, followed by extraction with chloroform. The chloroform layer was dried over anhydrous sodium sulfate. The solvent was distilled off under reduced pressure, and then, the obtained concentrated residue was purified by silica gel column chromatography (n-hexane:ethyl acetate=1:1→chloroform:methanol=20:1) to obtain the title compound (5-1-1) (3.07 g, quantitative).

Compound (5-1): 6-(2-{4-[4-Bromo-3-(2-methoxyethoxy)benzyl]piperidin-1-yl}ethyl)-3,4-dihydro-2H-chromen-4-ol benzenesulfonate (salt)

Sodium borohydride (38 mg, 1.0 mmol) was added to a solution of the compound (5-1-1) (502 mmol, 1.0 mmol) in methanol (10 mL) under ice cooling, and the reaction mixture was stirred for 1.5 hours under ice cooling in this state. Water (30 mL) was added thereto, followed by extraction with chloroform. The organic layer was dried over anhydrous sodium sulfate. Then, the solvent was distilled off under reduced pressure, and the obtained concentrated residue was purified by silica gel column chromatography (n-hexane/ethyl acetate→chloroform/methanol) to obtain free amine of the title compound (412 mg). This free amine was dissolved in acetone (10 mL). To this solution, benzenesulfonic acid monohydrate (140 mg, 0.79 mmol) was added at room temperature. After confirmation of dissolution, the solvent was distilled off under reduced pressure. The obtained concentrated residue was suspended by the addition of diethyl ether (50 mL), and the resulting precipitate was collected by filtration, washed with diethyl ether (5 mL×2), and dried under reduced pressure to obtain the compound (5-1) of interest (425 mg, 64%) as a white powder.

$^1$H-NMR (300 MHz, DMSO-d6) δ: 1.53-2.22 (7H, m), 2.45 (2H, d, J=6.8 Hz), 2.50-2.70 (2H, m), 2.88-3.23 (4H, m), 3.49 (3H, s), 3.52-3.69 (2H, m), 3.80 (2H, t, J=4.8 Hz), 4.14 (2H, t, J=4.8 Hz), 4.17-4.29 (2H, m), 4.71 (1H, t, J=4.3 Hz), 6.55 (1H, dd, J=7.9, 1.8 Hz), 6.63 (1H, d, J=1.7 Hz), 6.70 (1H, d, J=8.3 Hz), 6.92 (1H, dd, J=8.4, 2.2 Hz), 7.33-7.48 (5H, m), 7.86-7.95 (2H, m), 10.14 (1H, br s).

Example 2

Compound (5-2): 6-(2-{4-[4-Bromo-3-(2-hydroxyethoxy)benzyl]piperidin-1-yl}ethyl)-3,4-dihydro-2H-chromen-4-ol The compound was synthesized according to the following production method:
Production Method

[Formula 43]

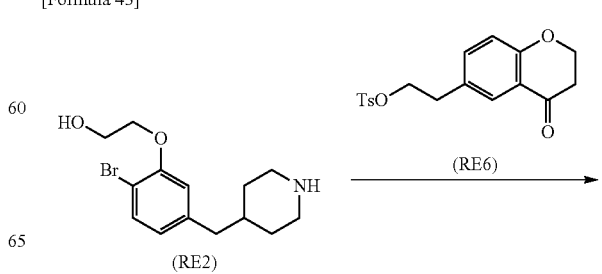

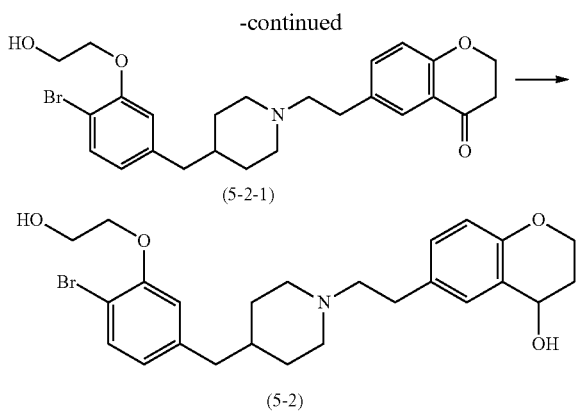

(5-2-1)

(5-2)

Compound (5-2-1): 6-(2-{4-[4-Bromo-3-(2-hydroxyethoxy)benzyl]piperidin-1-yl}ethyl)-3,4-dihydro-2H-chromen-4-on A solution of 2-[2-bromo-5-(piperidin-4-ylmethyl)phenoxy]ethanol (1.70 g, 5.5 mmol) (RE2), 2-(4-oxo-3,4-dihydro-2H-chromen-6-yl)ethyl 4-methylbenzenesulfonate (RE6) (1.98 g, 5.7 mmol) and potassium carbonate (1.57 g, 11 mmol) in acetonitrile (40 mL) was heated under reflux for 3.5 hours. After cooling to room temperature, water (100 mL) was added thereto, followed by extraction with chloroform. The chloroform layer was dried over anhydrous sodium sulfate. The solvent was distilled off under reduced pressure, and then, the obtained concentrated residue was purified by silica gel column chromatography (n-hexane/ethyl acetate→chloroform/methanol) to obtain the title compound (5-2-1) (2.21 g, 83%) as a colorless oil.

Compound (5-2): 6-(2-{4-[4-Bromo-3-(2-hydroxyethoxy)benzyl]piperidin-1-yl}ethyl)-3,4-dihydro-2H-chromen-4-ol Sodium borohydride (171 mg, 4.5 mmol) was added to a solution of the compound (5-2-1) (2.20 g, 4.5 mmol) in methanol (40 mL) under ice cooling, and the reaction mixture was stirred for 30 minutes in this state. Water (80 mL) was added thereto, and the mixture was gradually warmed to room temperature and subjected to extraction with chloroform. The organic layer was dried over anhydrous sodium sulfate, and then, the solvent was distilled off under reduced pressure. The obtained concentrated residue was purified by silica gel column chromatography (chloroform/methanol) to obtain the compound (5-2) of interest (1.54 g, 70%) as a colorless foamy solid.

$^1$H-NMR (300 MHz,CDCl$_3$) δ: 1.25-1.42 (2H, m), 1.42-1.57 (1H, m), 1.59-1.70 (2H, m), 1.89-2.19 (4H, m), 2.50 (2H, d, J=7.0 Hz), 2.52-2.61 (2H, m), 2.67-2.80 (2H, m), 2.92-3.06 (2H, m), 3.93-4.03 (2 H, m), 4.10-4.18 (2H, m), 4.19-4.31 (2H, m), 4.76 (1H, t, J=4.0 Hz), 6.66 (1H, dd, J=8.1, 1.8 Hz), 6.71 (1H, d, J=1.7 Hz), 6.76 (1H, d, J=8.3 Hz), 7.03 (1H, dd, J=8.4, 2.2 Hz), 7.14 (1H, d, J=2.2 Hz), 7.42 (1H, d, J=7.9 Hz).

Example 3

Compound (5-3): 6-(2-{4-[4-Bromo-3-(2-methoxyethoxy)benzyl]piperidin-1-yl}ethyl)-3-hydroxy-2,3-dihydro-4H-chromen-4-one hydrochloride The compound was synthesized according to the following production method:

Production Method

[Formula 44]

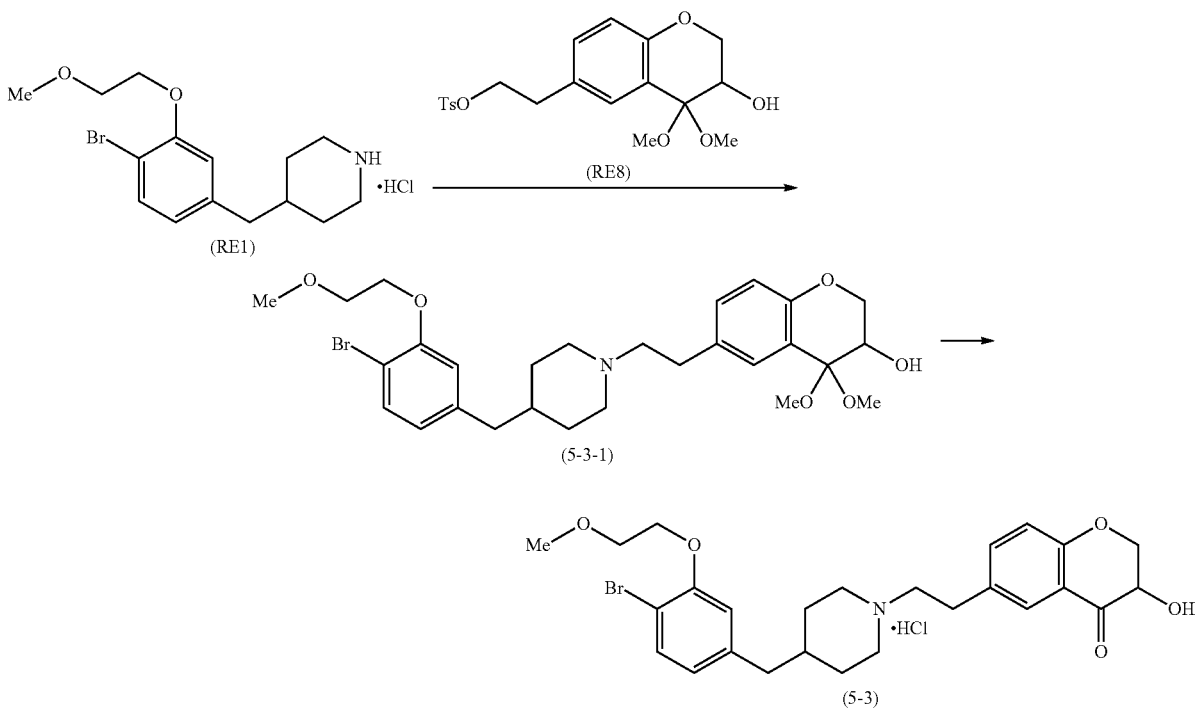

Compound (5-3-1): 6-(2-{4-[4-Bromo-3-(2-methoxyethoxy)benzyl]piperidin-1-yl}ethyl)-4,4-dimethoxy-3,4-dihydro-2H-chromen-3-ol The compound (RE1) was converted to a free form in the same way as in Example 1, and a suspension of this 4-[4-bromo-3-(2-methoxyethoxy)benzyl]piperidine (3.00 g, 9.2 mmol), 2-(3-hydroxy-4,4-dimethoxy-3,4-dihydro-2H-chromen-6-yl)ethyl 4-methylbenzenesulfonate (RE8) (3.75 g, 9.2 mmol) and potassium carbonate (2.54 g, 18 mmol) in acetonitrile (30 mL) was heated under reflux for 3 hours. After cooling to room temperature, water (100 mL) was added thereto, followed by extraction with chloroform. The organic layer was dried over anhydrous sodium sulfate. The solvent was distilled off under reduced pressure, and then, the obtained concentrated residue was purified by silica gel column chromatography (chloroform/methanol) to obtain the title compound (5-3-1) (4.46 g) as a colorless oil.

Compound (5-3): 6-(2-{4-[4-Bromo-3-(2-methoxyethoxy)benzyl]piperidin-1-yl}ethyl)-3-hydroxy-2,3-dihydro-4H-chromen-4-one hydrochloride The compound (5-3-1) (4.46 g, mmol) was dissolved in methanol (450 mL). To this solution, a 1 N aqueous hydrochloric acid solution (100 mL) was added dropwise at room temperature over 10 minutes. Methanol was distilled off under reduced pressure, and a saturated aqueous solution of sodium carbonate was added to the concentrated residue, followed by extraction with chloroform. The organic layer was dried over anhydrous sodium sulfate, and then, the solvent was distilled off under reduced pressure. The obtained concentrated residue was purified by silica gel column chromatography (chloroform/methanol) to obtain a free form of the title compound (3.80 g). This free form was dissolved in acetone (40 mL). To this solution, a 1 N solution of hydrogen chloride in diethyl ether (10 mL, 10 mmol) was added at room temperature, and the solvent was distilled off under reduced pressure. Acetone (50 mL) was added to the obtained concentrated residue, and the mixed solution was stirred at 50° C. for 1 hour and then stirred overnight with gradual cooling to room temperature. The resulting precipitate was collected by filtration and washed with acetone (4 mL×2), and then, the residue was dried under reduced pressure to obtain the compound (5-3) of interest (3.62 g, 71%) as a white powder.

Melting point: 155-160° C. (decomposed)

$^1$H-NMR (300 MHz, DMSO-d6) δ: 1.38-1.64 (2H, m), 1.65-2.06 (3H, m), 2.65 and 2.50 (2H, d, J=7.3 Hz), 2.77-2.95 (2H, m), 2.96-3.08(2H, m), 3.13-3.29 (2H, m), 3.44-3.60 (2H, m), 3.69 (2H, t, J=4.5 Hz), 4.12-4.27 (3H, m), 4.34-4.54 (2H, m), 6.01 and 6.03 (total 1H, d, J=5.0 Hz), 6.73 (1H, d, J=8.1), 6.94-7.08 (2H, m), 7.43-7.54 (2H, m), 7.67 and 7.71 (total 1H, d, J=2.2 Hz), 10.06 and 10.18 (total 1H, br s)

Example 4

Compound (5-4): 6-(2-{4-[4-Bromo-3-(2-hydroxyethoxy)benzyl]piperidin-1-yl}ethyl)-3-hydroxy-2,3-dihydro-4H-chromen-4-one The compound was synthesized according to the following production method:
Production Method

[Formula 45]

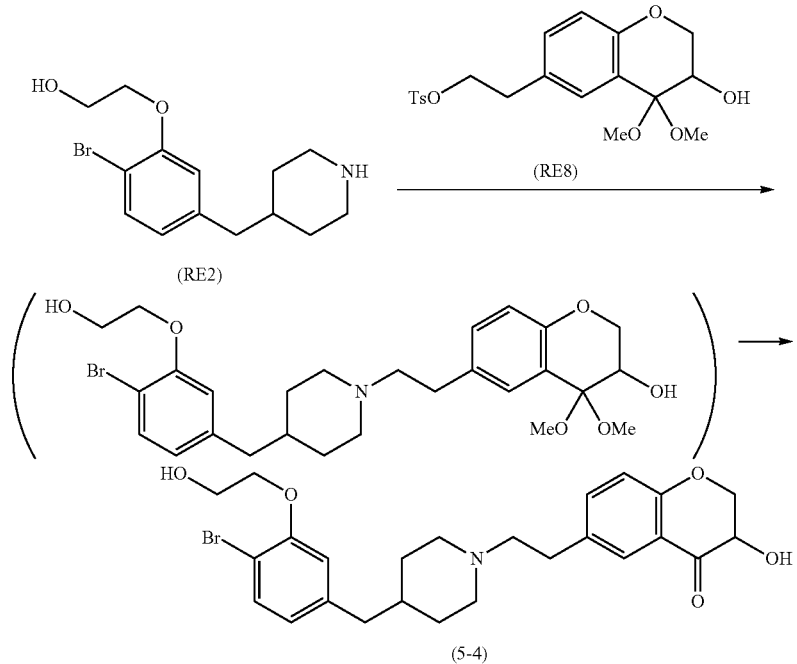

A suspension of 2-[2-bromo-5-(piperidin-4-ylmethyl)phenoxy]ethanol (RE2) (200 mg, 0.64 mmol), 2-(3-hydroxy-4,4-dimethoxy-3,4-dihydro-2H-chromen-6-yl)ethyl 4-methylbenzenesulfonate (RE8) (261 mg, 0.64 mmol) and potassium carbonate (179 mg, 1.3 mmol) in acetonitrile (4 mL) was heated under reflux for 2 hours. After cooling to room temperature, water was added thereto, followed by extraction with chloroform. The organic layer was dried over anhydrous sodium sulfate. The solvent was distilled off under reduced pressure, and then, the obtained concentrated residue was dissolved in methanol (4 mL). To this solution, a 1 N aqueous hydrochloric acid solution (2 mL) was added at room temperature, and the reaction mixture was stirred at room temperature for 2.5 hours. A saturated aqueous solution of sodium bicarbonate was added thereto, followed by extraction with chloroform. The organic layer was dried over anhydrous sodium sulfate. The solvent was distilled off under reduced pressure, and the obtained concentrated residue was purified by silica gel column chromatography (chloroform/methanol) to obtain the title compound (5-4) of interest (226 mg, 70%) as a colorless oil.

$^1$H-NMR (300 MHz,CDCl$_3$) δ: 1.21-1.41 (2H, m), 1.42-1.72 (3H, m), 1.88-2.03 (2H, m), 2.49 (2H, d, J=7.0 Hz), 2.49-2.62 (2H, m), 2.71-2.85 (2H, m), 2.90-3.04 (2H, m), 3.50 (3H, s), 3.81 (2H, t, J=4.9 Hz), 4.03-4.16 (1H, m), 4.17 (2H, t, J=4.9 Hz), 4.54-4.69 (2H, m), 6.60-6.68 (1H, m), 6.68-6.74 (1H, m), 6.88-6.93 (1H, m), 7.33-7.39 (2H, m), 7.39-7.44 (2H, m), 7.67-7.70 (1H, m).

Example 5

Compound (5-5): 6-{2-[4-(4-Bromo-3-hydroxybenzyl)piperidin-1-yl]ethyl}-3-hydroxy-2,3-dihydro-4H-chromen-4-one The compound was synthesized according to the following production method:
Production Method dimethoxy-3,4-dihydro-2H-chromen-6-yl)ethyl 4-methylbenzenesulfonate (RE8) (130 mg, 0.32 mmol) and potassium carbonate (88 mg, 0.64 mmol) in acetonitrile (3 mL) was heated under reflux for 2 hours. The reaction mixture was cooled to room temperature, and then, water (50 mL) was added, followed by extraction with chloroform. Combined organic layers were dried over anhydrous sodium sulfate, and then, the solvent was distilled off under reduced pressure. The obtained concentrated residue was purified by silica gel column chromatography (chloroform/methanol) to obtain the title compound (5-5-1) (139 mg, 79%) as a pale yellow oil.

Compound (5-5): 6-{2-[4-(4-Bromo-3-hydroxybenzyl)piperidin-1-yl]ethyl}-3-hydroxy-2,3-dihydro-4H-chromen-4-one A mixed solution of a 0.5 N aqueous hydrochloric acid solution (2 mL) and 1,4-dioxane (2 mL) containing the compound (5-5-1) (139 mg, 0.25 mmol) was stirred at room temperature for 4 hours. A 1 N aqueous hydrochloric acid solution (1 mL) was further added thereto, and the mixture was stirred at room temperature for 3 days. The reaction mixture was neutralized by the addition of a saturated aqueous solution of sodium bicarbonate and subjected to extraction with chloroform. Combined organic layers were dried over anhydrous sodium sulfate, and then, the solvent was distilled off under reduced pressure. The obtained concentrated residue was purified by silica gel column chromatog-

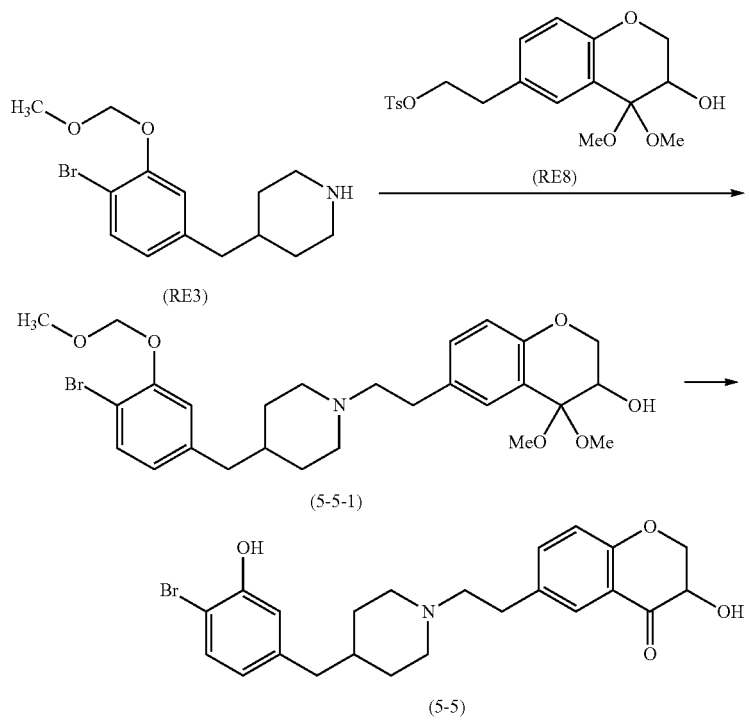

[Formula 46]

Compound (5-5-1): 6-(2-{4-[4-Bromo-3-(methoxymethoxy)benzyl]piperidin-1-yl}ethyl)-4,4-dimethoxy-3,4-dihydro-2H-chromen-3-ol A suspension of 4-[4-bromo-3-(methoxymethoxy)benzyl]piperidine (RE3) (100 mg, 0.32 mmol), 2-(3-hydroxy-4,4- raphy (chloroform/methanol) to obtain the compound (5-5) of interest (71 mg, 62%) as a light brown foamy solid.

$^1$H-NMR (400 MHz,CDCl$_3$) δ: 1.22-1.40 (2H, m), 1.45-1.58 (1H, m), 1.60-1.71 (1H, m), 1.89-2.02 (1H, m), 2.47 (2H, d, J=7.1 Hz), 2.48-2.63 (2H, m), 2.70-2.84 (2H, m), 2.89-3.06 (2H, m), 4.01-4.17 (1H, m), 4.54-4.68 (2H, m), 6.60 (1H, dd,

J=8.0, 2.0 Hz), 6.80 (1H, d, J=2.0 Hz), 6.91 (1H, d, J=8.3 Hz), 7.34 (1H, d, J=8.0 Hz), 7.36 (1H, dd, J=8.3, 2.4 Hz), 7.68 (1H, d, J=2.2 Hz).

Example 6

Compound (5-6): 6-(2-{4-[4-Bromo-3-(2-methoxyethoxy)benzyl]piperidin-1-yl}ethyl)-4H-chromen-4-one hydrochloride

[Formula 47]

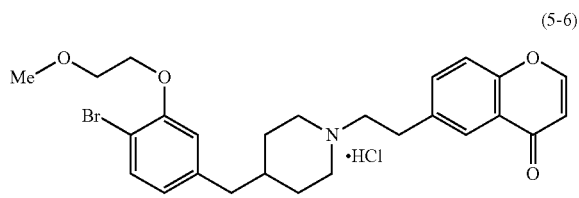

(5-6)

The compound (RE1) was converted to a free form in the same way as in Example 1, and a suspension of this 4-[4-bromo-3-(2-methoxyethoxy)benzyl]piperidine (2.50 g, 7.7 mmol), 2-(4-oxo-4H-chromen-6-yl)ethyl 4-methylbenzenesulfonate (RE7) (3.16 g, 9.2 mmol) and potassium carbonate (2.53 g, 18 mmol) in acetonitrile (50 mL) was heated under reflux for 2 hours. The reaction mixture was cooled to room temperature, then diluted with ethyl acetate, and washed with water and brine. The organic layer was dried over anhydrous sodium sulfate, and then, the solvent was distilled off under reduced pressure. The obtained concentrated residue was purified by silica gel column chromatography (chloroform/methanol) to obtain a free form of the title compound (2.76 g) as a yellow oil. This free form was dissolved in dichloromethane (30 mL). To this solution, a 1 N solution of hydrogen chloride in diethyl ether (10 mL, 10 mmol) was added at room temperature, and the solution was concentrated under reduced pressure. The obtained concentrated residue was suspended by the addition of diethyl ether (100 mL), and the resulting precipitate was collected by filtration, washed with diethyl ether, and then dried under reduced pressure to obtain the title compound (5-6) of interest (2.10 g, 51%) as a light brown powder.

$^1$H-NMR (300 MHz, DMSO-d6) δ: 1.42-1.66 (2H, m), 1.67-2.06 (3H, m), 2.66 and 2.53 (2H, d, J=7.5 Hz), 2.78-2.98 (2H, m), 3.15-3.34 (4H, m), 3.47-3.60 (2H, m), 3.69 (2H, br t, J=4.6 Hz), 4.18 (2H, br t, J=4.6 Hz), 6.36 and 6.38 (1H, d, J=5.9 Hz), 6.73 (1H, br d, J=7.7 Hz), 6.98 (1H, br s), 7.48 (1H, d, J=8.1 Hz), 7.61-7.79 (2H, m), 7.96 and 8.01 (1H, d, J=2.0 Hz), 8.31 and 8.33 (total 1H, d, J=5.9 Hz), 10.33 and 10.22 (total 1H br s).

Example 7

Compound (5-7): 6-(2-{4-[4-Bromo-3-(2-hydroxyethoxy)benzyl]piperidin-1-yl}ethyl)-4H-chromen-4-one hydrochloride

[Formula 48]

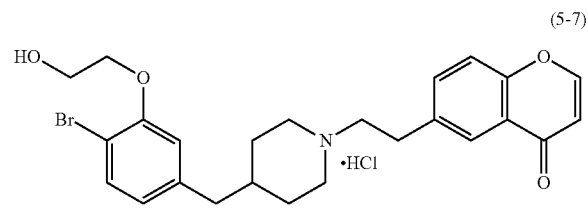

(5-7)

The compound was produced in the same way as in Example 6 using 2-[2-bromo-5-(piperidin-4-ylmethyl)phenoxy]ethanol (RE2) and 2-(4-oxo-4H-chromen-6-yl)ethyl 4-methylbenzenesulfonate (RE7).

Free base: $^1$H-NMR (300 MHz, CDCL3) δ: 1.20-1.43 (2H, m), 1.44-1.83 (3H, m), 1.89-2.09 (2H, m), 2.49 (2H, d, J=7.0 Hz), 2.56-2.70 (2H, m), 2.85-3.08 (4H, m), 3.50 (3H, s), 3.81 (2H, t, J=4.8 Hz), 4.17 (2H, t, J=4.9 Hz), 6.33 (1H, d, J=6.1 Hz), 6.64 (1H, dd, J=8.0, 1.7 Hz), 6.71 (1H, d, J=1.8 Hz), 7.39 (2H, d, J=8.6 Hz), 7.41 (2H, d, J=8.1 Hz), 7.53 (1H, dd, J=8.6, 2.2 Hz), 7.84 (1H, d, J=6.1 Hz), 8.01 (1H, d, J=2.2 Hz).

Example 8

Compound (5-8): 6-{2-[4-(4-Bromo-3-hydroxybenzyl)piperidin-1-yl]ethyl}-2,3-dihydro-4H-chromen-4-one

[Formula 49]

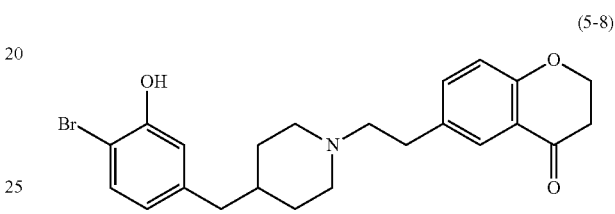

(5-8)

A suspension of 2-bromo-5-(piperidin-4-ylmethyl)phenol (RE4) (500 mg, 1.9 mmol), 2-(4-oxo-3,4-dihydro-2H-chromen-6-yl)ethyl 4-methylbenzenesulfonate (RE6) (612 mg, 1.8 mmol) and potassium carbonate (489 mg, 3.5 mmol) in acetonitrile (50 mL) and dimethylformamide (20 mL) was stirred at 55-60° C. for 6 hours. The reaction mixture was cooled to room temperature, and then, water was added thereto, followed by extraction with ethyl acetate. The organic layer was dried over anhydrous sodium sulfate. The solvent was distilled off under reduced pressure, and the obtained concentrated residue was purified by silica gel column chromatography (n-hexane:ethyl acetate=1:1→chloroform:methanol=20:1) to obtain a semi-purified product of the title compound. A small amount of ethyl acetate was added thereto, and the resulting precipitate was collected by filtration, washed with ethyl acetate, and then dried under reduced pressure to obtain the title compound (5-8) of interest (37 mg, 5%) as a white powder.

$^1$H-NMR (300 MHz, CDCL3) δ: 1.21-1.41 (2H, m), 1.48-1.67 (3H, m), 1.87-2.03 (2H, m), 2.47 (2H, d, J=6.8 Hz), 2.50-2.60 (2H, m), 2.69-2.85 (4H, m), 2.90-3.04 (2H, m), 4.51 (2H, t, J=6.4 Hz), 6.60 (1H, dd, J=8.2, 1.9 Hz), 6.81 (1H, d, J=1.8 Hz), 6.89 (1H, d, J=8.4 Hz), 7.32 (1H, dd, J=8.5, 2.1 Hz), 7.34 (1H, d, J=8.1 Hz), 7.70 (1H, d, J=2.4 Hz), 7.70 (1H, d, J=2.4 Hz).

Example 9

Compound (5-9): 6-{2-[4-(4-Bromo-3-hydroxybenzyl)piperidin-1-yl]ethyl}-4H-chromen-4-one The compound was synthesized according to the following production method:

Production Method

[Formula 50]

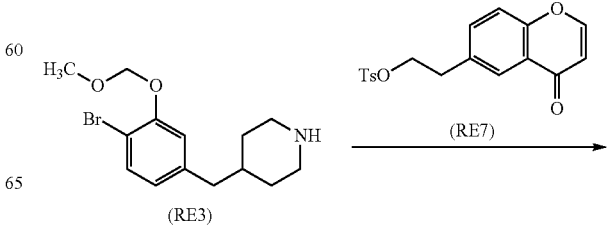

-continued

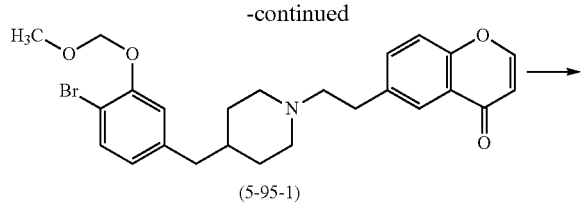

(5-95-1)

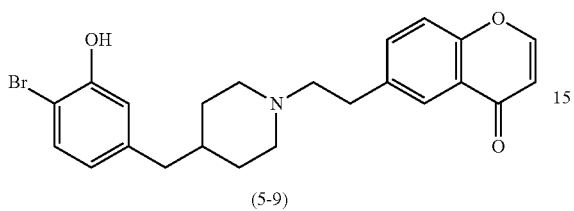

(5-9)

Compound (5-9-1): (6-(2-{4-[4-Bromo-3-(methoxymethoxy)benzyl]piperidin-1-yl}ethyl)-4H-chromen-4-one A solution of 4-[4-bromo-3-(methoxymethoxy)benzyl]piperidine (RE3) (96 mg, 0.31 mmol), 2-(4-oxo-4H-chromen-6-yl)ethyl 4-methylbenzenesulfonate (RE7) (100 mg, 0.29 mmol) and potassium carbonate (80 mg, 0.58 mmol) in acetonitrile (5 mL) was stirred overnight at 55-60° C. The reaction mixture was cooled to room temperature and then poured to water, followed by extraction with ethyl acetate. The organic layer was washed with brine and dried over anhydrous sodium sulfate, and then, the solvent was distilled off under reduced pressure. The obtained concentrated residue was purified by silica gel column chromatography (chloroform/methanol) to obtain the title compound (5-9-1) (46 mg, 33%) as a yellow oil.

Compound (5-9): 6-{2-[4-(4-Bromo-3-hydroxybenzyl)piperidin-1-yl]ethyl}-4H-chromen-4-one A solution of the compound (5-9-1) (46 mg, 0.095 mmol) in 10% hydrogen chloride and methanol (5 mL) was stirred at room temperature for 4.5 hours. The reaction mixture was neutralized by the addition of a 5% aqueous potassium carbonate solution and subjected to extraction with ethyl acetate. The organic layer was dried over anhydrous sodium sulfate, and then, the solvent was distilled off under reduced pressure. n-Hexane/ethyl acetate (3:1, 4 mL) was added to the obtained concentrated residue, and the resulting precipitate was collected by filtration and dried under reduced pressure to obtain the title compound (5-9) of interest (30 mg, 71%) as a white powder.

$^1$H-NMR (400 MHz, DMSO-d6) δ: 1.06-1.20 (2H, m), 1.34-1.47 (1H, m), 1.48-1.58 (2H, m), 1.81-1.93 (2H, m), 2.38 (2H, d, J=7.1 Hz), 2.82-2.91 (4H, m), 3.33 (2H, t, J=9.8 Hz), 6.33 (1H, d, J=6.1 Hz), 6.54 (1H, dd, J=8.3, 2.0 Hz), 6.73 (1H, d, J=1.7 Hz), 7.33 (1H, d, J=8.0 Hz), 7.56 (1H, d, J=8.8 Hz), 7.66 (1H, dd, J=8.5, 2.2 Hz), 7.85 (1H, d, J=2.2 Hz), 8.28 (1H, d, J=5.9 Hz).

Example 10

Compound (5-10): 6-(2-{4-[4-Bromo-3-(2-methoxyethoxy)benzyl]piperidin-1-yl}ethyl)-2-hydroxy-2,3-dihydro-4H-chromen-4-one

[Formula 51]

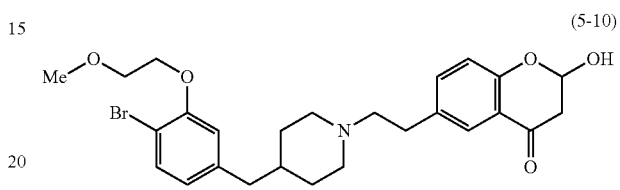

(5-10)

A 2 N aqueous sodium hydroxide solution (3 mL) was added to a solution of 6-(2-{4-[4-bromo-3-(2-methoxyethoxy)benzyl]piperidin-1-yl}ethyl)-4H-chromen-4-one hydrochloride (5-6) (60 mg, 0.12 mmol) in 1,4-dioxane (3 mL) at room temperature, and the reaction mixture was stirred at room temperature for 2 hours. Water was added thereto, and the mixture was adjusted to pH 3 with sodium bisulfate and then adjusted to pH 8 by the addition of sodium bicarbonate, followed by extraction with chloroform. The organic layer was dried over anhydrous sodium sulfate. The solvent was concentrated, and then, the obtained concentrated residue was purified by thin-layer silica gel chromatography (chloroform:methanol=10:1) to obtain the title compound (5-10) of interest (27 mg, 44%) as a light brown foamy solid.

$^1$H-NMER (300 MHz, CDCL3) δ: 1.22-1.43 (2H, m), 1.44-1.59 (1H, m), 1.60-1.74 (2H, m), 1.90-2.09 (2H, m), 2.49 (2H, d, J=7.0 Hz), 2.50-2.58 (2H, m), 2.64-3.09 (6H, m), 3.50 (3H, s), 3.81 (2H, t, J=4.9 Hz), 4.17 (2H, t, J=4.8 Hz), 5.85 (1H, br s), 6.63 (1H, dd, J=8.0, 1.7 Hz), 6.71 (1H, d, J=1.7 Hz), 6.81 (1H, d, J=8.4 Hz), 7.21 (1H, dd, J=8.4, 2.4 Hz), 7.42 (1H, d, J=7.9 Hz), 7.64 (1H, d, J=2.0 Hz).

Example 11

Compound (5-11): (6-(2-{4-[4-Bromo-3-(2-methoxyethoxy)benzyl]piperidin-1-yl}-1-hydroxyethyl)-2,3-dihydro-4H-chromen-4-one hydrochloride

[Formula 52]

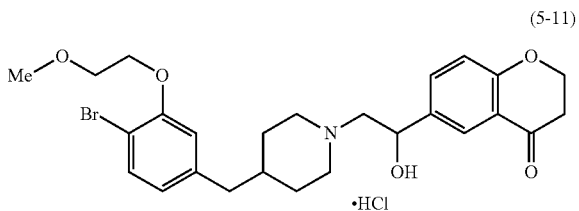

(5-11)

The compound (RE1) was converted to a free form in the same way as in Example 1, and a solution of this 4-[4-bromo-3-(2-methoxyethoxy)benzyl]piperidine (588 mg, 1.8 mmol)

and 6-(oxiran-2-yl)-2,3-dihydro-4H-chromen-4-one (RE9) (227 mg, 1.2 mmol) in toluene (2 mL) was stirred at 80° C. for 4.5 days. The solvent was distilled off under reduced pressure, and the obtained concentrated residue was purified by silica gel column chromatography (n-hexane:ethyl acetate=3:1→ethyl acetate). The obtained fraction was further purified by thin-layer silica gel chromatography (hexane:2-propanol:triethylamine=10:1:0.5) to obtain the title compound (175 mg, 23%) as a pale yellow oil. This compound was dissolved in chloroform (1 mL). To this solution, a 1 N solution of hydrogen chloride in 1,4-dioxane (1 mL) was added at room temperature. The solvent was distilled off under reduced pressure, and then, the obtained concentrated residue was crystallized by the addition of diethyl ether (4 mL) and acetone (0.2 mL). The solvent was distilled off under reduced pressure to obtain the title compound (5-11) of interest (202 mg) as a pale yellow solid.

$^1$H-NMR (300 MHz, DMSO-$d_6$) δ: 9.56 (1H, s), 7.81 (d, J=2.0 Hz, 1H, Ar), 7.59 (dd, J=2.0, 8.5 Hz, 1H, Ar), 7.48 (d, J=8.7 Hz, 1H, Ar), 7.07 (d, J=8.5 Hz, 1H, Ar), 6.97 (brs, 1H, Ar), 6.73 (brd, J=8.7 Hz, 1H, Ar), 6.26 (d, J=3.5 Hz, 1H, OH), 5.11 (brs, 1H, CH), 4.53 (t, J=6.2 Hz, 2H, CH$_2$), 4.17 (t, J=4.3 Hz, 2H, CH$_2$), 3.69 (t, J=4.3 Hz, 2H, CH$_2$), 3.66-3.48 (m, 2H), 3.35 (s, 3H, CH$_3$), 3.18-3.09 (m, 2H), 3.01-2.85 (m, 2H), 2.80 (t, J=6.2 Hz, 2H, CH$_2$), 2.53 (brs, 2H, CH$_2$), 1.85-1.42 (m, 5H).

Reference Example 10

Compound (4-10): [2-Bromo-5-({1-[2-(3-hydroxy-4-oxo-3,4-dihydro-2H-chromen-6-yl)ethyl]piperidin-4-yl}methyl)phenoxy]acetic acid hydrochloride The compound was synthesized according to the following production method:
Production Method

[Formula 53]

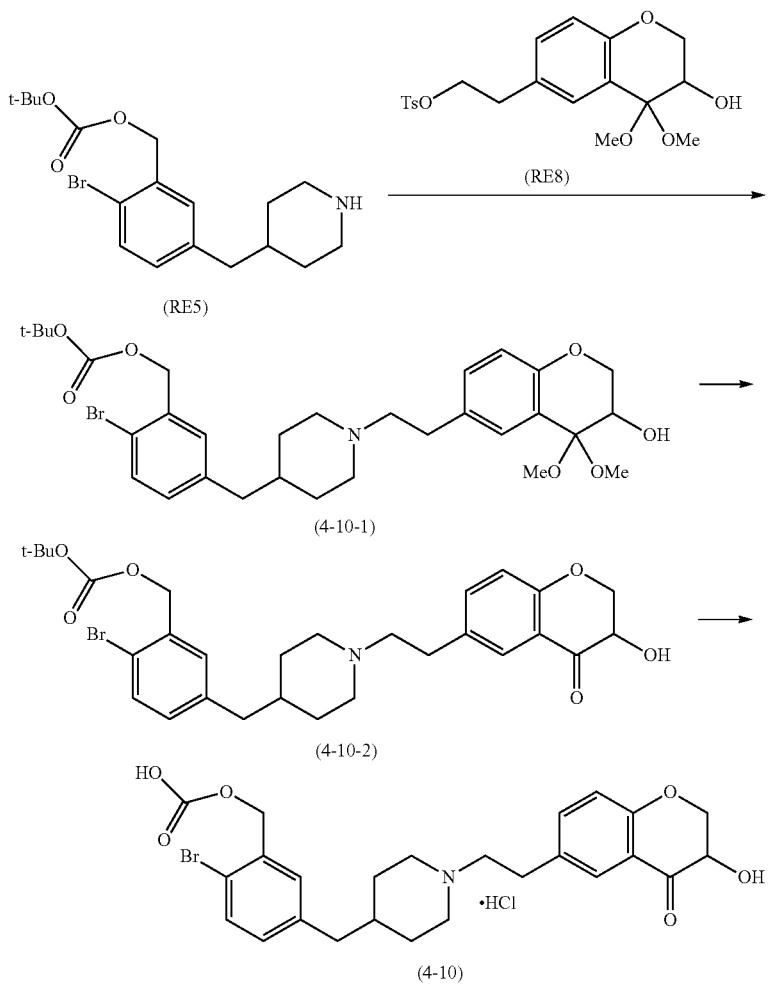

Compound (4-10-1): tert-Butyl [2-bromo-5-({1-[2-(3-hydroxy-4,4-dimethoxy-3,4-dihydro-2H-chromen-6-yl)ethyl]piperidin-4-yl}methyl)phenoxy]acetate A suspension of tert-butyl [2-bromo-5-(piperidin-4-ylmethyl)phenoxy]acetate (RE5) (470 mg, 1.2 mmol), 2-(3-hydroxy-4,4-dimethoxy-3,4-dihydro-2H-chromen-6-yl)ethyl 4-methylbenzenesulfonate (RE8) (500 mg, 1.2 mmol) and potassium carbonate (345 mg, 2.5 mmol) in acetonitrile (5 mL) was heated under reflux for 2 hours. The reaction mixture was cooled to room temperature, and then, water (20 mL) was added thereto, followed by extraction with chloroform. The organic layer was dried over anhydrous sodium sulfate. The solvent was distilled off under reduced pressure, and then, the obtained concentrated residue was purified by silica gel column chromatography (chloroform/methanol) to obtain the title compound (4-10-1) (639 mg, 84%) as a colorless foamy solid.

Compound (4-10-2): tert-Butyl [2-bromo-5-({1-[2-(3-hydroxy-4-oxo-3,4-dihydro-2H-chromen-6-yl)ethyl]piperidin-4-yl}methyl)phenoxy]acetate p-Toluenesulfonic acid monohydrate (190 mg, 1.0 mmol) was added to a mixed solution of 1,4-dioxane (20 mL) and water (20 mL) containing the compound (4-10-1) (585 mg, 1.0 mmol) at room temperature, and the reaction mixture was stirred at room temperature for 4 hours. The reaction mixture was neutralized by the addition of a saturated aqueous solution of sodium bicarbonate and subjected to extraction with chloroform. The organic layer was dried over anhydrous sodium sulfate, and then, the solvent was distilled off under reduced pressure. The obtained concentrated residue was purified by silica gel column chromatography (chloroform/methanol) to obtain the title compound (4-10-2) (485 mg, 77%) as a pale yellow oil.

Compound (4-10): [2-Bromo-5-({1-[2-(3-hydroxy-4-oxo-3,4-dihydro-2H-chromen-6-yl)ethyl]piperidin-4-yl}methyl)phenoxy]acetic acid hydrochloride A solution of the compound (4-10-2) (100 mg, 0.174 mmol) in 4 N hydrogen chloride and 1,4-dioxane (2 mL) was stirred at room temperature for 2.5 hours. The solvent was distilled off under reduced pressure, and the obtained concentrated residue was suspended by the addition of t-butylmethyl ether (10 mL). The resulting precipitate was collected by filtration, washed with t-butylmethyl ether (2 mL), and then dried under reduced pressure to obtain the title compound (4-10) of interest (88 mg, 91%) as a light brown powder.

$^1$H-NMR (400 MHz, DMSO-d6) δ: 1.36-1.62 (2H, m), 1.63-1.85 (3H, m), 2.37-2.67 (2H, m), 2.72-3.86 (7H, m), 4.10-4.29 (1H, m), 4.33-4.56 (2H, m), 4.80 (2H, s), 5.90-6.12 (1H, m), 6.67-6.92 (2H, m), 6.96-7.09 (1H, m), 7.40-7.56 (2H, m), 7.60-7.76 (1H, m), 10.05 (1H, br s), 13.12 (1H, br s).

Reference Example 11

Compound (4-11): [2-Bromo-5-({1-[2-(4-oxo-4H-chromen-6-yl)ethyl]piperidin-4-yl}methyl)phenoxy]acetic acid hydrochloride The compound was synthesized according to the following production method:
Production Method

[Formula 54]

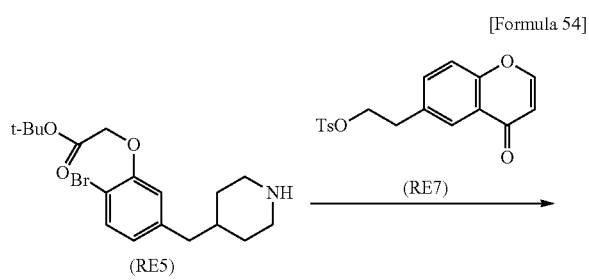

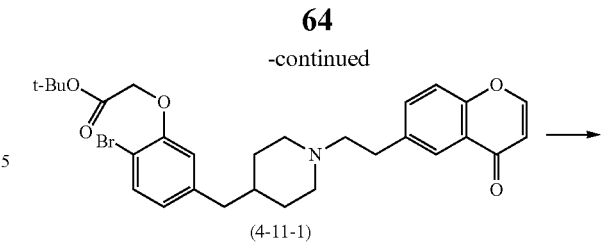

Compound (4-11-1): tert-Butyl [2-bromo-5-({1-[2-(4-oxo-4H-chromen-6-yl)ethyl]piperidin-4-yl}methyl)phenoxy]acetate A suspension of tert-butyl [2-bromo-5-(piperidin-4-ylmethyl)phenoxy]acetate (RE5) (800 mg, 2.5 mmol), 2-(4-oxo-4H-chromen-6-yl)ethyl 4-methylbenzenesulfonate (RE7) (844 mg, 2.5 mmol) and potassium carbonate (676 mg, 4.9 mmol) in acetonitrile (15 mL) was heated under reflux for 2 hours. The reaction mixture was cooled to room temperature, and then, water (30 mL) was added thereto, followed by extraction with chloroform. The organic layer was dried over anhydrous sodium sulfate. The solvent was distilled off under reduced pressure, and then, the obtained concentrated residue was purified by silica gel column chromatography (chloroform/methanol) to obtain the title compound (4-11-1) (643 mg, 47%) as a colorless foamy solid.

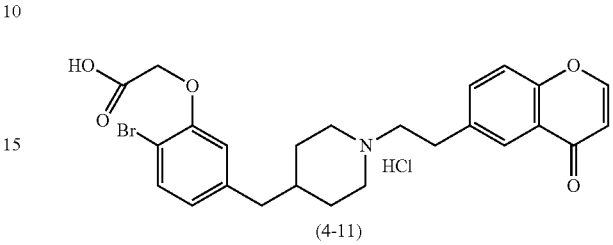

Compound (4-11): [2-Bromo-5-({1-[2-(4-oxo-4H-chromen-6-yl)ethyl]piperidin-4-yl}methyl)phenoxy]acetic acid hydrochloride A solution of the compound (4-11-1) (640 mg, 1.2 mmol) in 4 N solution of hydrogen chloride in 1,4-dioxane (10 mL) was stirred at room temperature for 4 hours. The solvent was distilled off under reduced pressure, and the obtained concentrated residue was suspended by the addition of diethyl ether. The solvent was removed by decantation, and the obtained precipitate was dried under reduced pressure to obtain the title compound (4-11) of interest (571 mg, 92%) as a light brown powder.

$^1$H-NMR (400 MHz, DMSO-d6) δ: 1.41-1.64 (2H, m), 1.66-1.86 (3H, m), 2.43-2.59 (2H, m), 2.77-2.97 (2H, m), 3.17-3.34 (4H, m), 3.46-3.61 (2H, m), 4.80 (2H, s), 6.36 (1H, d, J=6.1 Hz), 6.75 (1H, dd, J=8.1, 1.5 Hz), 6.85 (1H, s), 7.49 (1H, d, J=7.9 Hz), 7.65 (2H, d, J=8.6 Hz), 7.72 (1H, dd, J=9.1, 1.7 Hz), 7.96 (1H, s), 8.31 (1H, d, J=5.9 Hz).

Example 12

Compound (5-12): (+)-6-(2-{4-[4-Bromo-3-(2-methoxyethoxy)benzyl]piperidin-1-yl}ethyl)-3,4-dihydro-2H-chromen-4-ol benzenesulfonate (salt)

The compound was synthesized according to the following production method:
Production Method

[Formula 55]

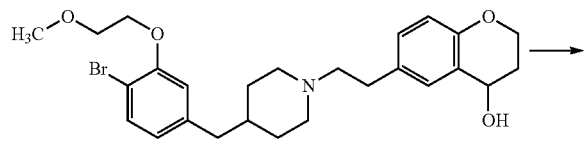
(5-1-1)

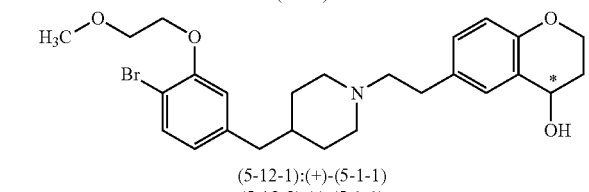
(5-12-1):(+)-(5-1-1)
(5-12-2):(−)-(5-1-1)

(5-12-1) ⟶

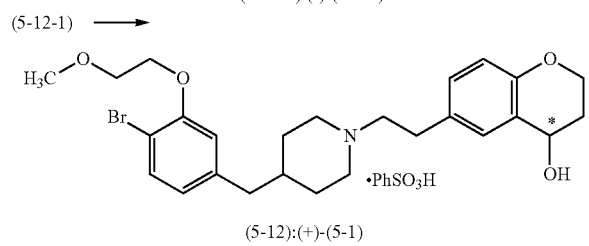
(5-12):(+)-(5-1)

wherein a compound whose asymmetric carbon is represented by * represents an optically active form.

Compound (5-12-1): (+)-6-(2-{4-[4-Bromo-3-(2-methoxyethoxy)benzyl]piperidin-1-yl}ethyl)-3,4-dihydro-2H-chromen-4-ol and compound (5-12-2): (−)-6-(2-{4-[4-bromo-3-(2-methoxyethoxy)benzyl]piperidin-1-yl}ethyl)-3,4-dihydro-2H-chromen-4-ol The compound (5-1-1) was resolved using liquid column chromatography (for the conditions, see below) to obtain both of a low-affinity optical isomer (5-12-1) eluted at a shorter retention time and a high-affinity optical isomer (5-12-2) then eluted, as light brown oils.
The liquid column chromatography conditions are shown below.
Column: CHIRALPAK (R) IA
5 cm I.D.×25 cm
Mobile phase: methanol:diethylamine=100:0.1 (v/v)
Flow rate: 35 mL/min.
Temperature: 40° C.
UV wavelength for observation: 279 nm
Both the compound (5-12-1) and the compound (5-12-2) were confirmed to have optical purity of 99% or more, under HPLC analysis conditions shown below.
Column: CHIRALPAK (R) AD-H
4.6 mm I.D.×25 cm
Mobile phase: 0.1% (v/v) diethylamine-2-propanol:0.1% (v/v) diethylamine-n-hexane=50:50
Flow rate: 1 mL/min.
Temperature: 25° C.
UV wavelength for observation: 230 nm
Compound (5-12-1): Retention time: 8.57 min.
$^1$H-NMR (300 MHz, CDCl$_3$) δ: 1.23-1.40 (2H, m), 1.42-1.56 (1H, m), 1.57-1.67 (2H, m), 1.87-2.17 (4H, m), 2.46-2.55 (2H, m), 2.48 (2H, d, J=7.2 Hz), 2.68-2.76 (2H, m), 2.86-3.01 (2H, m), 3.49 (3H, s), 3.81 (2H, t, J=4.8 Hz), 4.17 (2H, t, J=4.8 Hz), 4.22-4.27 (2H, m), 4.76 (1H, br t, J=3.3 Hz), 6.63 (1H, dd, J=8.1, 1.7 Hz), 6.71 (1H, d, J=1.8 Hz), 6.75 (1H, d, J=8.3 Hz), 7.02 (1H, dd, J=8.3, 2.0 Hz), 7.13 (1H, d, J=2.0 Hz), 7.41 (1H, d, J=8.1 Hz).
Specific rotation: $[\alpha]_D^{26}$+8.8 (c.1.00, CHCl$_3$)
Compound (5-12-2): Retention time: 13.14 min.
Specific rotation: $[\alpha]_D^{26}$−9.1 (c.1.06, CHCl$_3$)

Compound (5-12): (+)-6-(2-{4-[4-Bromo-3-(2-methoxyethoxy)benzyl]piperidin-1-yl}ethyl)-3,4-dihydro-2H-chromen-4-ol benzenesulfonate (salt)

A solution of benzenesulfonic acid monohydrate (881 mg, 5.0 mmol) in acetone (10 mL) was added dropwise to a solution of the compound (5-12-1) (2.50 g, 5.0 mmol) in acetone (50 mL) at room temperature in 5 minutes, and the mixed solution was stirred at room temperature for 1 hour. The solvent was distilled off under reduced pressure, and a small amount of diethyl ether was added to the obtained concentrated residue, followed by decantation to obtain a crude product of the title compound (5-12). This crude product was stirred in acetone (30 mL) at room temperature for 30 minutes, and then, the solid matter was collected by filtration, washed with acetone (3 mL×2), and dried under reduced pressure to obtain the title compound (5-12) (3.11 g, 95%) as a white powder.
Specific rotation: $[\alpha]_D^{25}$+12.6 (c.1.02, CHCl$_3$)

Example 13

Compound (5-13): (−)-6-(2-{4-[4-Bromo-3-(2-methoxyethoxy)benzyl]piperidin-1-yl}ethyl)-3,4-dihydro-2H-chromen-4-ol benzenesulfonate (salt)

[Formula 56]

(5-13): (−)-(5-1)

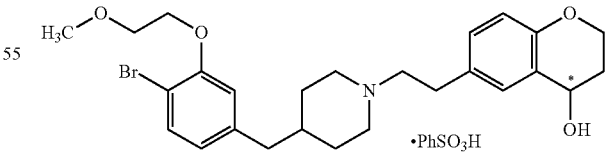

wherein * is as defined above.
The title compound (5-13) was obtained as a white powder in the same way as in Example 12 using the compound (5-12-2) obtained in Example 12.
Specific rotation: $[\alpha]_D^{25}$−12.2 (c.1.03, CHCl$_3$)

Example 14

Compound (5-14): 6-(2-{4-[4-Bromo-3-(2-methoxy-ethoxy)benzyl]piperidin-1-yl}ethyl)-3-hydroxy-4H-chromen-4-one

[Formula 57]

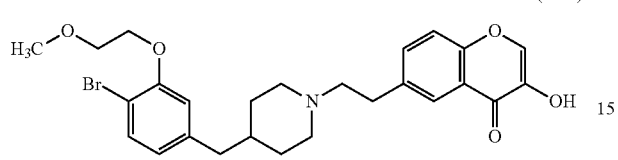

(5-14)

The compound (5-3) (100 mg) was added to a saturated aqueous solution of sodium bicarbonate, and the mixed solution was subjected to extraction with chloroform. The organic layer was dried over anhydrous sodium sulfate, and then, the solvent was distilled off under reduced pressure to obtain a free base of the compound (5-3) (102 mg) as a pale yellow oil. A sulfur trioxide/pyridine complex (23 mg, 0.15 mmol) was added to a solution of the free base of the compound (5-3) (19 mg, 0.037 mmol) and triethylamine (41 µL, 0.30 mmol) in dimethyl sulfoxide (1 mL) at room temperature, and the reaction mixture was stirred at room temperature for 1 hour. Water was added to the solution, followed by extraction with chloroform. The organic layer was dried over anhydrous sodium sulfate, and then, the solvent was distilled off under reduced pressure. The obtained concentrated residue was purified by silica gel column chromatography (chloroform:methanol=96:4→90:10) to obtain the title compound (5-14) (11 mg, 59%) as a yellow foamy solid.

$^1$H-NMR (300 MHz, CDCl$_3$) δ: 1.23-1.41 (2H, m), 1.33-1.50 (1H, m), 1.50-1.62 (2H, m), 1.92-2.05 (2H, m), 2.49 (2H, d, J=7.0 Hz), 2.60-2.67 (2H, m), 2.87-3.05 (4H, m), 3.50 (3H, s), 3.81 (2H, t like, J=4.9 Hz), 4.17 (2H, t like, J=4.9 Hz), 6.64 (1H, dd, J=8.4, 1.8 Hz), 6.71 (1H, d, J=1.8 Hz), 7.33-7.45 (2H, m), 7.52 (1H, dd, J=8.8, 2.2 Hz), 7.97 (1H, s), 8.05 (1H, d, J=2.0 Hz).

Example 15

Compound (5-15): 6-{2-[4-(4-Bromo-3-hydroxybenzyl)piperidin-1-yl]ethyl}-3,4-dihydro-2H-chromen-4-ol

[Formula 58]

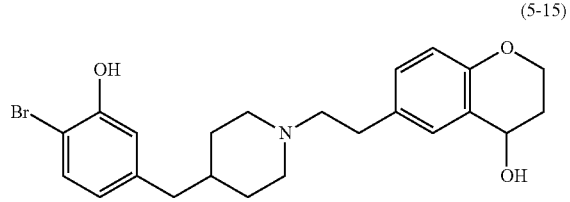

(5-15)

Sodium borohydride (13 mg, 0.34 mmol) was added to a solution of the compound (5-8) (50 mg, 0.11 mmol) in methanol (1 mL) with ice cooling, and the reaction mixture was stirred for 30 minutes under ice cooling and then stirred at room temperature for 45 minutes. Subsequently, methanol (3 mL) was added thereto. To the mixture, sodium borohydride (13 mg, 0.34 mmol) was added thereto with ice cooling, and the reaction mixture was further stirred for 30 minutes. Water (1 mL) was added thereto, and methanol was distilled off under reduced pressure. Water (2 mL) was added to the concentrated residue, followed by extraction with chloroform. The organic layer was dried over anhydrous sodium sulfate, and then, the solvent was distilled off under reduced pressure to obtain the title compound (5-15) (60 mg, quantitative) as a white solid.

$^1$H-NMR (300 MHz, CDCl$_3$) δ: 1.23-1.71 (5H, m), 1.88-2.19 (4H, m), 2.46-2.55 (4H, m), 2.73 (2H, m), 2.98 (2H, d, J=11.6 Hz), 4.23 (2H, m), 4.76 (1H, t, J=3.9 Hz), 6.60 (1H, d, J=8.3 Hz), 6.76 (1H, d, J=8.4 Hz), 6.80 (1H, s), 7.03 (1H, d, J=8.4 Hz), 7.14 (1H, s), 7.34 (1H, d, J=8.1 Hz).

Reference Example 12

Compound (4-12): [2-Bromo-5-(piperidin-4-ylmethyl)phenoxy]acetic acid hydrochloride

[Formula 59]

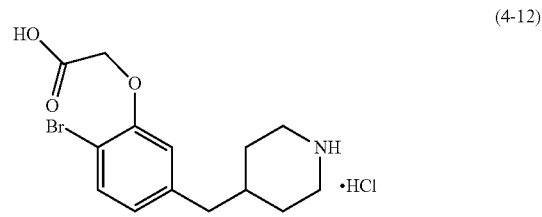

(4-12)

The compound (4-5-2) (215 mg, 0.44 mmol) was added to a 4 N solution of hydrogen chloride in 1,4-dioxane (5 mL) at room temperature, and the reaction mixture was stirred at 40° C. for 4 hours and then stirred overnight at room temperature. The solvent was distilled off under reduced pressure, and a small amount of acetone was added to the obtained concentrated residue. The resulting solid was collected by filtration and dried under reduced pressure to obtain the title compound (4-12) (152 mg, 94%) as a white powder.

$^1$H-NMR (400 MHz, DMSO-d6) δ: 1.25-1.40 (2H, m), 1.65-1.83 (3H, m), 2.49 (2H, d, J=5.9 Hz), 2.73-2.83 (2H, m), 3.16-3.25 (2H, m), 4.79 (2H, s), 6.73 (1H, dd, J=8.1, 1.7 Hz), 6.83 (1H, d, J=1.7 Hz), 7.48 (1H, d, J=8.1 Hz), 8.61 and 8.84 (total 2H, br s), 13.13 (1H, br s).

Reference Example 13

Compound (4-13): Sodium [2-bromo-5-({1-[2-(4-hydroxy-3,4-dihydro-2H-chromen-6-yl)ethyl]piperidin-4-yl}methyl)phenoxy]acetate The compound was synthesized according to the following production method:
Production Method

[Formula 60]

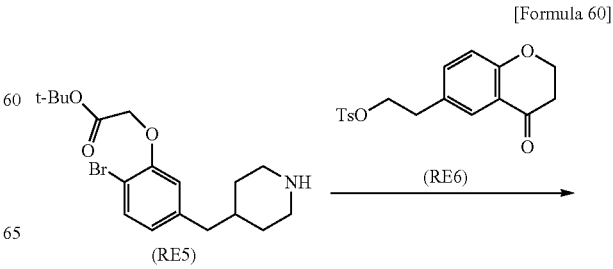

-continued

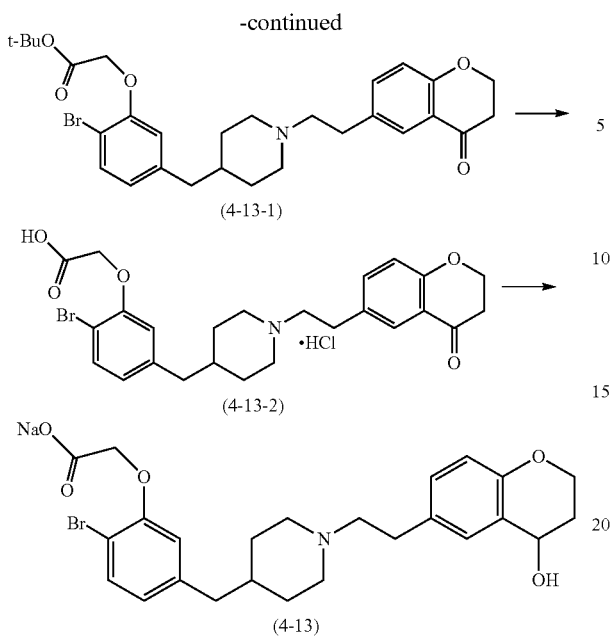

Compound (4-13-1): tert-Butyl [2-bromo-5-({1-[2-(4-oxo-3,4-dihydro-2H-chromen-6-yl)ethyl]piperidin-4-yl}methyl)phenoxy]acetate A solution of the compound (RE5) (2.30 g, 6.0 mmol), the compound (RE6) (1.97 g, 5.7 mmol) and potassium carbonate (1.57 g, 11 mmol) in acetonitrile (25 mL) was stirred at 55-60° C. for 19.5 hours. After cooling to room temperature, water (100 mL) was added thereto, followed by extraction with chloroform. The chloroform layer was dried over anhydrous sodium sulfate. The solvent was distilled off under reduced pressure, and then, the obtained concentrated residue was purified by silica gel column chromatography (n-hexane:ethyl acetate=1:1→chloroform:methanol=20:1) to obtain the compound (4-13-1) (3.51 g, quantitative).

Compound (4-13-2): [2-Bromo-5-({1-[2-(4-oxo-3,4-dihydro-2H-chromen-6-yl)ethyl]piperidin-4-yl}methyl)phenoxy]acetic acid hydrochloride A 4 N solution of hydrogen chloride in 1,4-dioxane (35 mL) was added to the compound (4-13-1) (3.50 g, 6.8 mmol), and the reaction mixture was stirred at 50° C. for 1.5 hours. The reaction solution was cooled to room temperature, and then, the solvent was distilled off under reduced pressure. Acetone (35 mL) was added to the obtained concentrated residue, and the resulting precipitate was collected by filtration and washed with acetone (5 mL×2) to obtain a crude product of the compound (4-13-2) (2.34 g). This crude product was added to acetone (50 mL), and the mixed solution was heated under reflux for 1 hour, then gradually cooled to room temperature in 1.5 hours, and stirred at 20° C. for 1 hour. Then, the precipitate was collected by filtration and washed with acetone (5 mL×2) to obtain the compound (4-13-2) (2.20 g, 60%) as a white powder.

Compound (4-13): Sodium [2-bromo-5-({1-[2-(4-hydroxy-3,4-dihydro-2H-chromen-6-yl)ethyl]piperidin-4-yl}methyl)phenoxy]acetate Sodium borohydride (10 mg, 0.26 mmol) was added to a solution of the compound (4-13-2) (20 mg, 0.037 mmol) in methanol (2 mL) at room temperature, and the reaction mixture was stirred at room temperature for 3.5 hours. Then, water (0.5 mL) was added thereto, and the mixture was stirred at room temperature for 3 days. Methanol was distilled off under reduced pressure, and ethanol (10 mL×2) was added to the obtained concentrated residue, followed by concentration. To the obtained solid matter, ethanol (3 mL) was added at room temperature, and the salt was collected by filtration. The filtrate was concentrated to obtain the title compound (4-13) (18 mg, 92%) as a white solid.

$^1$H-NMR (300 MHz, DMSO-d6) δ: 1.05-1.25 (2H, m), 1.30-1.45 (1H, m), 1.45-1.58 (2H, m), 1.75-2.00 (4H, m), 2.33-2.45 (4H, m), 2.53-2.65 (2H, m), 2.80-2.92 (2H, m), 4.09-4.14 (2H, m), 4.12 (2H, s), 4.50-4.60 (1H, m), 5.33 (1H, br s), 6.53-6.59 (2H, m), 6.60 (1H, d, J=8.3 Hz), 6.94 (1H, dd, J=8.3, 2.2 Hz), 7.10 (1H, d, J=2.0 Hz), 7.34 (1H, d, J=7.9 Hz).

Reference Example 14

Compound (RE10): 2-(3-Hydroxy-4-oxo-3,4-dihydro-2H-chromen-6-yl)ethyl 4-methylbenzenesulfonate

[Formula 61]

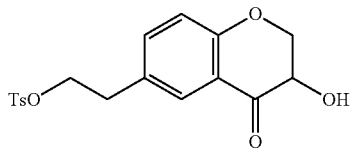

1 N hydrochloric acid (0.5 mL) was added to a solution of the compound (RE8) (400 mg, 1.0 mmol) in tetrahydrofuran (4 mL) at room temperature, and the reaction mixture was stirred at room temperature for 30 minutes. The reaction mixture was separated into aqueous and organic layers by the addition of water and ethyl acetate, and the organic layer was washed with brine and then dried over anhydrous magnesium sulfate. The solvent was distilled off under reduced pressure, and then, n-hexane (2 mL) and ethyl acetate (2 mL) were added to the obtained concentrated residue. The resulting precipitate was collected by filtration and dried under reduced pressure to obtain the title compound (RE10) (314 mg, 86%) as a white powder.

$^1$H-NMR (300 MHz, CDCl$_3$) δ: 2.44 (3H, s), 2.93 (2H, t, J=6.8 Hz), 3.53 (1H, d, J=2.0 Hz), 4.10 (1H, dd, J=12.5, 9.9 Hz), 4.19 (2H, t, J=6.8 Hz), 4.59 (1H, ddd, J=12.7, 6.4, 2.0 Hz), 4.63 (1H, dd, J=9.9, 6.4 Hz), 6.90 (1H, d, J=8.6 Hz), 7.27-7.33 (3H, m), 7.58 (1H, d, J=2.2 Hz), 7.71 (2H, d, J=7.8 Hz).

Reference Example 15

Compound (RE11): 2-(3-Hydroxy-4-oxo-4H-chromen-6-yl)ethyl 4-methylbenzenesulfonate

[Formula 62]

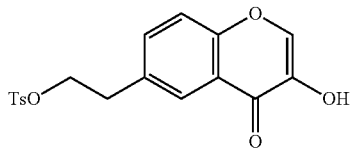

A sulfur trioxide/pyridine complex (527 mg, 3.3 mmol) was added to a solution of the compound (RE10) (300 mg, 0.83 mmol) and triethylamine (922 µL, 6.6 mmol) in dimethyl sulfoxide (6 mL) at room temperature, and the reaction mixture was stirred at room temperature for 2 hours. A 5% aqueous potassium bisulfate solution (30 mL) was added thereto, followed by extraction with ethyl acetate. Combined organic layers were washed with water and brine in this order and then dried over anhydrous sodium sulfate. The solvent was distilled off under reduced pressure, and n-hexane (2 mL) and ethyl acetate (2 mL) were added to the obtained concentrated residue. The resulting precipitate was collected by filtration, and the residue was washed with a mixed solution of n-hexane (0.5 mL) and ethyl acetate (0.5 mL) and then dried under reduced pressure to obtain the title compound (RE11) (145 mg, 48%) as a light brown powder.

$^1$H-NMR (300 MHz, CDCl$_3$) δ: 2.40 (3H, s), 3.06 (2H, t, J=6.6 Hz), 4.27 (2H, t, J=6.6 Hz), 6.13 (1H, s), 7.24 (2H, d, J=7.9 Hz), 7.40 (1H, d, J=8.6 Hz), 7.46 (1H, dd, J=8.8, 2.2 Hz), 7.65 (2H, d, J=7.9 Hz), 7.92 (1H, d, J=2.2 Hz), 8.00 (1H, s).

Test Example 1

Screening Test Using [$^3$H] Citalopram Binding for Evaluating Inhibitory Effect on Human Serotonin Reuptake 1-1 Cells Used and Preparation of Membrane Preparation CHO cells expressing a human serotonin transporter (h-SERT) (h-SERT/CHO) were used in the experiment. The cells were cultured in F12 containing 10% FCS, 500 µg/ml Geneticin and 100 U/ml penicillin-100 µg/ml streptomycin (all manufactured by Sigma-Aldrich Corp.) in a 5% CO$_2$ incubator. The cells dissociated and collected therefrom using SERT buffer (50 mM Tris-HCl containing 120 mM NaCl and 5 mM KCl (pH=7.4)) were homogenized using a Teflon (R) homogenizer and then centrifuged (50,000×g, 30 min, 4° C.). The precipitate was resuspended in an appropriate amount of SERT buffer and stored at −80° C. until use. The amount of the protein in the membrane preparation were determined using bovine serum albumin (manufactured by Sigma-Aldrich Corp.) as standards and Dye Reagent Concentrate (manufactured by Bio-Rad Laboratories, Inc.).

1-2 Receptor Binding Experiment

[$^3$H] citalopram binding was assayed according to the method of Owens et al. [Owens M. J. et al., J. Pharm. Exp. Ther., 283, 1305-1322 (1997)]. Specifically, 50 µl of [$^3$H] citalopram (final concentration: approximately 2 nM) diluted with SERT buffer, 149 µl of the h-SERT/CHO membrane preparation (40 µg/well in terms of the amount of the protein), and 1 µl of a solution of a test drug dissolved in DMSO were added to prepare 200 µl in total of a solution. This solution was reacted at room temperature for 60 minutes and then immediately suction-filtered at a low pressure using a glass fiber filter paper coated with a 0.05% aqueous polyethyleneimine solution. The glass fiber filter paper was washed twice with 250 µl of SERT buffer and then transferred to a glass vial containing 4 ml of ACS-II (manufactured by GE Healthcare (formerly Amersham Biosciences)). Radioactivity remaining on the filter paper was measured using a liquid scintillation counter. The nonspecific binding of [$^3$H] citalopram was defined as a binding amount in the presence of 1 µM clomipramine.

IC$_{50}$ values were calculated by Hill analysis [see Hill A. V., J. Physiol., 40, 190-200 (1910)], and h-SERT binding inhibition constants (Ki) were calculated according to the formula:

$$h\text{-}SERT \text{ binding inhibition constant } (Ki) = IC_{50}/(1+S/Kd)$$

[S represents the concentration of added [$^3$H] citalopram. Moreover, the Kd value was the binding dissociation constant of [$^3$H] citalopram, and a value (2.16 nM) calculated by a saturation binding experiment separately carried out using the same cell membrane was used.] The smaller numeric value of the h-SERT binding inhibition constant Ki means a higher inhibitory effect on human serotonin reuptake.

Test Example 2

[$^3$H] 8-OH-DPAT Binding Test for Evaluating Affinity for Human Serotonin 1A Receptor 2-1 Cells Used and Preparation of Membrane Preparation CHO cells expressing a human serotonin 1A receptor (h-5-HT$_{1A}$) (h-5-HT$_{1A}$/CHO) were used in the experiment. The cells were cultured in F12 containing 10% FCS, 500 µg/ml Geneticin and 100 U/ml penicillin-100 µg/ml streptomycin (all manufactured by Sigma-Aldrich Corp.) in a 5% CO$_2$ incubator. Membrane preparation were prepared according to the method of Yabuuchi et al.[3]. Specifically, the cells dissociated and collected therefrom using 50 mM Tris-HCl (pH=7.4) were homogenized using a Teflon® homogenizer and then centrifuged (48,000×g, 20 min, 4° C.). The precipitate was resuspended in an appropriate amount of 50 mM Tris-HCl (pH=7.4) and stored at −80° C. until use. The amount of the protein in the membrane preparation were determined using bovine serum albumin (manufactured by Sigma-Aldrich Corp.) as standards and Dye Reagent Concentrate (manufactured by Bio-Rad Laboratories, Inc.).

2-2 Receptor Binding Experiment

The experiment was carried out according to the method of Yabuuchi et al. [Yabuuchi K. et al., Biogenic Amines, 18, 319-328 (2004)]. 50 µl of [$^3$H] 8-OH-DPAT (final concentration: 0.5 nM), 1 µl of a test drug solution, and 149 µl of the h-5-HT$_{1A}$/CHO membrane preparation (25 µg/well in terms of the amount of the protein) were added into a buffer containing 50 mM Tris-HCl (pH=7.4) and 4 mM CaCl$_2$, and 200 µl in total of the reaction solution was used in the assay. The reaction solution was reacted at room temperature for 30 minutes and then immediately suction-filtered at a low pressure using a glass fiber filter paper. The glass fiber filter paper was washed twice with 250 µl of 50 mM Tris-HCl (pH=7.4) and then added to a counting vial containing 4 ml of ACS-II (manufactured by GE Healthcare (formerly Amersham Biosciences)). Receptor binding-derived radioactivity remaining on the filter paper was measured using a liquid scintillation counter. The nonspecific binding was defined as a binding amount in the presence of 10 µM 8-OH-DPAT.

IC$_{50}$ values were calculated by Hill analysis [see Hill A. V., J. Physiol., 40, 190-200 (1910)], and h-5-HT$_{1A}$ binding inhibition constants (Ki) were calculated according to the formula:

$$h\text{-}5\text{-}HT_{1A} \text{ binding inhibition constant } (Ki) = IC_{50}/(1+S/Kd)$$

[S represents the concentration of added [$^3$H] 8-OH-DPAT. Moreover, the Kd value was the binding dissociation constant of [$^3$H] 8-OH-DPAT, and a value (1.28 nM) calculated by a saturation binding experiment separately carried out using the same cell membrane was used.] The smaller numeric value of the h-5-HT$_{1A}$ binding inhibition constant Ki means higher affinity for human serotonin 1A receptors.

The compounds of the present invention, the reference compounds and the intermediate compounds obtained in Examples and Reference Examples were subjected to the tests of Test Examples 1 and 2, and the results are shown in Table 1. These test results demonstrated that the compound of the present invention or the pharmaceutically acceptable salt thereof not only had both of an inhibitory effect on human serotonin reuptake and binding affinity for human 5-HT1A receptors but had a high inhibitory effect on human serotonin reuptake.

TABLE 1

| Compound (Compound No.) | Test Example 1: h-SERT binding inhibition constant (Ki)[nM] | Test Example 2: h-5-HT$_{1A}$binding inhibition constant (Ki)[nM] |
|---|---|---|
| 5-1 | 6.3 | 12 |
| 5-2 | 72 | 33 |
| 5-3 | 2.7 | 7.4 |
| 5-4 | 18 | 5.5 |
| 5-5 | 11 | 1.1 |
| 5-6 | 0.27 | 2.0 |
| 5-7 | 3.5 | 2.1 |
| 5-8 | 6.5 | 1.3 |
| 5-9 | 1.7 | 0.27 |
| 5-10 | 1.3 | 33 |
| 5-11 | 2.2 | 17 |
| RE1 | 376 | IC$_{50}$ > 10 μM |
| RE2 | 228 | IC$_{50}$ > 10 μM |
| 4-10 | 700 | 91 |
| 4-11 | IC$_{50}$ > 10 μM | 67 |
| 4-12 | IC$_{50}$ > 10 μM | IC$_{50}$ > 10 μM |
| 5-12 | 8.2 | 184 |
| 5-13 | 4.6 | 22 |
| 5-14 | 0.88 | 2.5 |
| 5-15 | 41 | 8.5 |

Test Example 3

CYP2D6 Inhibition Screening Test 3-1 Materials

Bufuralol hydrochloride was purchased from Toronto Research Chemicals Inc., and pooled human liver microsomes were purchased from Xenotech, LLC.

3-2-1 Preparation of 0.5 M Potassium Phosphate Buffer (pH 7.4)

150 mL of a 0.5 M monopotassium phosphate solution and 700 mL of a 0.5 M dipotassium phosphate solution were mixed to adjust the pH 7.4.

3-2-2 Preparation of 165 mM Magnesium Chloride Solution

Magnesium chloride hexahydrate was dissolved in distilled water to adjust the MgCl$_2$.6H$_2$O concentration to 3.35 g/100 mL.

3-2-3 Preparation of Human Liver Microsome Solution

150 μL of the pooled human liver microsomes (20 mg/ml), 12 mL of the 0.5 M potassium phosphate buffer, 1.2 mL of the 165 mM magnesium chloride solution and 34.65 mL of distilled water were mixed to prepare a human liver microsome solution.

3-2-4 Preparation of 13 mM β-NADPH Solution

β-NADPH was dissolved in distilled water at a concentration of 11.75 mg/mL to prepare a 13 mM β-NADPH solution.

3-2-5 Preparation of Substrate Solution

Bufuralol hydrochloride was dissolved in DMSO at a concentration of 1.0 mM and then diluted 20-fold with distilled water.

3-3 Experimental Procedures

1. A 10 mM solution of a test drug in DMSO was serially diluted with DMSO at four 5-fold dilutions to prepare 10, 2, 0.4 and 0.08 mM DMSO solutions.
2. Each test drug solution of step 1 or DMSO was diluted 160-fold with the human liver microsome solution and dispensed at a concentration of 80 μL/well to a microplate.
3. 10 μL of the substrate solution and 10 μL of the β-NADPH solution were added to each well of step 2, and the mixture was incubated at 37° C. for 10 min.
4. The reaction was terminated by the addition of 300 μL of methanol.
5. The reaction mixture was filtered and analyzed by LC-MS/MS.

3-4 Quantification and Calculation

The amount of 1'-hydroxybufuralol formed was determined by LC-MS/MS, and this value was used as the metabolic activity value of CYP2D6 in each well. The residual activity of each sample-supplemented group was determined by comparison with the activity in the well containing DMSO used as a test drug. IC$_{50}$ values in CYP2D6 inhibition were determined from the test drug concentrations. The IC$_{50}$ values were calculated from a line connecting two points that spanned 50% residual activity. The larger numeric value of IC$_{50}$ in CYP2D6 inhibition means weaker CYP2D6 inhibition.

Test Example 4

Screening Test on Contribution Ratio of CYP2D6 in Human Liver Microsomal Metabolism 0.2 mL of a 50 mM potassium phosphate buffer (pH 7.4) containing 3 mM (final concentration) NADPH (manufactured by Oriental Yeast Co., Ltd.), 1 mg/mL human liver microsomes (manufactured by Xenotech, LLC) and 1 μM test substance was warmed in a water bath at 37° C. for metabolic reaction. After 15- or 30-minute reaction, the reaction was terminated by the addition of a 3-fold volume of methanol with respect to the reaction solution and subsequent stirring. This reaction solution was centrifuged to precipitate proteins. Then, the supernatant was collected and subjected to LC-MS/MS analysis. The results were analyzed as follows:

The test substance was quantified, and time-dependent change in its residual amount was logarithmically plotted. The rate of metabolism was calculated from the slope.

The ratio of the rate of metabolism in the presence of quinidine added at 4 μM (final concentration) to the reaction solution to that in the absence of quinidine was used as the contribution ratio of enzymes other than CYP2D6. The remaining portion was used as the contribution ratio of CYP2D6. Specifically, it was calculated according to the formula:

Contribution ratio (%)={1−(Rate of metabolism [in the presence of quinidine]/Rate of metabolism [in the absence of quinidine])}×100

The smaller numeric value of the contribution ratio of CYP2D6 means the small contribution of CYP2D6.

The compounds of the present invention obtained in Examples were subjected to the tests of Test Examples 3 and 4, and the results are shown in Table 2. These test results demonstrated that the compound of the present invention or the pharmaceutically acceptable salt thereof had weaker CYP2D6 inhibition and underwent metabolism to which CYP2D6 made a small contribution.

TABLE 2

| Compound No. | Test Example 3: CYP2D6 inhibition IC$_{50}$ [μM] | Test Example 4: CYP2D6 contribution ratio [%] |
|---|---|---|
| 5-1 | 34.0 | 39*) |
| 5-2 | 40.7 | -**) |

TABLE 2-continued

| Compound No. | Test Example 3: CYP2D6 inhibition IC$_{50}$ [μM] | Test Example 4: CYP2D6 contribution ratio [%] |
|---|---|---|
| 5-3 | 36.2 | 0*) |
| 5-4 | >50 | 0*) |
| 5-5 | 23.0 | 24 |
| 5-6 | 28.3 | 31 |
| 5-7 | 34.9 | 9.2*) |
| 5-8 | 9.9 | 98 |
| 5-9 | 16.8 | 46 |
| 5-10 | 44.9 | N.T. |
| 5-11 | 17.8 | 19 |
| 5-12 | 42.5 | 0 |
| 5-13 | >50 | 0 |
| 5-14 | 37.6 | 8 |
| 5-15 | 40.3 | 0*) |

"N.T." represents not conducted.
*)Reference value due to relative stability in human microsomal metabolism.
**)It was impossible to determine the contribution ratio of CYP2D6 in the test due to stability in human microsomal metabolism.

Preparation Example 1

Production of Tablets 6-(2-{4-[4-Bromo-3-(2-methoxyethoxy)benzyl]piperidin-1-yl}ethyl)-3-hydroxy-2,3-dihydro-4H-chromen-4-one (5 g), lactose (80 g), corn starch (30 g), crystalline cellulose (25 g), hydroxypropylcellulose (3 g) and light anhydrous silicic acid (0.7 g) are mixed and granulated by a routine method and further mixed with magnesium stearate (1.3 g). The mixture is compressed into 145 mg/tablet to produce 1000 tablets.

Preparation Example 2

Production of Powders 6-(2-{4-[4-Bromo-3-(2-methoxyethoxy)benzyl]piperidin-1-yl}ethyl)-3-hydroxy-2,3-dihydro-4H-chromen-4-one (10 g), lactose (960 g), hydroxypropylcellulose (25 g) and light anhydrous silicic acid (5 g) are mixed by a routine method. From the mixture, powders are produced.

Industrial Applicability

A compound of the present invention represented by the formula (1) and a pharmaceutically acceptable salt thereof are characterized in terms of their chemical structure by having a disubstituted benzyl group in which 3-position of the benzene ring moiety is substituted by a hydroxy group, a 2-methoxyethoxy group or a 2-hydroxyethoxy group, and having, at 1-position of piperidine, a 2-(chroman-6-yl)ethyl group or a 2-(4H-chromen-6-yl)ethyl group substituted by a hydroxy group and/or an oxo group. Furthermore, the compound of the present invention and the pharmaceutically acceptable salt thereof are novel serotonin reuptake inhibitors that also have affinity for serotonin 1A receptors, have an improved inhibitory activity against human serotonin reuptake, and have a weaker inhibitory effect on CYP2D6, a human cytochrome P450 molecular species, or undergo drug metabolism in humans to which CYP2D6 makes a small contribution. Thus, the compound and the salt can be used as, for example, highly safe therapeutic or preventive drugs excellent in therapeutic effect, for disease such as depression or anxiety (anxiety disorder).

The invention claimed is:

1. A compound represented by a formula (1) or a pharmaceutically acceptable salt thereof:

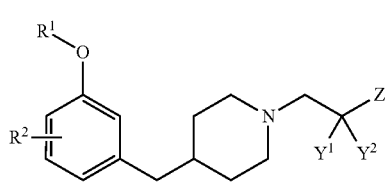
(1)

wherein R$^1$ represents a hydrogen atom or a group represented by a formula (2):

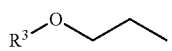
(2)

wherein R$^3$ represents a hydrogen atom or a methyl group;

R$^2$ represents a chlorine atom bonded at the p-position, a bromine atom bonded at the p-position, a methyl group bonded at the p-position, a chlorine atom bonded at the m-position or a bromine atom bonded at the m-position, with respect to a methylene group bonded to a piperidine ring;

Y$^1$ represents a hydrogen atom, and Y$^2$ represents a hydrogen atom or a hydroxy group or Y$^1$ and Y$^2$ together represent an oxo group; and Z represents a group represented by a formula (3-1-1), (3-1-2), (3-2-1), (3-2-2), (3-3-1), (3-3-2), (3-4-1) or (3-4-2):

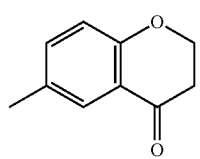
(3-1-1)

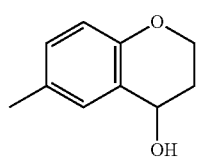
(3-2-1)

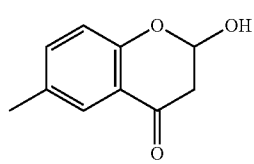
(3-3-1)

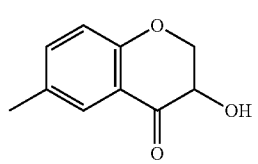
(3-4-1)

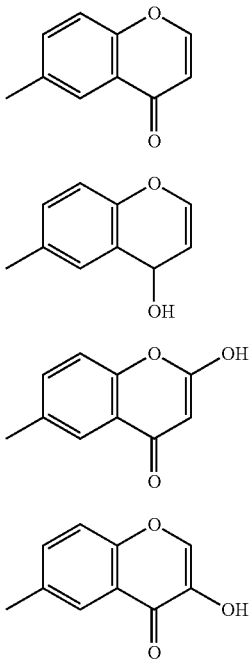

wherein when R¹ represents a group represented by the formula (2) and each of Y¹ and Y² represents a hydrogen atom, Z represents a group selected from the group consisting of the formulas (3-1-2), (3-2-1), (3-2-2), (3-3-1), (3-3-2), (3-4-1) and (3-4-2).

2. The compound according to claim 1 or a pharmaceutically acceptable salt thereof, wherein R² is a bromine atom bonded at the p-position.

3. The compound according to claim 1 or a pharmaceutically acceptable salt thereof, wherein Z is a group represented by the formula (3-1-1), (3-2-1), (3-3-1) or (3-4-1).

4. The compound according to claim 1 or a pharmaceutically acceptable salt thereof, wherein Z is a group represented by the formula (3-1-1), (3-2-1), (3-4-1) or (3-4-2).

5. The compound according to claim 1 or a pharmaceutically acceptable salt thereof, wherein each of Y¹ and Y² is a hydrogen atom.

6. The compound according to claim 1 or a pharmaceutically acceptable salt thereof, wherein Y¹ is a hydrogen atom, and Y² is a hydroxy group.

7. The compound according to claim 1 or a pharmaceutically acceptable salt thereof, wherein the compound represented by the formula (1) is a compound selected from the group consisting of the following compounds (01) to (11):
  (01) 6-(2-{4-[4-Bromo-3-(2-methoxyethoxy)benzyl]piperidin-1-yl}ethyl)-3-hydroxy-2,3-dihydro-4H-chromen-4-one,
  (02) 6-(2-{4-[4-Bromo-3-(2-hydroxyethoxy)benzyl]piperidin-1-yl}ethyl)-3-hydroxy-2,3-dihydro-4H-chromen-4-one,
  (03) 6-{12-[4-(4-Bromo-3-hydroxybenzyl)piperidin-1-yl]ethyl}-3-hydroxy-2,3-dihydro-4H-chromen-4-one,
  (04) 6-(2-{4-[4-Bromo-3-(2-methoxyethoxy)benzyl]piperidin-1-yl}ethyl)-4H-chromen-4-one,
  (05) 6-(2-{4-[4-Bromo-3-(2-hydroxyethoxy)benzyl]piperidin-1-yl}ethyl)-4H-chromen-4-one,
  (06) 6-{2-[4-(4-Bromo-3-hydroxybenzyl)piperidin-1-yl]ethyl}-4H-chromen-4-one,
  (07) 6-(2-{4-[4-Bromo-3-(2-methoxyethoxy)benzyl]piperidin-1-yl}-1-hydroxyethyl)-2,3-dihydro-4H-chromen-4-one,
  (08) 6-(2-{4-[4-Bromo-3-(2-methoxyethoxy)benzyl]piperidin-1-yl}ethyl)-3,4-dihydro-2H-chromen-4-ol,
  (09) 6-(2-{4-[4-Bromo-3-(2-methoxyethoxy)benzyl]piperidin-1-yl}ethyl)-3-hydroxy-4H-chromen-4-one,
  (10) 6-(2-{4-[4-Bromo-3-(2-hydroxyethoxy)benzyl]piperidin-1-yl}ethyl)-3-hydroxy-4H-chromen-4-one, and
  (11) (-)-6-(2-{4[4-Bromo-3-(2-methoxyethoxy)benzyl]piperidin-1-yl}ethyl)-3,4-dihydro-2H-chromen-4-ol.

8. The compound according to claim 1 or a pharmaceutically acceptable salt thereof, wherein R² is a bromine atom bonded at the p-position, Z is a group represented by the formula (3-2-1), (3-3-1) or (3-4-1), and each of Y¹ and Y² is a hydrogen atom.

9. The compound according to claim 1 or a pharmaceutically acceptable salt thereof, wherein R² represents a bromine atom bonded at the p-position, Z represents a group represented by the formula (3-2-1), (3-3-1) or (3-4-1), each of Y¹ and Y² represents a hydrogen atom, and R¹ represents a group represented by the formula (2).

10. The compound according to claim 1 or a pharmaceutically acceptable salt thereof, wherein R² is a bromine atom bonded at the p-position, Z is a group represented by the formula (3-2-1), (3-4-1) or (3-4-2), and each of Y¹ and Y² is a hydrogen atom.

11. The compound according to claim 1 or a pharmaceutically acceptable salt thereof, wherein R² represents a bromine atom bonded at the p-position, Z represents a group represented by the formula (3-2-1), (3-4-1) or (3-4-2), each of Y¹ and Y² represents a hydrogen atom, and R¹ represents a group represented by the formula (2).

12. A pharmaceutical composition comprising a compound according to claim 1 or a pharmaceutically acceptable salt thereof as an active ingredient.

13. The compound according to claim 1 or a pharmaceutically acceptable salt thereof, wherein the compound represented by the formula (1) is
  (01) 6-(2-{4[4-Bromo-3-(2-methoxyethoxy)benzyl]piperidin-1-yl}ethyl)-3-hydroxy-2,3-dihydro-4H-chromen-4-one.

14. The compound according to claim 1 or a pharmaceutically acceptable salt thereof, wherein the compound represented by the formula (1) is
  (11) (-)-6-(2-{4[4-Bromo-3-(2-methoxyethoxy)benzyl]piperidin-1-yl}ethyl)-3,4-dihydro-2H-chromen-4-ol.

15. The compound according to claim 1 or a pharmaceutically acceptable salt thereof, wherein the compound represented by the formula (1) is
  (09) 6-(2-{4-[4-Bromo-3-(2-methoxyethoxy)benzyl]piperidin- 1-yl} ethyl)-3-hydroxy-4H-chromen-4-one.

* * * * *